(12) United States Patent
Finn et al.

(10) Patent No.: US 10,385,055 B2
(45) Date of Patent: *Aug. 20, 2019

(54) TRICYCLIC GYRASE INHIBITORS

(71) Applicants: Merck Sharp & Dohme Corp., North Wales, PA (US); Lawrence Livermore National Security, LLC, Livermore, CA (US)

(72) Inventors: John Finn, Encinitas, CA (US); Leslie William Tari, San Diego, CA (US); Zhiyong Chen, San Diego, CA (US); Junhu Zhang, San Diego, CA (US); Douglas Phillipson, Del Mar, CA (US); Suk Joong Lee, San Diego, CA (US); Michael Trzoss, San Diego, CA (US); Daniel Bensen, Carlsbad, CA (US); Xiaoming Li, San Diego, CA (US); Min Teng, San Diego, CA (US); Voon Ong, San Diego, CA (US); Allen John Borchardt, San Diego, CA (US); Thanh To Lam, San Diego, CA (US); Felice C. Lightstone, Fremont, CA (US); Sergio E. Wong, Tracy, CA (US); Toan B. Nguyen, Marlborough, CA (US)

(73) Assignees: MERCK SHARP & DOHME CORP., Rahway, NJ (US); LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/021,314

(22) PCT Filed: Sep. 10, 2014

(86) PCT No.: PCT/US2014/055019
§ 371 (c)(1),
(2) Date: Mar. 11, 2016

(87) PCT Pub. No.: WO2015/038661
PCT Pub. Date: Mar. 19, 2015

(65) Prior Publication Data
US 2016/0222015 A1    Aug. 4, 2016

Related U.S. Application Data

(60) Provisional application No. 61/876,688, filed on Sep. 11, 2013.

(51) Int. Cl.
| | |
|---|---|
| C07D 491/00 | (2006.01) |
| A61K 31/505 | (2006.01) |
| C07D 487/04 | (2006.01) |
| C07D 491/16 | (2006.01) |
| C07F 9/6561 | (2006.01) |
| A61K 31/519 | (2006.01) |

(52) U.S. Cl.
CPC ......... *C07D 487/04* (2013.01); *C07D 491/16* (2013.01); *C07F 9/6561* (2013.01); *A61K 31/519* (2013.01)

(58) Field of Classification Search
CPC .................................................... C07D 487/04
USPC ......................................................... 544/250
See application file for complete search history.

(56) References Cited

U.S. PATENT DOCUMENTS

| | | |
|---|---|---|
| 2005/0022799 A1 | 2/2005 | Bednar |
| 2005/0227992 A1 | 10/2005 | Hurley et al. |
| 2012/0238751 A1 | 9/2012 | Bensen et al. |
| 2015/0246934 A1* | 9/2015 | Bensen ................ C07D 487/04 514/210.16 |

FOREIGN PATENT DOCUMENTS

| | | |
|---|---|---|
| CN | 105189505 A | 12/2015 |
| WO | 2010006032 A1 | 1/2010 |
| WO | 2012125746 A1 | 9/2012 |
| WO | 2014043272 A1 | 3/2014 |

* cited by examiner

*Primary Examiner* — Shengjun Wang
(74) *Attorney, Agent, or Firm* — Fox Rothschild LLP

(57) ABSTRACT

Disclosed herein are compounds having the structure of Formula I and pharmaceutically suitable salts, esters, and prodrugs thereof that are useful as antibacterially effective tricyclic gyrase inhibitors. Related pharmaceutical compositions, uses and methods of making the compounds are also contemplated.

16 Claims, No Drawings

TRICYCLIC GYRASE INHIBITORS

BACKGROUND

Field

The present disclosure relates to the field of medicinal chemistry and in particular to compounds, and pharmaceutical compositions thereof, that are useful as antibiotics. Particularly, tricyclic gyrase compounds inhibit DNA Gyrase B (GyrB) and Topoisomerase IV (ParE) enzymes. Related methods of treating bacterial infections and methods of making the compounds using novel intermediates are also contemplated.

Description of the Related Art

Bacterial infections pose a continuing medical problem because anti-bacterial drugs eventually engender resistance in the bacteria on which they are used. Consequently, a need exists for new drugs with efficacy against pathogenic bacteria for use in the therapy and prophylaxis of bacterial infections.

One target for development of anti-bacterial drugs has been DNA Gyrase B (GyrB) and Topoisomerase IV (ParE) enzymes necessary for DNA replication. Gyrase inhibitors have been disclosed in RE40,245, which is hereby incorporated by reference in its entirety.

Some gyrase inhibitors have a tendency to inhibit ether-à-go-go-related gene (hERG), that encodes ion channel proteins referred to as hERG channels, and can lead to a greater risk of potentially fatal cardiac arrhythmias due to repolarization disturbances of the cardiac action potential, as a side-effect.

The GyrB enzymatic pocket has been characterized in detail in Wigley, D. B. et al., *Nature*, 351(6328), 624-629, 1991. See also. Tsai F T, et al., *The high-resolution crystal structure of a 24-kDa gyrase B fragment from E. coli complexed with one of the most potent coumarin inhibitors, clorobiocin*, Proteins. 1997 May; 28(1):41-52.

The ParE enzymatic pocket has been characterized in detail in Bellon, S., et al. *Crystal structures of Escherichia coli topoisomerase IV ParE subunit (24 and 43 kilodaltons): a single residue dictates differences in novobiocin potency against topoisomerase IV and DNA gyrase*, Antimicrob. Agents Chemother. 48: 1856-1864 (2004). These references are hereby incorporated by reference in their entirety.

In contrast, patent publications naming Hurley et al. as inventors, are directed to protein kinase inhibitors that are useful for protein kinase-mediated diseases and conditions such as cancer. See, e.g., US 2008/0051414, US 2009/0143399, and US 2009/0099165.

PCT/US2012/029104, U.S. Prov. Pat. Appl. 61/700,159, and the PCT application that claims priority to U.S. Prov. Pat. Appl. 61/700,159 (WO 2014/043272), which are licensed or assigned to the same assignees in the present application, disclose tricyclic gyrase inhibitors and are incorporated herein by reference in their entirety.

SUMMARY

Tricyclic gyrase compounds of Formula I inhibit DNA Gyrase B (GyrB) and Topoisomerase IV (ParE) enzymes.

Methods of using the compound to treat antibacterial infections and methods of making the compounds are also contemplated.

These and other related aspects are set forth in more detail below.

DETAILED DESCRIPTION

Compounds in PCT/US2012/029104, U.S. Prov. Pat. Appl. 61/700,159, and the PCT application that claims priority thereto (WO 2014/043272), potently inhibit the GyrB and ParE receptors, and have strong Gram-negative activity. In some aspects, any previously disclosed species of tricyclic gyrase inhibitor compounds in PCT/US2012/029104 or in the U.S. Prov. Pat. Appl. 61/700,159, or the PCT application that claims priority to U.S. Prov. Pat. Appl. 61/700,159 (WO 2014/043272), are excluded herein. One aspect of Gram-negative antibacterial activity is the ability of the compound to penetrate the Gram-negative cell wall and then avoid rapid efflux. In PCT/US2012/029104, U.S. 61/700,159 and the PCT application that claims priority thereto (WO 2014/043272), the most potent and active compounds contain a basic amine, such as a charged diamine at the $R^4$ position of Formula I, and thus are considered particularly advantageous for Gram-negative activity. These $R^4$ diamine compounds have a basic amine that is typically charged at physiological pH. This charged molecule is small and polar and, without being bound by theory, was thought to be able to penetrate Gram-negative cells by entry via the porins. The molecule also exists in equilibrium with a small (2-5%) portion of the neutral species, which, without being bound by theory, was thought to penetrate the inner membrane. Once in the cytosol, the compound exists mainly as a polar charged molecule and is less likely to be effected by efflux pumps in contrast to neutral molecules, such as compounds with a non-basic alcohol at the $R^4$ position. For example, species of compounds disclosed in the PCT application that claims priority to U.S. Prov. Pat. Appl. 61/700,159 (WO 2014/043272), such as

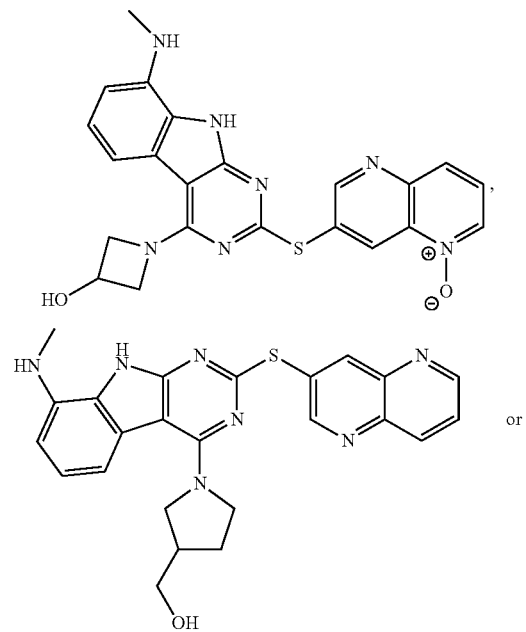

or

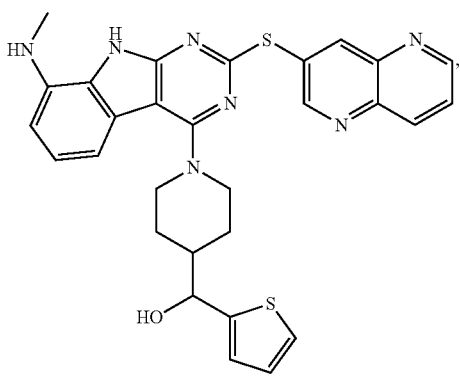

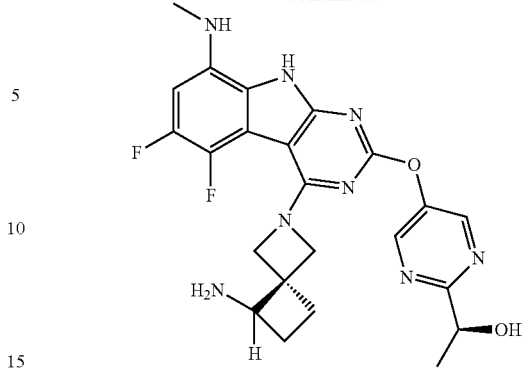

have a non-basic alcohol at the $R^4$ position but have relatively low Gram-negative activity, in comparison to the most active basic amine compounds. The Ec (*E. coli*) MICs for the three compounds identified above are >64 μg/mL; 8 μg/mL; and >32 μg/mL, respectively. Without being bound by theory, it is believed that a) the sulfur L linker, and b) a 10-membered heteroaryl having two fused rings of the $R^2$ group may make it difficult for the compound to pass through the porins in the Gram-negative cell wall.

It would be advantageous if potent compounds having Gram-negative activity also avoided serious side effects resulting from off-target binding. Cardiovascular side effects are a major reason for drug failures. Inhibition of hERG (human ether a go-go related gene) is used as a predictive in vitro enzymatic screen to eliminate compounds with cardiovascular side effects especially prolongation of the QTc interval (Valentin. J. *British Journal of Pharmacology* 2010, 159, 5-11). It would be beneficial to the art if compounds avoided the unwanted side effect of hERG channel inhibition. In the PCT application that claims priority to U.S. Prov. Pat. Appl. 61/700,159 (WO 2014/043272), specific compounds having a diamine at the $R^4$ position were found to be unexpectedly and significantly more selective in the hERG assay than many other tested compounds having a diamine at the $R^4$ position, while retaining Gram-negative activity. These species of compounds, namely

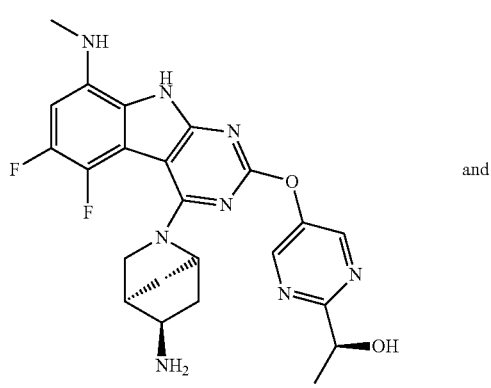

and have CF's at both Y and Z positions and have a hydroxyethyl substituent on $R^2$. For these species with positive hERG results, however, it was found that replacing the basic amine with a neutral alcohol at the $R^4$ position in somewhat similar compounds (CF's at both Y and Z positions and hydroxyethyl substituent on $R^2$) resulted in similarly positive hERG results, but the Gram-negative activity diminished. It would also be advantageous if compounds could have both positive hERG values and retain Gram-negative activity.

Moreover, it would also be advantageous in the art if compounds could be administered orally, in addition to having Gram-negative activity and avoiding the unwanted side effect of hERG channel inhibition described above. However, many antibiotics are limited to intravenous administration because they lack the ability to traverse the small intestinal mucosa that facilitates oral absorption. Many factors influence oral absorption, and hence oral bioavailability. Some factors relate to molecular properties, such as solubility, dissolution and permeability, which are well known. However, other molecular properties, such as molecular flexibility, number of rotatable bonds or polar surface area, are less well understood. Without being bound by theory, it is believed that a combination of these molecular properties confers oral bioavailability to the compound. It is difficult to predict which combination of molecular properties would yield a compound having oral bioavailability, therefore empirical testing is useful to determine oral bioavailability.

To achieve these goals, chemical diversity was explored at various R groups on the ABC Ring. The solvent exposed R groups, i.e., $R^2$ and $R^4$, provided the best opportunity for chemical diversity leaving the remaining groups positioned in the protein's interior when in the bound conformation to interact with the GyrB and PyrE active site pockets.

It was entirely unexpected that, in some aspects, the compounds herein could simultaneously: 1) potently inhibit GyrB and ParE and retain Gram-negative activity; and 2) avoid the unwanted side effect of hERG channel inhibition; and further, in some aspects, provide excellent oral bioavailability.

Oral bioavailability can be assessed by various methods such as measuring the Caco-2 cell monolayer permeability, and measuring pharmacokinetic properties by calculating the ratio of the AUC from oral administration to the AUC from intravenous administration. Both methods are used to assess compounds here as illustrated in Examples 8-9. In some aspects, compounds herein show the highest membrane (Caco-2 cell monolayer) permeability among all the compounds tested. The Caco-2 cell line is a continuous cell of heterogeneous human epithelial colorectal adenocarcinoma cells that when cultured under specific conditions the cells become differentiated and polarized such that their phenotype, morphologically and functionally, resembles the enterocytes lining the small intestine. Thus, the Caco-2 monolayer is widely used across the pharmaceutical industry as an in vitro model of the human small intestinal mucosa to predict the absorption of orally-administered drugs.

Certain aspects of the compounds of Formula I are elaborated below. In Formula I above, aspects of the variables on the ABC Ring, i.e. L, $R^2$, $R^4$, $R^8$, X, Y, and Z have been discussed in detail in PCT/US2012/029104 and U.S. Prov. Pat. Appl. 61/700,159, or the PCT application that claims priority to U.S. Prov. Pat. Appl. 61/700,159 (WO 2014/043272), and relevant aspects, such as the compounds' interactions with GryB and ParE, are incorporated herein by reference.

As used herein, the term "aryl" refers to optionally-substituted monocyclic and fused bicyclic hydrocarbyl moiety. Any monocyclic or fused ring bicyclic system which has the characteristics of aromaticity in terms of electron distribution throughout the ring system is included in this definition. Typically, the ring systems contain 5-12 ring member atoms. "Heteroaryl" refers to optionally-substituted aromatic monocyclic and fused bicyclic heterocycles containing one or more heteroatoms selected from N, O and S. The inclusion of a heteroatom permits inclusion of 5-membered rings as well as 6-membered rings.

As used herein, the term "alkyl," include straight- and branched-chain and cyclic monovalent substituents. Examples include methyl, ethyl, propyl, isopropyl, and cyclopropyl. Where indicated, the alkyl substituents may contain 1-10C (1 to 10 carbon atoms) such as 1-3C, 1-6C, or 1-8C.

As used herein, "hydrocarbyl residue" refers to a residue which contains only carbon and hydrogen. The hydrocarbyl residue may be saturated or unsaturated, aliphatic or aromatic, straight-chain, branched-chain, or cyclic including a single ring, a fused ring system, a bridge ring system, or a spiro ring system, or a combination of hydrocarbyl groups. The hydrocarbyl residue, when so stated however, may contain heteroatoms over and above the carbon and hydrogen members of the substituent residue. Thus, when specifically noted as containing such heteroatoms, the hydrocarbyl residue may also contain heteroatoms such as O, S or N within the "backbone" of the hydrocarbyl residue. A hydrocarbyl group may include a combination of hydrocarbyl containing moieties such as a heterocyclic group, linked to a heteroalkyl containing a combination of a straight chain alkyl and a cycloalkyl group.

As used herein, "cyclic residue" refers to a cyclic hydrocarbyl residue, which contains only carbon and hydrogen. The cyclic residue, when so stated however, may contain heteroatoms over and above the carbon and hydrogen members of the substituent residue. Thus, when specifically noted as containing such heteroatoms, the heterocyclic residue may also contain heteroatoms such as O, S or N within the "backbone" of the cyclic residue. In some aspects, when so stated, the cyclic residue is a cycloaliphatic or cycloheteroaliphatic residue. A saturated cycloaliphatic or saturated cycloheteroaliphatic residue refers to a ring containing saturated bonds between each ring member.

As used herein, "unsaturated cyclic residue" refers to an at least partially unsaturated or aromatic cyclic hydrocarbyl residue, which contains only carbon and hydrogen. The unsaturated cyclic residue, when so stated however, may contain heteroatoms over and above the carbon and hydrogen members of the substituent residue. Thus, when specifically noted as containing such heteroatoms, the unsaturated heterocyclic residue may also contain heteroatoms such as O, S or N within the "backbone" of the unsaturated cyclic residue.

The term "members" or "membered" in the context of heterocyclic and heteroaryl groups refers to the total atoms, carbon and heteroatoms N, O and/or S, which form the ring. Thus, an example of a 6-membered saturated cycloheteroaliphatic ring is piperidine and an example of a 6-membered heteroaryl ring is pyridine. Of course, "members" or "membered" also refers to the number of carbon atoms in non-heteroatom or non-cyclic containing moieties.

The bound conformation refers to the conformation (i.e., the spatial arrangement of atoms) the tricyclic gyrase compound would assume if it was bound to the GyrB/ParE active-site pocket in the enzyme's interior. In use, the compound may interact with the active site pocket and inhibit the ATPase activity. When the compound is bound to the GyrB/ParE active-site pocket, some substituents interact with certain amino acids and thus the substituents' ability to rotate freely about a bond is constrained. Thus, more useful measurements may be made to determine distances relevant for determining the dimensions of proper substituents. When indicated, measurements are based on the relative positions of substituents on the compound while hypothetically bound to the GyrB/ParE active-site pocket. References to the bound conformation with respect to the compound should not be interpreted as literally encompassing the GyrB/ParE active-site pocket in combination with the compound. The bound conformation is characterized via measurements derived from the three dimensional structure from x-ray crystallographic data on the inhibitor complexed with a protein construct that typically encompasses the 24 or 46 kDa ATP-binding domain of one or more representative bacterial GyrB or ParE orthologs. Given the high degree of sequence identity between GyrB and ParE enzymes in most pathogenic organisms of interest, structural information derived from a protein ortholog from any pathogen of clinical relevance should be sufficient to describe the bound conformation. Briefly, crystallographic structures are generated using the following methods: Proteins of interest (e.g., *E. faecalis* GyrB, *E. coli* GyrB, *F. tularensis* ParE or *E. coli* ParE) are generated in a standard *E. coli* expression system. The open reading frames are cloned into an expression plasmid (e.g., pET28a), and expressed in and appropriate *E. coli* expression strain (e.g., BL21 (DE3)). For crystallography the 24 kDa and 46 kDa ATP binding domains are cloned with a C(His)$_6$ tag to aid purification by metal affinity chromatography. This robust chromatography step typically yields greater than 80% pure protein. Polishing steps including ion exchange and size exclusion chromatography, are performed as needed until satisfactory (>95%) purity is achieved. Once purified protein is available, complexes of GyrB or ParE and the inhibitor molecule of interest are generated by mixing a stoichiometric excess of the inhibitor of interest with the recombinant protein target in solution and crystallizing the complex using established crystallization methods (typically vapor diffusion, as described in Drenth J. (1999) In Principles of protein x-ray crystallography. $2^{nd}$ ed. Springer, New York). Once crystallized, x-ray diffraction data are collected on single crystals of the protein-inhibitor complexes using monochromatic x-rays generated by a rotating anode or synchrotron radiation source. X-ray data processing, analysis and subsequent structure solution and refinement are carried out using well established computational methods (reviewed in Drenth J. (1999) In Principles of protein x-ray crystallography. $2^{nd}$ ed. Springer, New York).

Interacting substituents on the compound that interact with the GyrB/ParE active-site pocket include those substituents that would be located within the protein's interior when the compound is in the bound conformation. Interactions of interacting substituents generally include hydrophobic interactions (which favor the apposition of lipophilic surfaces on the inhibitor and active-site pocket), and electrostatic interactions such as Van der Waals, dipole-dipole, coulombic interactions or hydrogen-bonding between atoms on the compound and atoms in the GyrB/ParE active-site pocket. For example, $R^8$, $R^X$, $R^Y$, and $R^Z$ interact with various portions of the protein's interior. If $R^8$, $R^X$, $R^Y$, or $R^Z$ is $NH_2$ or NHR (where R is, for example, a small alkyl group), the H atom(s) on the nitrogen may interact with electronegative atoms, such as nitrogen or oxygen, proximally located in the GyrB/ParE active-site pocket to which the compound may bind. When $R^8$, $R^X$, $R^Y$, and $R^Z$ are non-polar (e.g., a methyl group), the interacting substituent may also electrostatically interact with an atom in the protein's interior via Van der Waals interactions, and desolvate complementary lipophilic surfaces in the active-site pocket to form favorable hydrophobic interactions. Additionally, in some aspects, the shape and size of the active-site may place restrictions on the dimensions of compound's substituents that would be sterically compatible with the active-site pocket.

Where indicated, the dimensions of a substituent may be provided and are associated with the dimensions of the pocket in which the compound would be situated if in a bound conformation. For example, the length of a substituent may be given based on its distance from the atom on the tricyclic scaffold to the substituent's atom that is positioned farthest from the tricyclic scaffold, i.e., the terminal atom. The distance is measured based on the center of a first atom such as a C on the tricyclic scaffold, to the center of the terminal atom. The distance is measured from point to point in a straight line regardless of the fact that the bonds in the substituent are not linearly aligned, such as an ethyl or OH substituent.

Compounds herein have the structure of Formula I

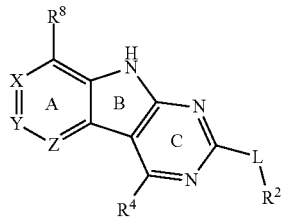

Formula I or pharmaceutically suitable salts, esters, and prodrugs thereof.

L may be O, S, NH or $CH_2$;
X may be CH and $R^8$ may be $NHCH_3$.

In some aspects, $R^8$ may be a prodrug-containing substituent, wherein the prodrug is cleaved to form a compound that has dimensions appropriate for the length from the tricyclic scaffold carbon to the active site pocket based on crystallographic data as described above. These prodrugs, such as Formula II, among others, are described in more detail below.

When Z is not joined with $R^4$ to form a fused ring, each of Y and Z may be independently $CR^Y$ or $CR^Z$ respectively, or N, wherein each of $R^Y$ and $R^Z$ is each independently H, halo, such as F, Cl, or Br, $CH_3$, $CF_3$, $CHF_2$, $CH_2F$, or CN.

In some, aspects Z may be C linked to $R^4$. Although not being bound by theory, the potency and/or selectivity may be increased because the conformational entropy is reduced when Z joins with $R^4$ to form a fused ring. When Z is joined with $R^4$ to form a fused ring, Y may be N or $CR^Y$, wherein $R^Y$ is H, halo, e.g., F, Cl, or Br, $CH_3$, $CF_3$, $CHF_2$, $CH_2F$, or CN.

When Z is joined or not joined with $R^4$ to form a fused ring, $CR^Y$, may be CH or CF, such as CF. When Z is not joined with $R^4$ to form a fused ring, $CR^Z$ may be CF or CH, such as CH.

In some aspects, Z may be C linked to $R^4$, wherein the compound has the structure of Formula VI

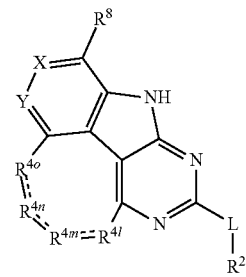

Formula VI $R^{4l}$ may be $CR^{10}$, $CR^{10}CR^{11}$, $NR^{12}$, O or S. $R^{4m}$ may be $CR^{10}$, $CR^{10}CR^{11}$, or $NR^{12}$. $R^{4n}$ may be $CR^{10}$, $CR^{10}CR^{11}$, $NR^{12}$, O or S. Each of $R^{10}$, $R^{11}$ and $R^{12}$ is independently H or a noninterfering substituent, wherein at least one of $R^{10}$, $R^{11}$ and $R^{12}$ is an OH-containing substituent. An OH-containing substituent may be OH, or a C1-C5 hydrocarbyl residue substituted with at least one —OH, such as one or 2 —OH, wherein the C1-C5 hydrocarbyl residue may contain 0-2, such as 0-1, heteroatoms selected from O or S. $R^{10}$, $R^{11}$ and $R^{12}$ may be a noninterfering substituent such as H, C1-C5 alkyl optionally substituted with CN or OH. When $R^{4l}$, $R^{4m}$, $R^{4n}$, $R^{4o}$ is N, and contains an OH containing substituent, in some aspects, a C1-C5 alkyl such as a C2 alkyl, separates the N and the —OH on the OH-containing substituent. Two adjacent $R^{4l}$, $R^{4m}$, and $R^{4n}$, together may form a fused ring, such as a C or N in the D Ring may form a ring with two of $R^{10}$, $R^{11}$ and $R^{12}$. In some aspects. $R^{10}$, $R^{11}$ and/or $R^{12}$ do not contain an N, such as a primary or secondary amine. In some aspects, none of $R^{4l}$, $R^{4m}$, $R^{4n}$ and $R^{4o}$ contains a basic amine, as discussed herein.

$R^{4o}$ may be a) a bond, wherein a 7-membered D ring is formed, wherein $R^{4n}$ may be CH, $CH_2$, S, NH, O, CHF, or $CF_2$; or b) a 1 member link in the backbone of the D ring wherein an 8-membered D Ring is formed, wherein the 1 member link may be CH, $CH_2$, S, NH, O, CHF, or $CF_2$. As discussed earlier, a member is a C, O, S, or N ring member such as CH, $CH_2$, CHF, or $CF_2$, NH, O or S.

In some aspects, $R^{4l}$ is O, $CH_2$, or CHOH. In some aspects, $R^{4m}$ is CHOH, $CH(CH_2)_2OH$, or $CHCH(OH)$ $CH_2OH$. In some aspects, $R^{4n}$ is $CH_2$. In some aspects, $R^{4o}$ is a bond.

Two adjacent noninterfering substituents on $R^{4l}$ and $R^{4m}$ may form one or more fused rings. The dashed lines indicate an optional double bond when two adjacent $R^{4l}$, $R^{4m}$, and $R^{4n}$ are $CR^{10}$ and $R^{4o}$ is $R^{4o}$ is CH or N. Thus, in some aspects Formula VI may have the structure of Formula VIa:

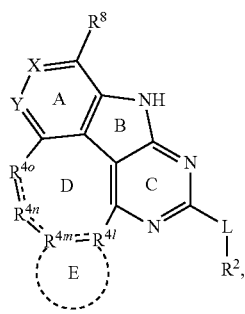

Formula VIa

The dotted lines indicate substituents on $R^{4l}$ and $R^{4m}$ that form a fused ring E that may be optionally substituted with a noninterfering substituent.

In some aspects, the portion of the E Ring linking $R^{4l}$ and $R^{4m}$ is a C1-C10 hydrocarbyl residue containing 0-5 O or S, attached to the D Ring at $R^{4l}$ and $R^{4m}$, optionally substituted with OH, CN, =O, =NOH, =NOCH$_3$, Br, F, Cl, SO$_3$H, or NO$_2$. CN, =NOH, =NOCH$_3$, and NO$_2$ are not amines, and thus not basic amines.

For example, $R^{4l}$ and $R^{4m}$ together with two noninterfering substituents may form a fused 3, 4, 5, or 6 membered E Ring containing 0-1 O, S or N atoms, optionally substituted with halogen, such as chloro. The E Ring may be fused, spiro or bridged.

In addition, —$R^{4o}$—$R^{4n}$—$R^{4m}$—$R^{4l}$—, i.e.,

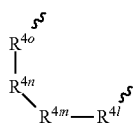

may be selected from the following moieties:
—CH$_2$CH(CH$_2$OH)O—, —CH$_2$CH(CH$_2$CH$_2$OH)O—, —CH$_2$CH((CHOH)CH$_2$OH)CH(OH)—, —CH$_2$CH(OH)CH$_2$—, —CH$_2$CH(OH)CH(OH)—,

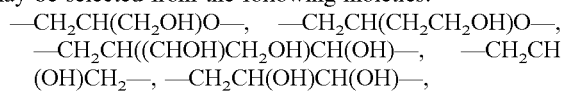

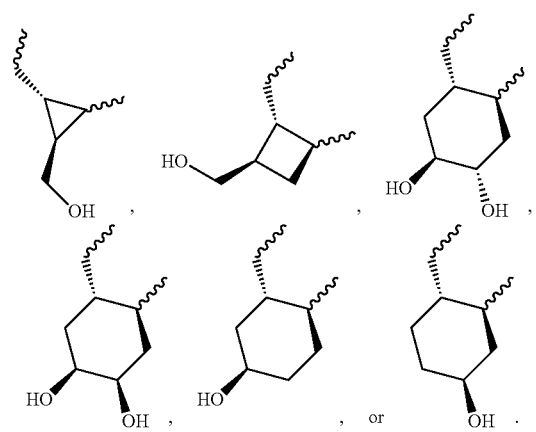

In some aspects, D Ring may contain an O, S or N in the backbone.

In some aspects, two adjacent noninterfering substituents on $R^{4m}$ and $R^{4n}$ may form one or more fused rings. The dashed lines indicate an optional double bond when two of $R^{4l}$, $R^{4m}$, and $R^{4n}$ are $CR^{10}$ and $R^{4o}$ is $R^{4o}$ is CH or N. Thus, in some aspects Formula VI may have the structure of Formula VIb:

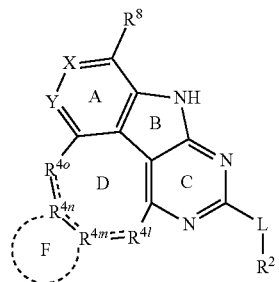

Formula VIb

In some aspects, the portion of the F Ring linking $R^{4m}$ and $R^{4n}$ is a C1-C15 hydrocarbyl residue containing 0-5 O, S, or N heteroatoms, attached to the D Ring at $R^{4m}$ and $R^{4n}$, optionally substituted with OH, CN, =O, =NOH, =NOCH$_3$, Br, F, Cl, SO$_3$H, or NO$_2$.

Although not being bound by theory, it is useful when the F Ring avoids steric hindrance and avoids interference with the compound's binding to the enzyme's active site. Thus, in some aspects, if an F Ring is present, $R^{4o}$ may not be a bond. If $R^{4o}$ is a 1 member link, the portion of the F Ring linking $R^{4m}$ and $R^{4n}$, if present, may be an unsubstituted C1 residue, or C1 substituted with a small substituent such as F or OH substituent forming an unsubstituted cyclopropyl residue (or substituted with small substituent) with $R^{4m}$ and $R^{4n}$. If $R^{4o}$ is a 1 member link, the portion of the F Ring linking $R^{4m}$ and $R^{4n}$ may be a C2-C10 hydrocarbyl residue containing 0-5 O, S, or N heteroatoms, however, the position on the F ring immediately adjacent $R^{4n}$ may be unsubstituted or substituted with a small substituent such as F or OH.

For example, $R^{4m}$ and $R^{4n}$ together with two noninterfering substituents may form a fused 3, 4, 5, or 6 membered F Ring containing 0-1 O, S or N atoms, optionally substituted with halogen, such as fluoro or OH. The F Ring may be fused, spiro or bridged.

Although not being bound by theory, it is useful when the D Ring avoids steric hindrance and avoids interference with the compound's binding to the enzyme's active site. In some aspects, the D ring does not project greater than about 3 Å below the plane of the A, B and C Rings toward the GyrB/ParE binding pocket floor in the bound conformation; and the D ring does not sterically interfere with $R^2$ when the compound is in the bound conformation.

In some aspects, the compound of Formula VI may be one of the following compounds:

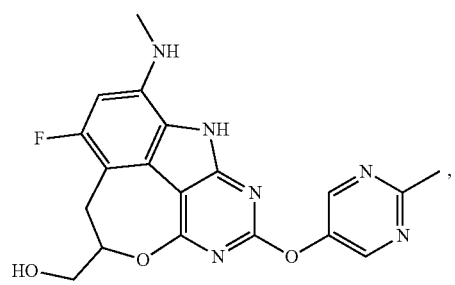

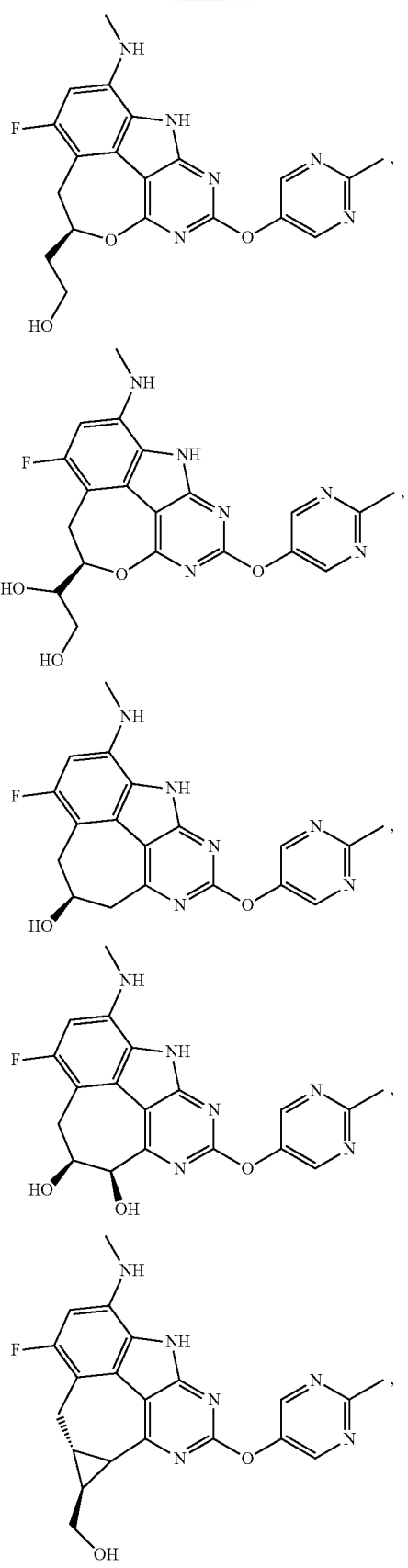
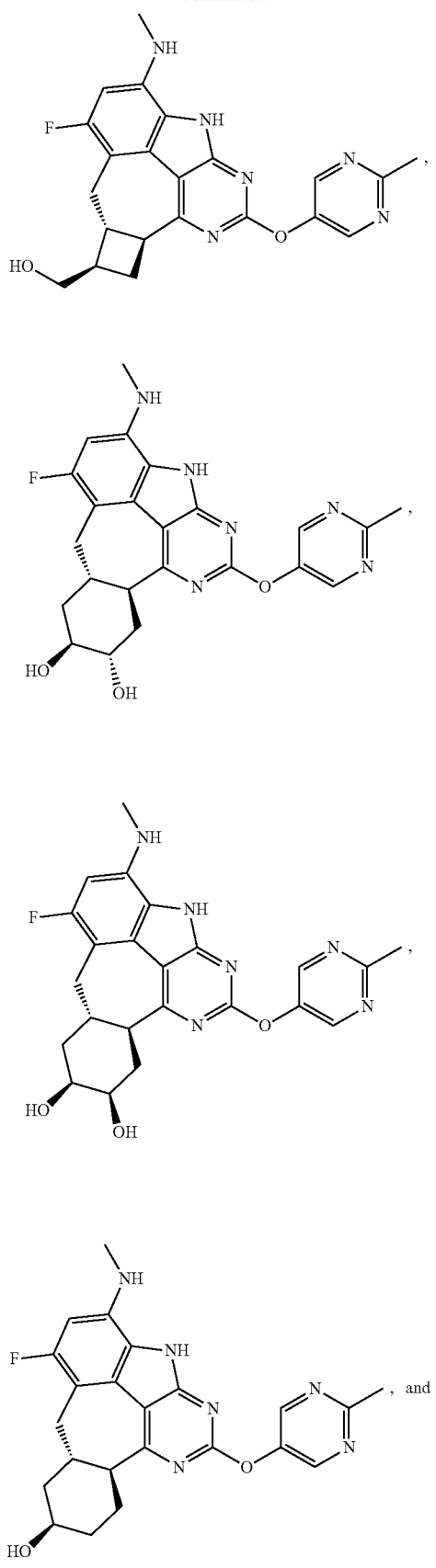

-continued

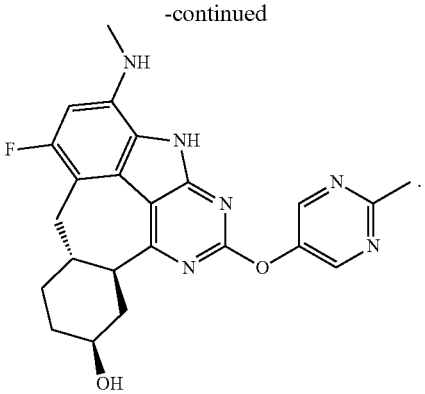

The above compounds may also be made using the R² substituents as described herein.

Without being bound by theory, R² may be useful for conferring selectivity and potency against eukaryotic ATP binding proteins, such as kinases and HSP90. Thus, one of the compounds' benefits includes avoiding toxicity due to off target binding, such as to a kinase, due in part to R²'s selectivity as part of the compound. Generally, in some aspects, the compounds are not potent inhibitors for eukaryotic kinases.

In some aspects, R² is phenyl, thiadiazolyl, such as 1,3,4-thiadiazolyl, pyridinyl or pyrimidinyl optionally substituted with a noninterfering substituent wherein 2 optional noninterfering substituents may join to form a fused ring; or R² is a prodrug-containing substituent discussed below in more detail.

Solvent exposed faces of the GyrB/ParE active-site pockets allow portions of the compound to be exposed to a solvent environment when in use. In some aspects, noninterfering substituents may be water soluble to afford compatibility with an aqueous solvent environment. Proportions of the substituents in the direction of a potential solvent environment are not critical but one skilled in the art would understand that sterically unhindered substituents are useful. Thus, proportions of the solvent-exposed substituents may be diverse.

In contrast to an "interacting substituent," certain positions of the molecule may be described as permitting "noninterfering substituents." This terminology is used because the substituents in these positions generally speaking are less relevant to the activity of the molecule taken as a whole. A wide variety of substituents can be employed in these positions, and it is well within ordinary skill to determine whether any particular arbitrary substituent is or is not "noninterfering."

As used herein, a "noninterfering substituent" is a substituent which leaves the ability of the compound herein such as compounds of Formula I to inhibit bacterial growth of at least one type of bacterium qualitatively intact, such as Gram-negative bacteria. For example, the noninterfering substituent would leave the ability of the compound to provide antibacterial efficacy based on a minimum inhibitory concentration (MIC) of less than 32 µg/ml, or based on inhibition of ATPase activity of DNA Gyrase B (GyrB) or Topoisomerase IV (ParE) of less than 10 nm. Thus, the substituent may alter the degree of inhibition based on MIC or ATPase activity. However, as long as the compound herein such as compounds of Formula I retains the ability to inhibit bacterial/ATPase activity, the substituent will be classified as "noninterfering." A number of assays for determining the MIC or the ability of any compound to inhibit ATPase activity of DNA Gyrase B (GyrB) or Topoisomerase IV (ParE) are available in the art, and some are exemplified in the Examples below. For instance, a coupled spectrophotometric assay, in which the enzyme-dependent release of inorganic phosphate from ATP hydrolysis is measured, determines the inhibitor activity of an arbitrarily chosen compound during incubation with GyrB or ParE upon the addition of ATP.

In some aspects, in addition to the ability to inhibit bacterial activity, the noninterfering substituent leaves the ability of the compound to be more selective in the hERG assay than its amine-containing analog. Further, in some aspects, the noninterfering substituent would leave the ability of the compound to achieve greater oral bioavailability (as measured by Caco and/or % F) than its amine-containing analog.

The features related to the molecule's activity are tightly defined. The positions which are occupied by "noninterfering substituents" can be substituted by conventional moieties as is understood in the art. It is irrelevant to test the outer limits of such substitutions. The relevant features of the compounds are those set forth with particularity herein.

The noninterfering substituents on R²'s ring that may be solvent exposed in the bound conformation may include large substituents such as prodrugs.

Noninterfering substituents of R² include C1-C10 hydrocarbyl residue containing 0-5 O, S or N atoms in the backbone thereof optionally substituted with one or more of OH, =O, or NH₂, wherein two substituents on R² may form a fused ring. Noninterfering substituents include COOH, NH₂, OH, CH₃, CH₂CH₃, NH₂, CH₂NH₂, NHCH₃, CH₂CH₂NH₂, CH₂CH₂OH, CH(CH₃)OH, CH(CH₃)OCH₃, COOH, CONHOCH₂CH₂N(CH₃), CONHOCH₃, CH(CH₃)OCH₂OCH₃, CH₂COOH, CH₂COOCH₃,

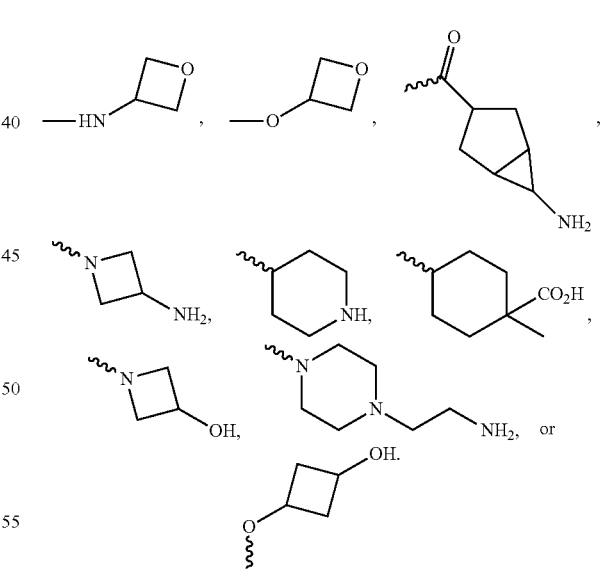

In some aspects R² may be one of the following substituents:

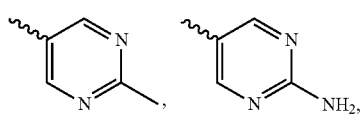

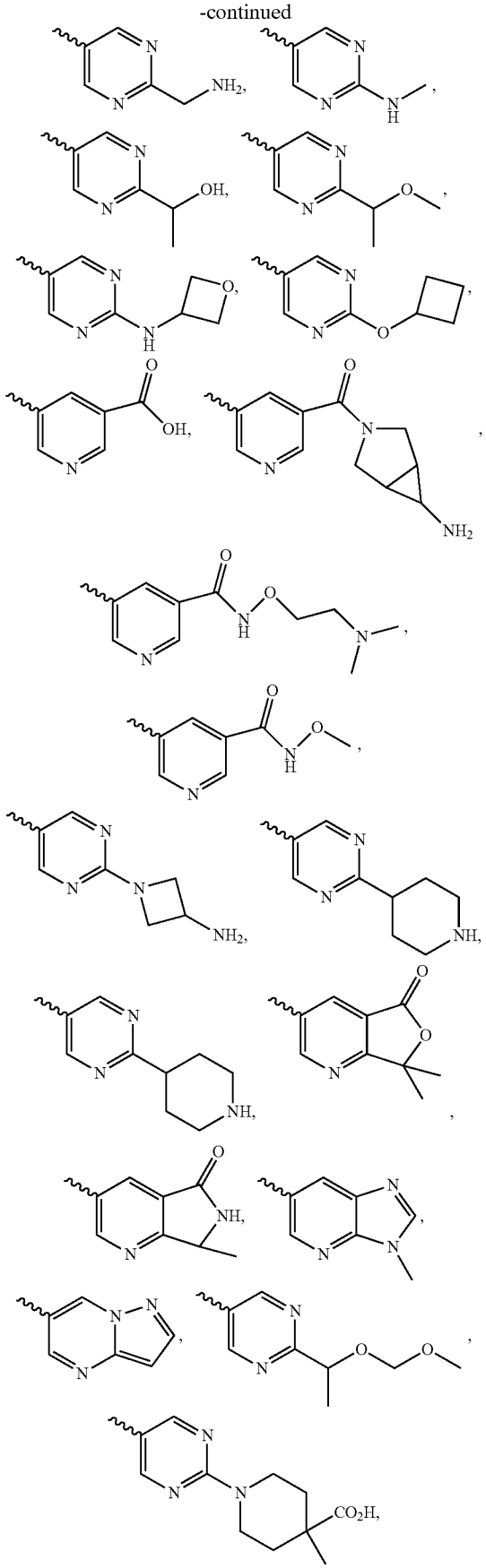

In some aspects, R² is not

As discussed in PCT/US2012/029104, U.S. Prov. Pat. Appl. 61/700,159, or the PCT application that claims priority to U.S. Prov. Pat. Appl. 61/700,159 (WO 2014/043272), the compound is solvent exposed in the bound conformation along the R⁴ bond axis and in a 0-90° counterclockwise sweep from the R⁴ bond axis. Choices for prodrugs and substituents on R⁴, therefore, may be varied. In selecting the R⁴ substituent, in some aspects the R⁴ groups do not sterically interfere with R² or Z groups in the bound conformation. A skilled artisan would understand that to avoid steric interference, atoms on R⁴ should not approach atoms on R² or R^z (in the bound conformation) such that the interatomic distances of the closest atoms are less than the sums of their Van der Waals radii.

In addition, in some aspects, the R⁴ substituent does not project greater than about 3 Å below the plane of the A, B and C Rings toward the GyrB/ParE binding pocket in the bound conformation. "Toward the GyrB/ParE binding floor pocket" refers to not projecting greater than about 3 Å below the plane within about 5-6 bonds from the point of attachment of R⁴ to the scaffold. Thus, portions of R⁴ that extend greater than about 5-6 bonds away from the point of attachment of R⁴ to the C Ring may project greater than about 3 Å below the plane of the A, B and C Rings as these portions are not constrained by the floor of the GyrB/ParE binding pocket.

The distance is defined as the perpendicular distance from the plane aligned with atom centers of the tricyclic scaffold to the center of the most distal atom (from the plane) on the R⁴ substituent in the bound conformation.

When R⁴ is not joined to Z to form a fused ring, R⁴ may be a C3-C20 aliphatic hydrocarbyl residue containing 1-6 heteroatoms selected from O, S, and N wherein one heteroatoms of the 1-6 heteroatoms is an N in the backbone of the hydrocarbyl residue and wherein the N is attached to the C Ring. In some aspects, the C3-C20 aliphatic hydrocarbyl residue is substituted with at least one hydroxyl substituent and 0-3 noninterfering substituents. In some aspects, R⁴ may have optional substituents on the C3-C20 aliphatic hydrocarbyl residue such as OH, =O, CN, halo such as F, NOCH₃, CF₃, OCH₃, OCH₂CH₃. R⁴ does not contain a basic amine. In some aspects, R⁴ does not contain an N, such as a primary or secondary amine (other than the N linked to the C Ring).

Substituents, with respect to R⁴, such as CN, =NOH, =NOCH₃, and NO₂ are not amines, and thus not considered basic amines. Further, when e.g. a morpholinyl is attached to the C Ring via the N in the morpholinyl, the morpholinyl is not considered a basic amine in this case. An amine substituent on a substituted R⁴ such as a substituted morpholinyl R⁴, however may be considered a basic amine, such as a primary (e.g. NH₂) or secondary amine (NH-alkyl). Basic amines, in some aspects, are not included at the R⁴ position in the Formula I compounds herein having an R⁴ with a hydroxyl containing substituent.

R⁴ may be an optionally substituted C3-C20 aliphatic hydrocarbyl residue such as one of:

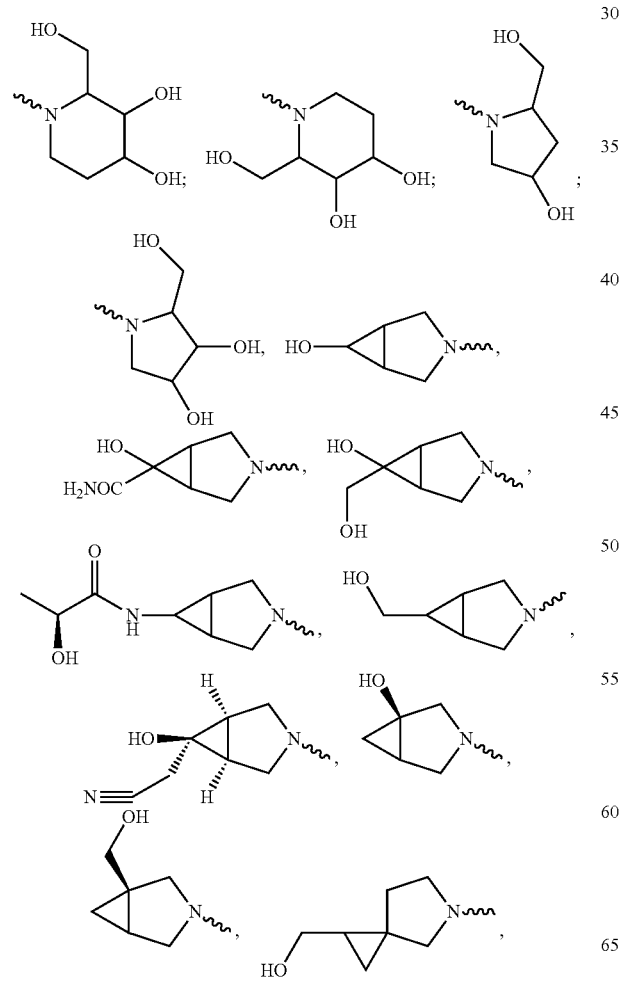

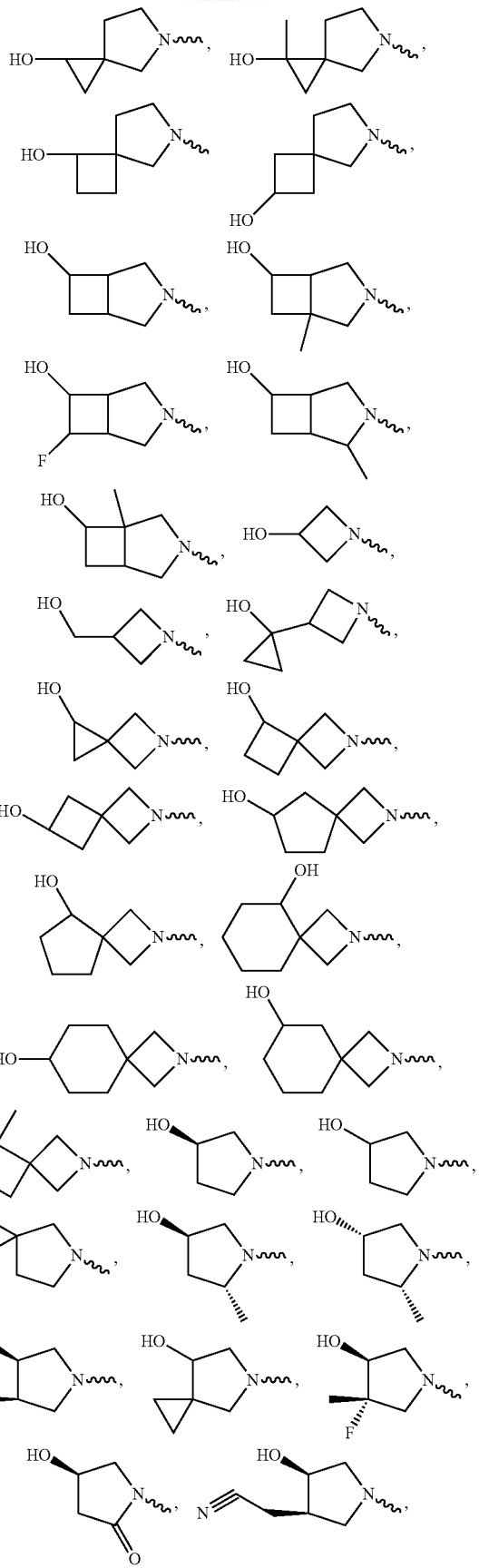

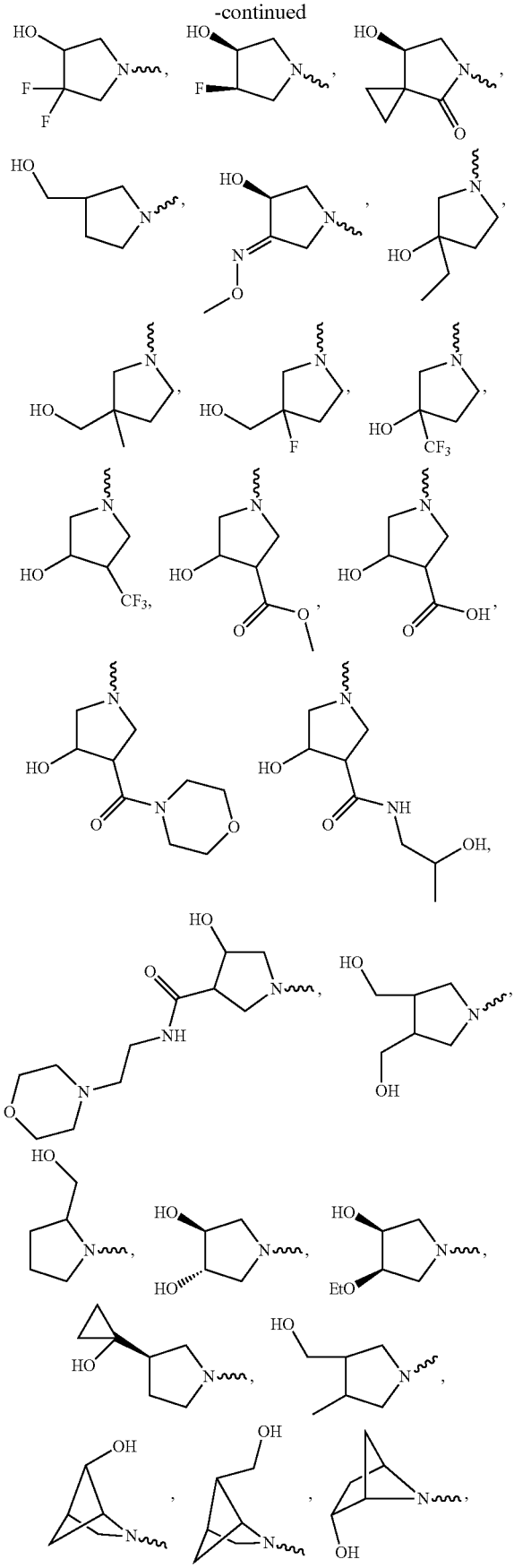
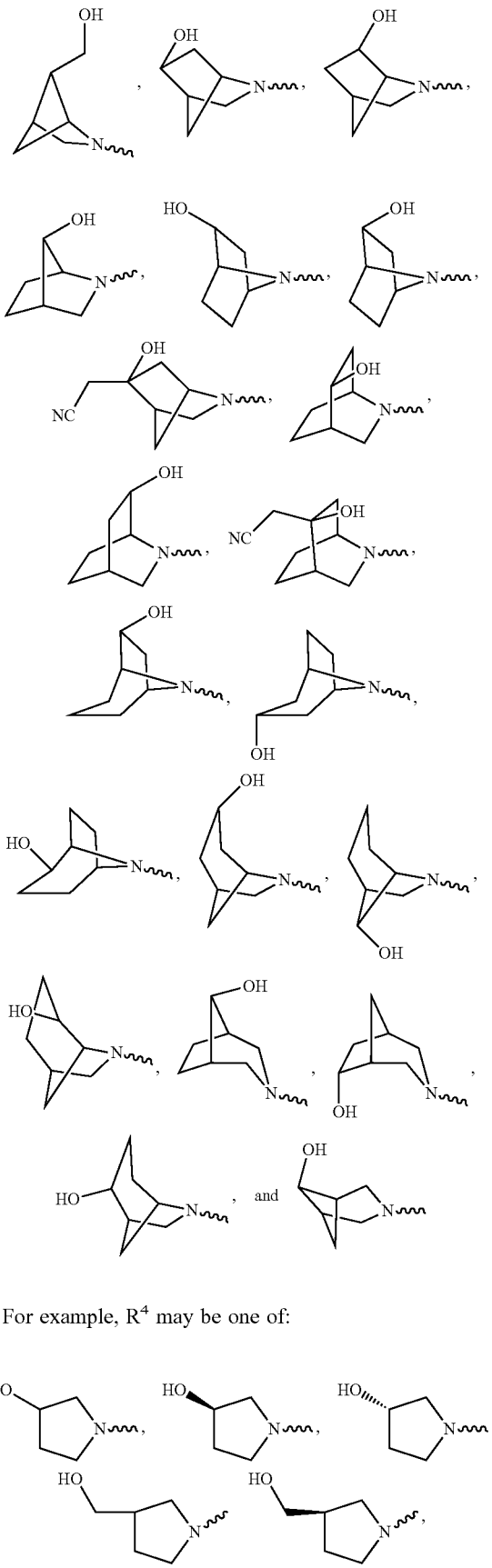
For example, $R^4$ may be one of:

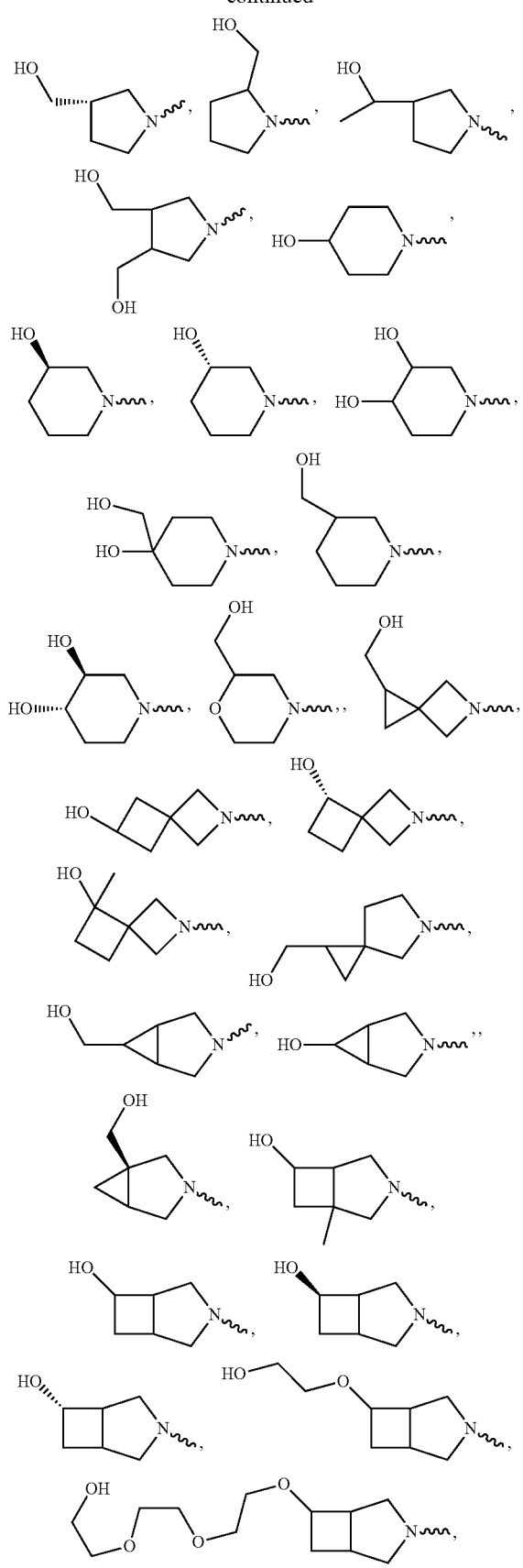

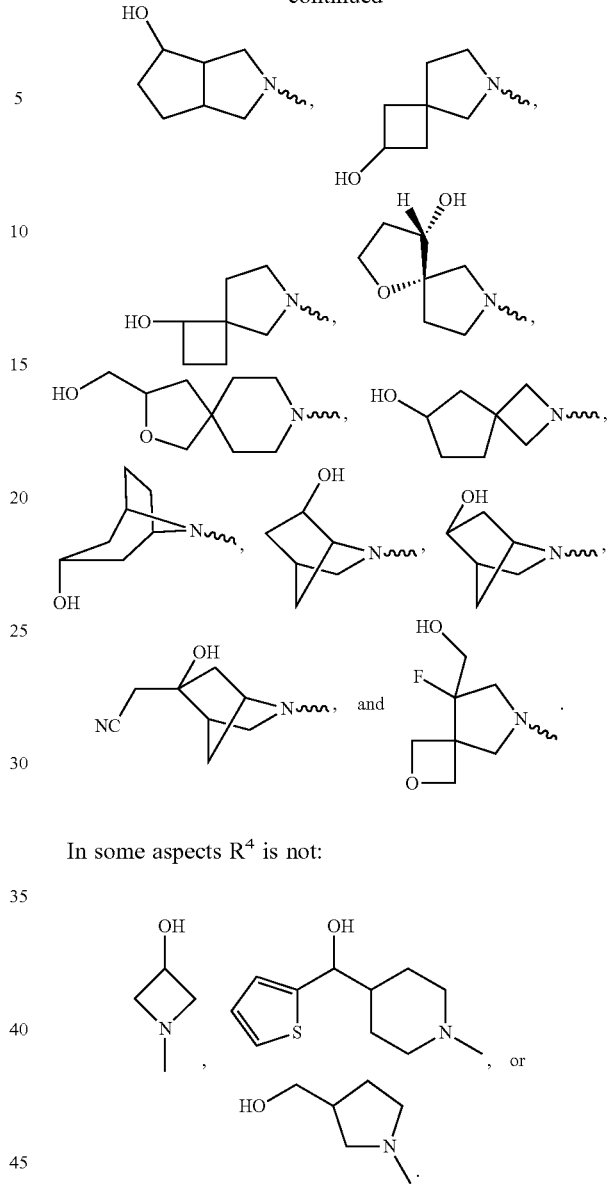

In some aspects R⁴ is not:

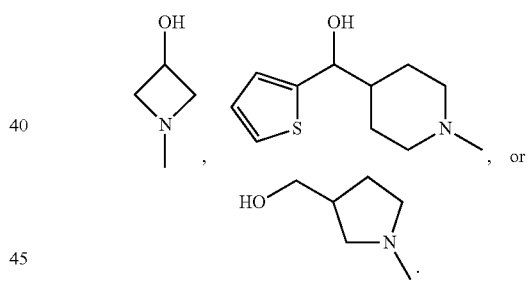

The compound may be one of the compounds exemplified in the Examples.

Prodrugs may also be prepared from the compounds of Formula I. The term "prodrug," as used herein, represents compounds which can be transformed in vivo to the active parent compounds defined herein.

In addition, prodrugs may have increased oral bioavailability compared to the parent drug. Although the benefits of prodrugs are widely recognized, often prodrugs fail to achieve these advantages. Thus, significant effort and research are needed to develop an effective prodrug.

The prodrugs herein may have less antibacterial activity than the parent antibacterial agent and, consequently, less disruptive to the digestive tract. Because these prodrugs are converted in blood to the active antibacterial agent, they are active systemically. Thus, the prodrug may maintain the beneficial effects of curing the bacterial infection while avoiding the significant side effects of the parent antibacterial agent on the gastrointestinal tract.

In addition, the prodrug may have increased the water solubility compared to the parent antibacterial agent, thereby enabling a better formulation for intravenous administration.

In some aspects, a prodrug may have the structure of Formula II:

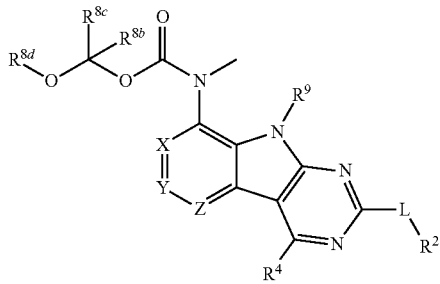

Formula II $R^2$, $R^4$, and $R^9$ are described herein.

The drug of Formula II maybe cleaved by an esterase in the blood and converted to the active antibacterial agent having the Formula I.

$R^{8b}$ or $R^{8c}$ may be each independently H or C1-C6 alkyl, for example, C1-C4 alkyl, such as methyl, ethyl, or tertiary butyl. For example, $R^{8b}$ may be methyl, $R^{8c}$ may be H; or $R^{8c}$ may be tertiary butyl and $R^{8c}$ may be H. In some instances, one of $R^{8b}$ or $R^{8c}$ is H, or both are H.

In some aspects, $R^{8d}$ is

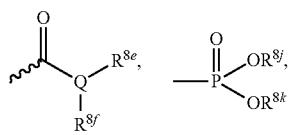

or a pharmaceutically acceptable salt thereof. Pharmaceutically acceptable salts are known in the art and include metal cations, for example a sodium, magnesium, calcium or potassium salt, and also include amine cations such as $NH_4^+$ or alkylated amines.

Q may be CH or N, such as CH.

$R^{8e}$ may be $(CR^{8g}_2)_n$-basic amine, wherein n is 0-2, such as 1, and wherein each $R^{8g}$ may be independently H or C1-C3 alkyl, such as $H_2$, $HCH_2$ or $CH_2CH_2$. Generally, a basic amine is a solubilizing group that increases the solubility of a drug or prodrug in aqueous environments such as blood upon administration to the subject.

The basic amine may be $NR^{8h}R^{8i}$ wherein $R^{8h}$ and $R^{8i}$ are independently selected from the group consisting of H, optionally substituted C1-C4 alkyl, wherein optional substituents may be OH, $NH_2$, or $NHCH_3$ wherein $R^{8h}$ and $R^{8i}$ may join to form a fused ring containing 1-3 N, or 0-3 O or S heteroatoms. For example, basic amines in the context of prodrugs may include piperzinyl, morpholinyl, C1-C2 alkyl amine such as methyl amine, C1-C2 dialkyl amine such as dimethylamine, or $NH_2$.

For example, $R^{8d}$ may be

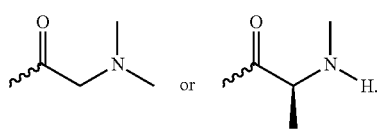

In some aspects, $R^{8f}$ is hydrogen or C1-C6 alkyl, such as methyl, ethyl, propyl, or iso-propyl, or a C1-C6 alkyl, such as methyl, ethyl, propyl, or iso-propyl, optionally substituted with OH or $NH_2$. For example, $R^{8f}$ may be $CH_2OH$, $CHOHCH_3$, or $(CH_2)_4NH_2$. $R^{8f}$ also may be methyl.

In addition, $R^{8e}$ and $R^{8f}$ may join to form a ring; for example, $R^{8d}$ may be

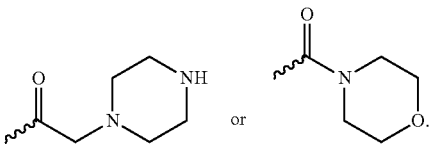

$R^{8e}$ may be

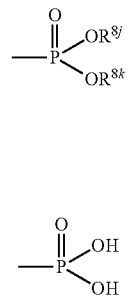

such as

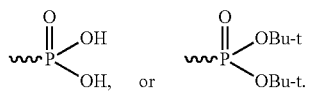

or a pharmaceutically acceptable salt thereof as described herein. $R^{8j}$ and $R^{8k}$ may be independently H, C1-C8 hydrocarbyl residue such as C1-C8 alkyl, for example tertiary butyl, or benzyl.

For example, in some aspects, $R^{8c}$ may be

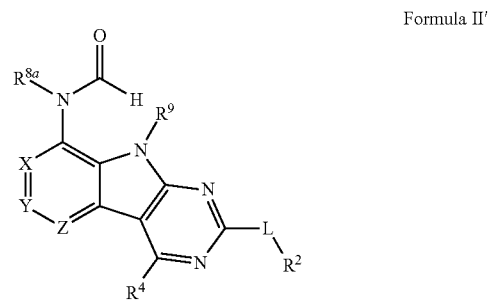

In some aspects, a prodrug may have the structure of Formula II':

Formula II' where the R groups are as defined herein.

Generally, more than one prodrug substituent may be present on the compound.

A prodrug also may have the structure of Formula IV or V:

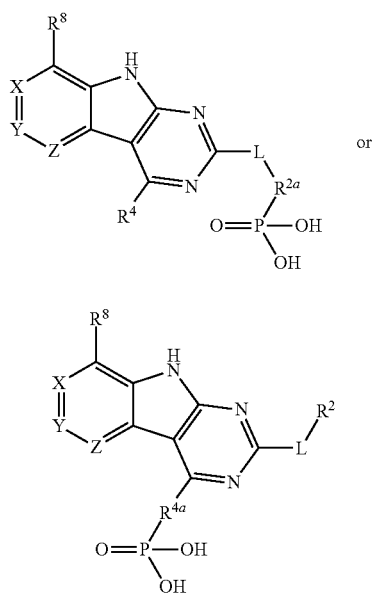

Formula IV

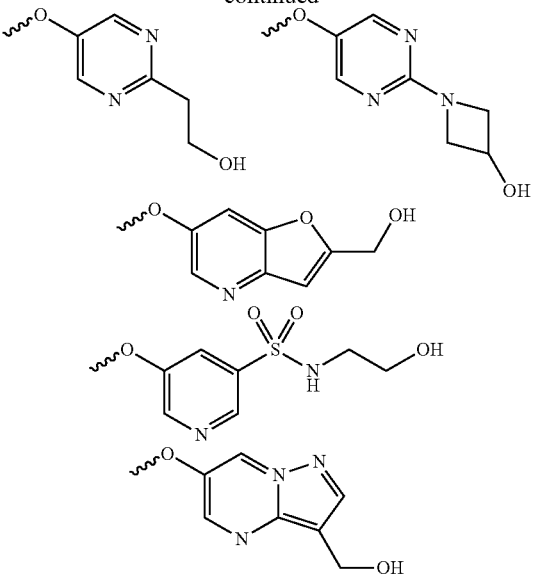

Formula V or a pharmaceutically acceptable salt thereof as described herein.

Any suitable $R^2$ herein comprising an OH group or substituted with an OH may allow phosphorylation to arrive at Formula IV. Thus, $R^{2a}$ contains an oxygen residue derived from an $R^2$ wherein $R^2$ has an OH group, wherein $R^2$'s OH is replaced with an oxygen residue in $R^{2a}$, upon phosphorylation, and wherein the oxygen residue is linked to P in the phosphate group.

Among others herein, examples of suitable $R^2$ groups include the following, which are shown below as attached to an O linker although other linkers may be used:

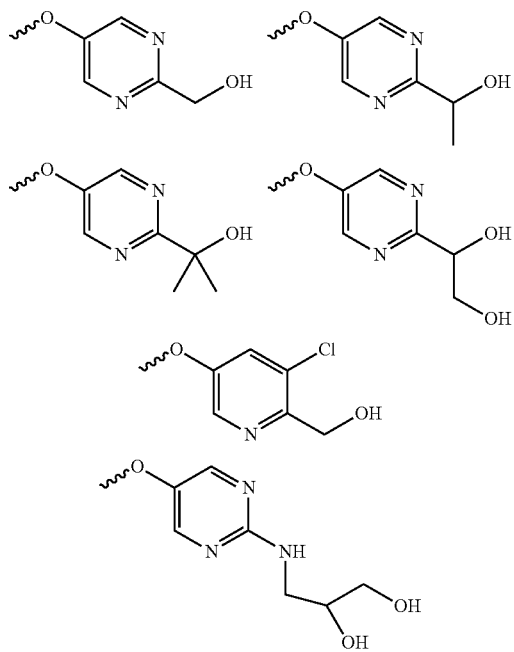

Any suitable $R^4$ herein comprising an OH group or substituted with an OH group may allow phosphorylation to arrive at Formula V. Thus, $R^{4a}$ contains an oxygen residue derived from a non-prodrug $R^4$. Thus, if the non-prodrug $R^4$ has an OH group, $R^4$'s OH is replaced with an oxygen residue in $R^{4a}$, upon phosphorylation, wherein the oxygen residue is linked to P in the phosphate group.

$R^2$ and $R^4$ substituents that are disclosed in PCT/US2012/029104, U.S. Prov. Pat. Appl. 61/700,159, or the PCT application that claims priority to U.S. Prov. Pat. Appl. 61/700,159, maybe further substituted with —OH as known in the art.

The prodrug of Formula IV or Formula V maybe cleaved by a phosphatase in the blood and converted to the active antibacterial agent having an $R^2$ or $R^4$ group respectively containing a hydroxy group. $R^{2a}$ or $R^{4a}$ may be derived from an active antibacterial compound having an hydroxy substituted $R^2$ or $R^4$ group respectively, wherein upon the formation of the prodrug, the hydroxy becomes the point of attachment to the phosphate.

When a prodrug formula, e.g. Formula II-V, includes an $R^2$, $R^4$, or $R^8$ group, any appropriate $R^2$, $R^4$, or $R^8$ group herein may be used.

A pharmaceutically-acceptable salt, ester, or prodrug of the compounds herein is also contemplated. Those skilled in the art will appreciate that a variety of prodrugs, salts, hydrates, solvates, and polymorphs can be produced from the compounds disclosed here, and that various isotopically-substituted variants (through, e.g., substitution of deuterium for hydrogen, $^{13}C$ for carbon, $^{15}N$ for nitrogen, or $^{32}P$ for phosphorus) known as "isotopomers" can also be readily produced. All such derivatives are contemplated within the scope of this disclosure.

Many of the compounds may be in the form of a salt. Those skilled in medicinal chemistry will appreciate that the choice of salt is not critical, and pharmaceutically-acceptable salts can be prepared by well-known methods. Handbook of Pharmaceutical Salts: Properties, Selection and Use. (P. Heinrich Stahl and Camille G. Wermuth, eds.) International Union of Pure and Applied Chemistry, Wiley-VCH 2002 and L. D. Bighley, S. M. Berge, D. C. Monkhouse, in "Encyclopedia of Pharmaceutical Technology'. Eds. J.

Swarbrick and J. C. Boylan, Vol. 13, Marcel Dekker, Inc., New York, Basel, Hong Kong 1995, pp. 453-499 discuss such salts in detail.

Compounds herein include those structures that are set out throughout the examples, and pharmaceutically acceptable salts, esters and prodrugs thereof. In some embodiments, the compound is in a pharmaceutical composition or a dosage form, wherein the pharmaceutical composition or dosage form provides an effective antibiotic amount of the compound for treating or preventing infection.

In another aspect, the present disclosure relates to a pharmaceutical composition comprising one or more physiologically acceptable surface active agents, additional carriers, diluents, excipients, smoothing agents, suspension agents, film forming substances, and coating assistants, or a combination thereof; and a composition disclosed herein. Acceptable additional carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" refers to a carrier or diluent that does not abrogate the biological activity and properties of the compound.

The pharmaceutical compounds described herein can be administered to a human patient per se, or in pharmaceutical compositions where they are mixed with other active ingredient(s), as in combination therapy, or suitable carriers or excipient(s). In some embodiments, a dosage form includes those forms in which the compound is administered per se. In addition, a dosage form may include a pharmaceutical composition. In any case, the dosage form may comprise a sufficient amount of the compound to treat a bacterial infection as part of a particular administration protocol, as would be understood by those of skill in the art. Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the composition can be formulated readily by combining the compositions of interest with pharmaceutically acceptable carriers well known in the art. Such carriers, which may be used in addition to the cationic polymeric carrier, enable the compositions to be formulated as tablets, pills, dragees, capsules, liquids, gels, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), e.g., Povidone. If desired, disintegrating agents may be added, such as the cross-linked polyvinylpyrrolidone (e.g. Crospovidone), agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner. Administration to the buccal mucosa and sublingually are contemplated.

For administration by inhalation, the composition can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Methods for treating bacterial infections may include administering a therapeutically effective amount of the therapeutic compounds as described herein. Treating a bacterial infection may also include prophylactically administering the therapeutic compounds to prevent infection or the spread of an infection in a subject at imminent risk of infection, such as a subject receiving or about to undergo surgery, an immunocompromised subject, or subject otherwise at risk of an infection if the compound was not administered. The compounds show inhibitory activity against a broad spectrum of bacteria including *H. influenzae, E. coli, S. aureus, E. faecalis, E. facium, K. pneumonia, A. baumannii, S. pneumoniae,* and *P. aeruginosa.* The compounds show activity against most resistant strains for example methicillin resistant *Staphylococcus aureus* (MRSA). In addition, the compounds show broad-spectrum activity against all Category A, B, and C bacterial biodefense pathogens including *B. anthracis, B. pseudomallei, B. mallei, F. tularensis* and *Y. psetis.* See the Examples. The compounds have excellent relative antibiotic activity with a relatively low concentration. Further, the compounds may exert potent antibacterial activity versus various human and animal pathogens, including Gram-positive and Gram-negative bacteria. In an embodiment, the bacterial infection that may be treated or ameliorated is MRSA.

Methods of treating bacterial infections also include intraabdominal infection, a urinary tract infection, or melioidosis. Intraabdominal infections include various infections such as peritonitis, appendicitis, abscesses, sepsis, and cholecystitis, which may be complicated or uncomplicated. The compound here in may also be used to treat urinary tract infections, which may be caused by *E. coli.* In addition, the compounds herein are useful to treat melioidosis, which may be caused by *B. pseudomallei.*

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Pharmaceutical compositions suitable for administration include compositions where the active ingredients are contained in an amount effective to achieve its intended purpose. In some embodiments, a therapeutically effective amount of a compound is an amount effective to treat a bacterial infection, for example, in a mammalian subject (e.g., a human). The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively the compositions may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

In some embodiments, in the pharmaceutical industry, it standard practice to provide substantially pure material when formulating pharmaceutical compositions. Therefore, in some embodiments, "substantially pure" refers to the amount of purity required for formulating pharmaceuticals, which may include, for example, a small amount of other material that will not affects the suitability for pharmaceutical use. In some embodiments, the substantially pure compound contains at least about 96% of the compound by weight, such as at least about 97%, 98%, 99%, or 100% of the compound.

The terms "approximately, "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

EXAMPLES

Synthesis methods for the starting materials, such as the bissulfone, are found in PCT/US2012/029104, U.S. Prov. Pat. Appl. 61/700,159, or the PCT application that claims priority to U.S. Prov. Pat. Appl. 61/700,159 (WO 2014/043272). The general procedure for the synthesis follows:

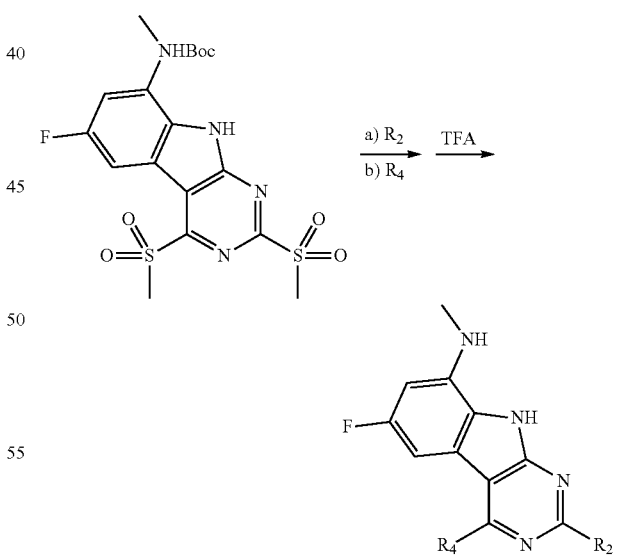

The bissulfone was first treated with $R^2$ and $K_2CO_3$, then following by addition of $R^4$ in one pot. The final product was obtained by Boc deprotection with TFA.

General experimental methods include the following:

1H NMR spectra were recorded on Bruker Avance III 400 MHz and Bruker Fourier 300 MHz and TMS was used as an internal standard.

LCMS was taken on a quadrupole Mass Spectrometer on Agilent LC/MSD 1200 Series (Column: ODS 2000 (50×4.6 mm, 5 μm) operating in ES (+) or (−) ionization mode; T=30° C.; flow rate=1.5 mL/min; detected wavelength: 214 nm.

Prep-HPLC was performed at conditions: (Flash: Welchrom C18, 150×20 mm); Wavelength 220 nm; Mobile phase: A MeCN (0.1% TFA); B water (0.1% TFA); Flow rate: 25 mL/min; Injection volume: 2 mL; Run time: 30 min; Equilibration: 5 min.

Example 1

Synthesis of $R^4$ Pieces

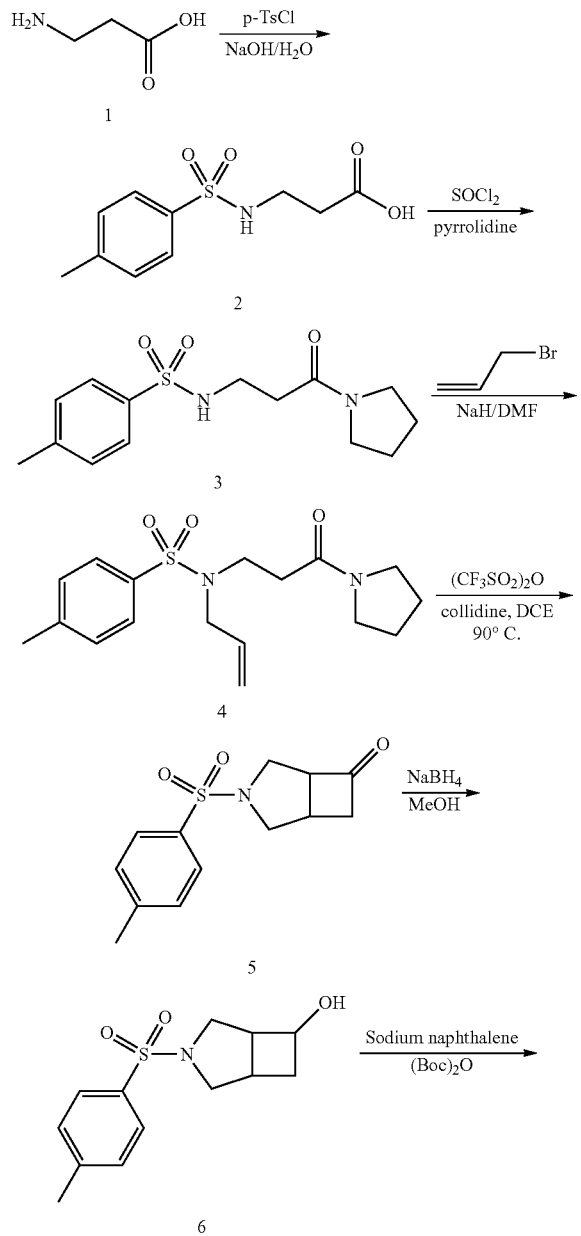

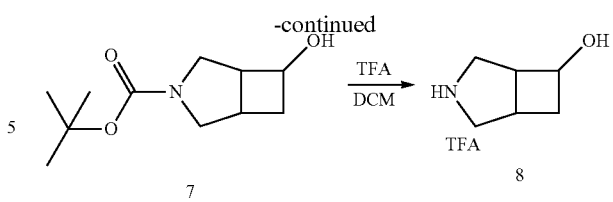

Synthesis of 3-{[(4-methylphenyl)sulfonyl]amino}propanoic acid (2)

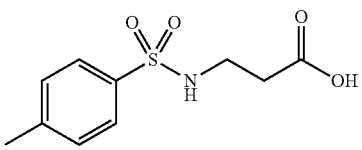 [SMILES: Cc1ccc(S(=O)(=O)NCCC(=O)O)cc1]

To a solution of (1) (45.0 g, 0.51 mol) and NaOH (40.4 g, 1.02 mol) in water (500 mL) was added chloro(4-methylphenyl)sulfone (96 g, 0.51 mol) drop wise at 70° C., then stirred at 70° C. for 1 h, then cooled. Acidification of the reaction mixture to pH=1 with concentrated HCl yielded the crude product as a thick precipitate. The product was isolated by filtration and re-crystallized from ethanol to give 90 g of compound 2 as white solid (Y=73%). $^1$H NMR (400 MHz, DMSO-$d_6$): δ 2.33-2.36 (m, 2H), 2.50-2.51 (m, 3H), 2.89-2.91 (d, J=6 Hz, 2H), 7.39-7.41 (d, J=8 Hz, 2H), 7.59 (s, 1H), 7.67-7.69 (d, J=8 Hz, 2H).

Synthesis of 3-{[(4-methylphenyl)sulfonyl]amino}-1-pyrrolidinylpropan-1-one (3)

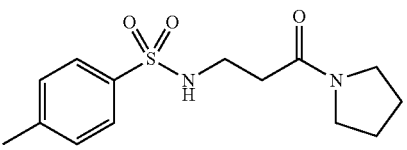 [SMILES: Cc1ccc(S(=O)(=O)NCCC(=O)N2CCCC2)cc1]

To a solution of (2) (90.0 g, 0.37 mol) in $SOCl_2$ (900 mL), stirred with refluxing for 2.5 h, then concentrated and residue was dissolved in DCM was added pyrrolidine (71.1 g, 0.99 mol) in DCM, then stirred at room temperature for 2 h. The reaction mixture was diluted with water and extracted with DCM (100 mL×3), washed with brine, dried over $Na_2SO_4$ and filtered, the filtrate was evaporated to remove the solvent. The residue was purified by on silica gel (DCM/MeOH=80/1) to give compound 3 (97 g, 88%) as white solid. $^1$H NMR (400 MHz, DMSO-$d_6$): δ 1.83-1.88 (m, 2H), 1.91-1.96 (m, 2H), 2.42 (s, 3H), 2.43-2.49 (t, 2H), 3.17-3.2 (m, 2H), 3.28-3.31 (t, 2H), 3.40-3.43 (t, 2H), 5.67-5.70 (t, 2H), 7.29-7.31 (d, J=8 Hz, 2H), 7.74-7.62 (d, J=8 Hz, 2H); MS Calcd.: 296; MS Found: 297 ([M+H]$^+$).

Synthesis of 3-{[(4-methylphenyl)sulfonyl]prop-2-enylamino}-1-pyrrolidinyl propan-1-one (4)

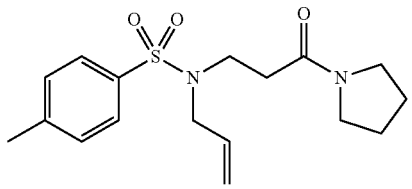 [SMILES: C=CCN(CCC(=O)N1CCCC1)S(=O)(=O)c1ccc(C)cc1]

To a solution of (3) (97.0 g, 0.33 mol) and (5) (59.4 g, 0.50 mol) in DMF (500 mL) was added sodium hydride (60% w/t in mineral oil, 19.8 mg, 0.50 mol) at 0° C., then stirred at 95° C. for 3.5 h. The reaction mixture was diluted with water and extracted with DCM (100 mL×3), washed with brine, dried over $Na_2SO_4$ and filtered, the filtrate was evaporated to remove the solvent. The residue was purified by on silica gel (DCM/MeOH=120/1) to give compound (6) (35 g, 31%) as light-yellow oil. $^1$H NMR (400 MHz, $CDCl_3$): δ 1.82-1.88 (m, 2H), 1.92-1.99 (m, 2H), 2.43 (s, 3H), 2.63-2.67 (t, 2H), 3.39-3.44 (m, 6H), 3.82-3.83 (d, J=6.4 Hz, 2H), 5.12-5.20 (m, 2H), 5.60-5.70 (m, 1H), 7.29-7.32 (d, J=8 Hz, 2H), 7.69-7.71 (d, J=8.4 Hz, 2H); MS Calcd.: 336; MS Found: 337 ([M+H]$^+$).

Synthesis of 3-[(4-methylphenyl)sulfonyl]-3-azabicyclo[3.2.0]heptan-6-one (5)

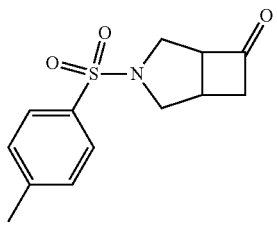 [SMILES: Cc1ccc(S(=O)(=O)N2CC3CC(=O)C3C2)cc1]

A solution of 6 (35 g, 0.10 mol) in 1,2-dichloroethane (250 mL) is added over 20 min to a solution of triflicanhydride (58 g, 0.20 mol) in 1,2-dichloroethane (100 mL). A solution of collidine (19 g, 0.15 mol) in 1,2-dichloroethane (100 mL) is then added slowly over 30 min. After the reaction mixture was heated at 90° C. for 2 h. After cooling to room temperature, the reaction mixture is concentrated. The residue is hydrolyzed in two phase system $H_2O$—$CCl_4$. The organic layers were dried over $Na_2SO_4$ and filtered, the filtrate was evaporated to remove the solvent. The residue was purified by on silica gel (PE/EA=10/1) to give compound 7 (15 g, 54%) as white solid. $^1$H NMR (400 MHz, $CDCl_3$): δ 2.45 (s, 3H), 2.67-2.72 (m, 1H), 2.85-2.92 (m, 1H), 2.94-3.00 (m, 2H), 3.27-3.35 (m, 1H), 3.59-3.66 (m, 2H), 3.17-3.12 (m, 2H), 3.83-3.86 (d, J=10 Hz, 1H), 7.34-7.36 (d, J=8 Hz, 2H), 7.69-7.71 (d, J=8.4 Hz, 2H); MS Calcd.: 265; MS Found: 266 ([M+H]$^+$).

Synthesis of 3-[(4-methylphenyl)sulfonyl]-3-azabicyclo[3.2.0]heptan-6-ol (6)

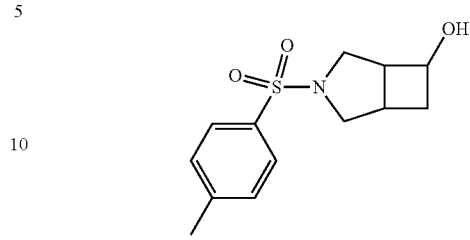

A solution of (7) (15 g, 0.1 mol) in MeOH (150 mL) was added $NaBH_4$ (4.29 g, 0.2 mol) in portion at ice-bath, after the reaction mixture was stirred 45 min at R.T. The reaction mixture was quenched with water, extracted with EA (50 mL×3), the combined organic layers were dried over $Na_2SO_4$, concentrated and purified by column chromatography on silica gel (PE:EA=8:1-4:1) to give compound 8 (14 g, 92%) as white solid. $^1$H NMR (400 MHz, $CDCl_3$): δ 1.73-1.79 (m, 1H), 2.12-2.14 (m, 1H), 2.44 (s, 3H), 2.52-2.63 (m, 3H), 2.67-2.75 (m, 1H), 2.96-3.01 (m, 1H), 3.42-3.43 (d, J=4 Hz, 1H), 3.86-3.88 (d, J=10.8 Hz, 1H), 4.23-4.25 (m, 1H), 7.34-7.36 (d, J=8.4 Hz, 2H), 7.72-7.74 (d, J=8.4 Hz, 1H); MS Calcd.: 267; MS Found: 268 ([M+H]$^+$).

Synthesis of tert-butyl 6-hydroxy-3-azabicyclo[3.2.0]heptane-3-carboxylate (7)

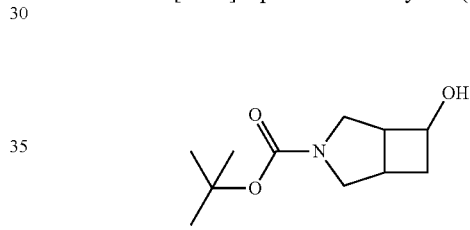

A solution of naphthalene (26.8 g, 0.2 mol) in dimethoxyethane (100 mL) was added sodium (4.2 mg, 0.2 mmol), and stirring the resulting dark green mixture for 3 hours. The compound of 8 (14 g, 0.05 mol) in dimethoxyethane (50 mL) at −60° C. was treated slowly with the sodium naphtalenide solution until a light green color persisted. The reaction mixture was then quenched at −78° C., by the addition of water. The mixture was allowed to warm to 0° C., and di-tert-butyl dicarbonate was added. After 3 hours the mixture was diluted with EA, extracted with EA (50 mL×3), washed with brine, the combined organic layers were dried over $Na_2SO_4$, concentrated and purified by column chromatography on silica gel (PE:EA=8:1-4:1) to give compound 9 (7 g, 63%) as colorless oil. $^1$H NMR (400 MHz, $CDCl_3$): δ 1.48 (s, 9H), 1.59-1.61 (m, 1H), 2.46-2.53 (m, 1H), 2.56-2.64 (m, 1H), 3.02-3.23 (m, 3H), 3.45-3.48 (m, 1H), 4.00-4.03 (m, 1H), 4.25-4.28 (t, 1H); MS Calcd.: 213; MS Found: 113[M$^+$+1-Boc].

Synthesis of 3-azabicyclo[3.2.0]heptan-6-ol (8)

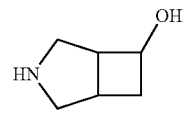

A solution of (7) (10 g, 0.1 mol) in DCM (150 mL) was added TFA (4.29 g, 0.2 mol) in portion at ice-bath, after the reaction mixture was stirred 45 min at R.T. The reaction mixture was concentrated and used for the next step of the reaction.

Example 2

Synthesis of Compounds white solid (85%, overall 63% from 1). LC-MS: M+1: 436.24. $^1$H NMR (300 MHz, DMSO) δ (ppm): 11.66 (s, 1H), 8.72 (s, 2H), 7.15 (d, J=11.2, 1H), 6.29 (d, J=9.7, 1H), 5.55 (br s, 1H), 5.11 (s, 1H), 4.64 (d, J=9.9, 1H), 4.20 (d, J=7.6, 1H), 4.03 (d, J=12.3, 1H), 3.60 (m, 2H), 3.12 (b m, 1H), 2.85 (s, 3H), 2.67 (s, 3H), 1.48 (m, 1H).

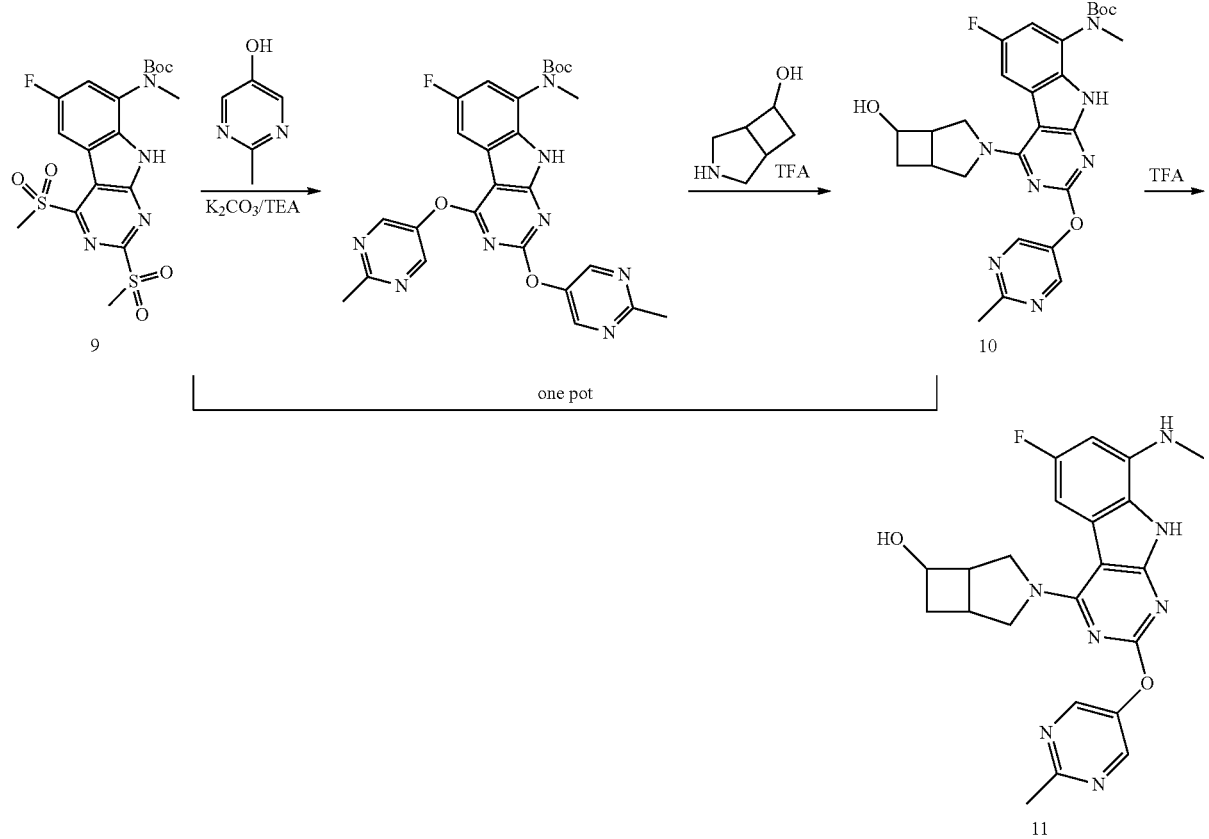

The bis-sulfone 9 (11.80 g, 17.23 mmol) was dissolved in NMP (60 mL), followed by adding 2-methylpyrimidin-5-ol 1 (7.59 g, 68.93 mmol). The homogeneous solution was obtained. K$_2$CO$_3$ (9.53 g, 68.93 mmol) was added and the resulting suspension was heated to 100° C. for 1 hr, then alcohol amine (7.32 g, 34.46 mmol) was added and the resulting mixture was heated to 100° C. for one more hour, cooled to the room temperature and water (450 mL) was poured into the mixture with stirring. The mixture was cooled to 0° C., filtered and washed the precipitates with water (2×25 mL), dried to give about 12 g of the white solid crude product. The crude solid was dissolved in dichloromethane and silica gel was added. Solvents were removed. Flash chromatography of the residue over silica gel (EtOAc/hexane: 20% to 50% to 90%) to give the pure 10 as a white solid (7.76 g, 75%). LC-MS: M+1: 536.30.

The compound 10 was dissolved in 50 mL of TFA and stirred for 1 minute at room temperature. After removal of the solvent, water (50 mL) and EtOH (25 mL) was added. The homogeneous solution was neutralized with 1N NaOH (about 150 mL, PH >10). The gummy solid was formed and separated. The gummy solid was suspended in water (50 mL) and broke the gummy solid into small pieces with spatula. The precipitates were filtered, washed with water twice and dried in the air to give 4.40 gram pure 11 as a light Scheme:

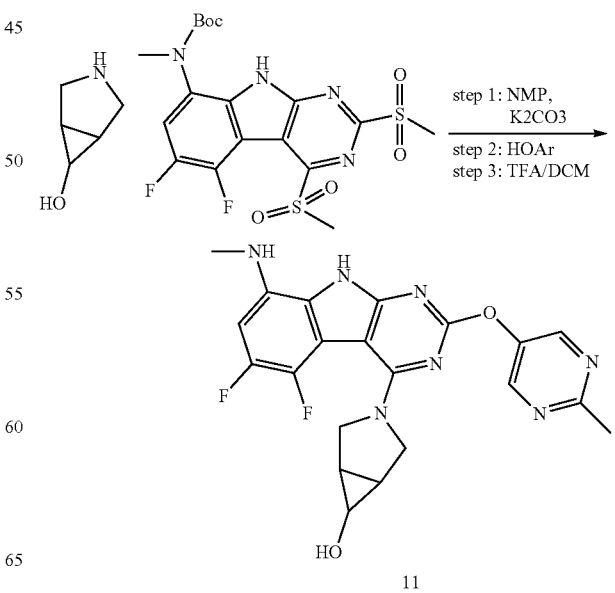

The mixture of 3-azabicyclo[3.1.0]hexan-6-ol (10 mg, 0.1 mmol), bissulfone (50 mg, 0.1 mmol), and K$_2$CO$_3$ (40 mg, 0.3 mmol) in NMP (2 mL) was stirred for overnight at room temperature, then 2-methylpyrimidin-5-ol (330 mg, 3 mmol) was added and the resulting mixture was heated to 80° C. for overnight. The crude product was purified by HPLC to give compound as a white solid (15 g, 35%). LC-MS: M+1: 540.

The above compound (10 mg, 0.02 mmol) was dissolved in 1 mL of TFA and stirred for 1 minute at room temperature. After removal of the solvents, the residue was purified by hPLC to provide final compound (6 mg, 68%). LC-MS: M+1: 440.

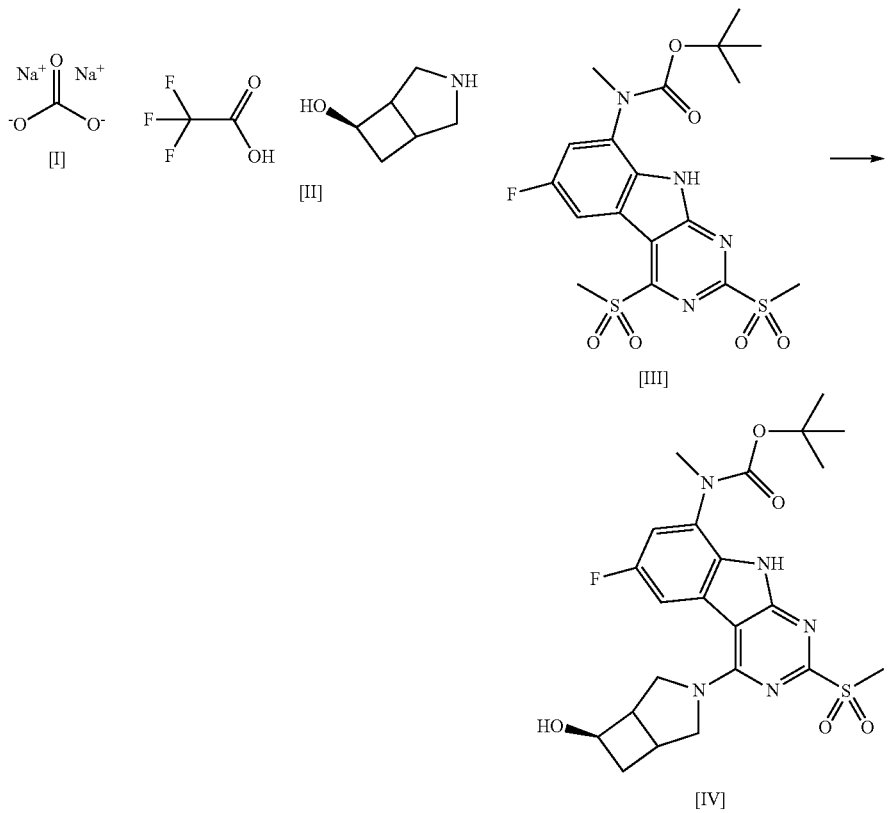

SM III (198 mgs, 0.419 mmol) and II (95 mgs, 1.0 eq) were dissolved in 1 mL of NMP. To this was added Na2CO3 (133 mgs, 3 eq). The resulting mixture was stirred at rt over 5 hrs. The reaction mixture was added water and was extracted with ethyl acetate three times. The organic layer was collected, combined and concentrated to an oil. Normal phase ISCO isolated desired product as a yellow semi-solids (71%). LC-MS: M+1: 506.

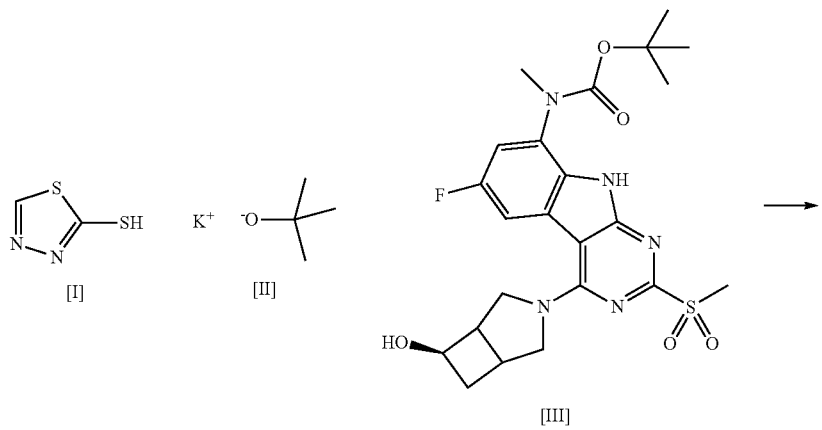

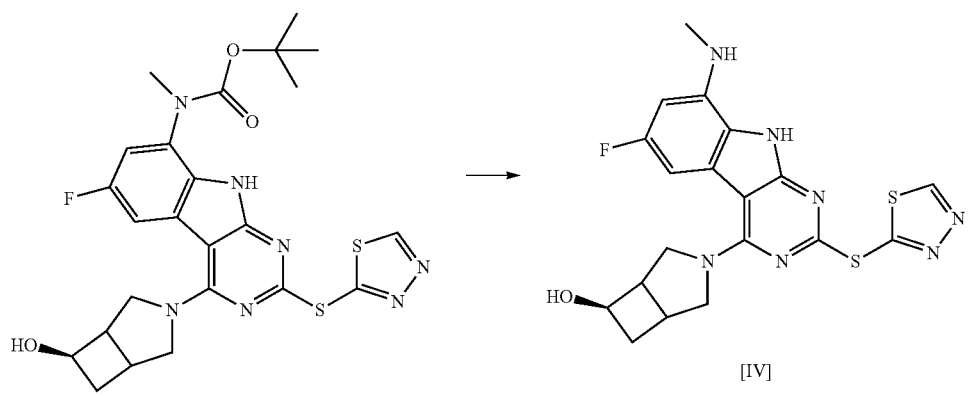

SM III (50 mgs, 0.1 mmol) and I (58 mgs, 5.0 eq) were dissolved in 0.5 mL of DMF. To this was added KOtBu (55 mgs, 5 eq). The resulting mixture was heated at 150° C. for 5 hrs. The reaction mixture was added water and was extracted with ethyl acetate three times. The organic layer was collected, combined and concentrated to an oil. Reverse phase ISCO isolated desired product as a off-white solids (40%). About 25 mgs of SM III was recovered. The dried product from this reaction was added 4 N HCl in dioxane (0.5 mL) and was stirred for 30 mins. After concentration, the residue was purified by reverse phase ISCO to give desired product as white solids (5 mg, 11%). LC-MS: M+1: 444.

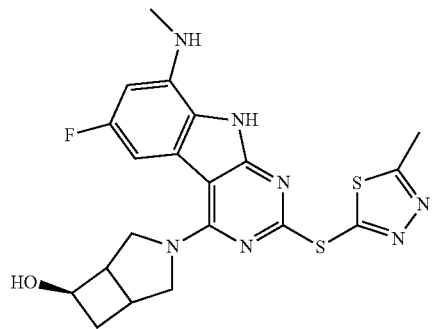

The above two compounds were synthesized using the same procedures as above.

Example 3

Synthesis of Compounds with N-linker

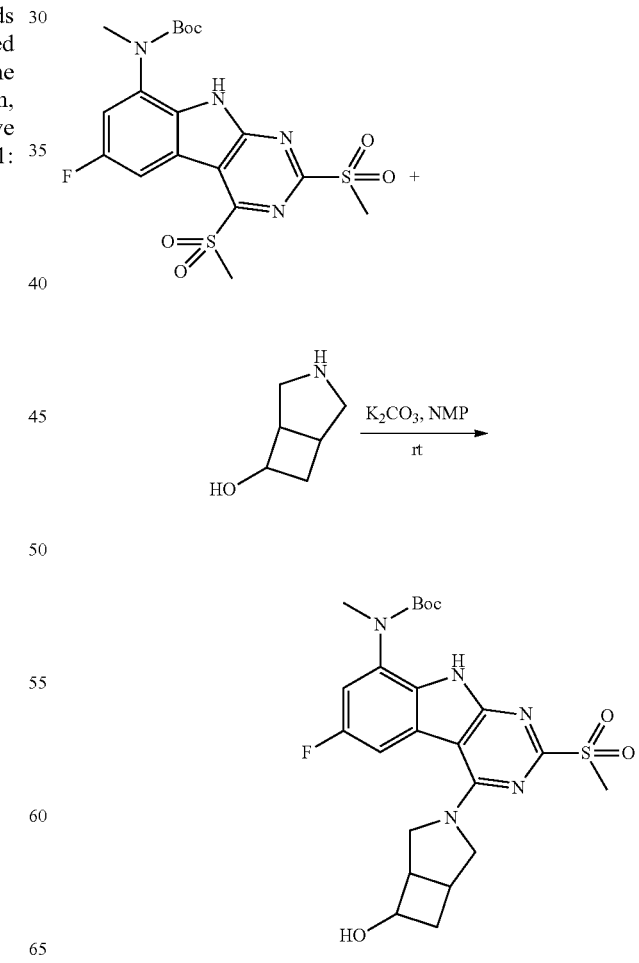

45 tert-butyl(6-fluoro-4-(6-hydroxy-3-azabicyclo[3.2.0]heptan-3-yl)-2-(methylsulfonyl)-9H-pyrimido[4,5-b]indol-8-yl)(methyl)carbamate The mixture of bis-sulfone (1.0 g, 2.12 mmol), amine (448.7 mg, 2.12 mmol) and K$_2$CO$_3$ (292.3 mg, 2.12 mmol) in NMP (7 mL) was stirred for 24 hours at room temperature. LC/MS indicated the completed reaction. Water (200 mL) was added to the mixture, and the resulting precipitate was filtered, washed with water (2×15 mL) and dried. 0.8 g of powder product was obtained (yield: 80%). MS (ESI) m/z 506 (M+H)$^+$.

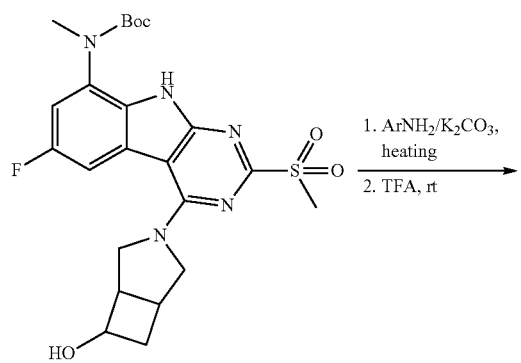

46

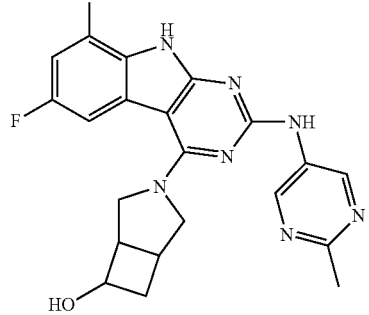

3-(6-fluoro-8-(methylamino)-2-((2-methylpyrimidin-5-yl)amino)-9H-pyrimido[4,5-b]indol-4-yl)-3-azabicyclo[3.2.0]heptan-6-ol The mixture of mono-sufone (50.6 mg, 0.1 mmol), 2-methylpyrimidin-5-amine (109 mg, 1.0 mmol), and K$_2$CO$_3$ (138.1 mg, 1.0 mmol) in NMP (0.5 mL) was heated to 140 C for 17 hrs, cooled to room temperature, and TFA (15 mL) was added and stirred for 5 minutes. After removal of the solvent, prep-HPLC of the residue gave the desired product. MS (ESI) m/z 435 (M+H)$^+$.

Example 4

Synthesis of Compound where Z and R$^4$ are Joined

General Scheme:

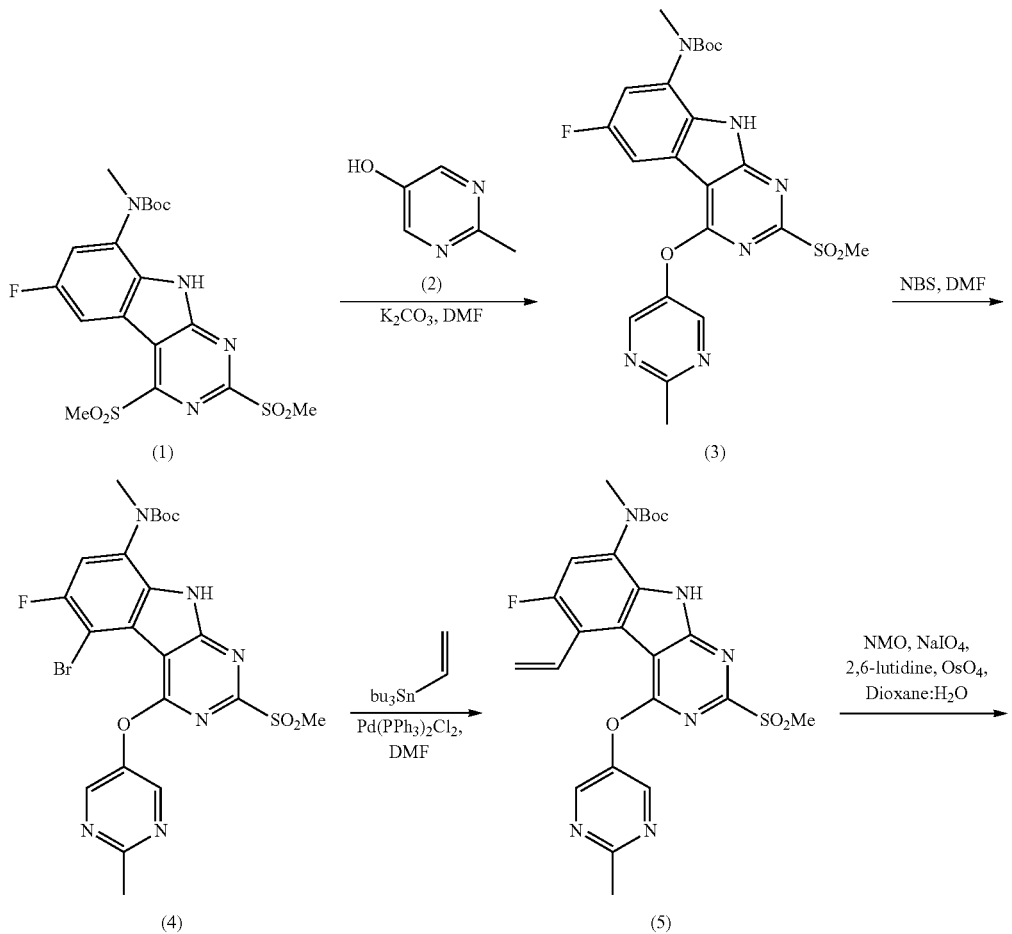

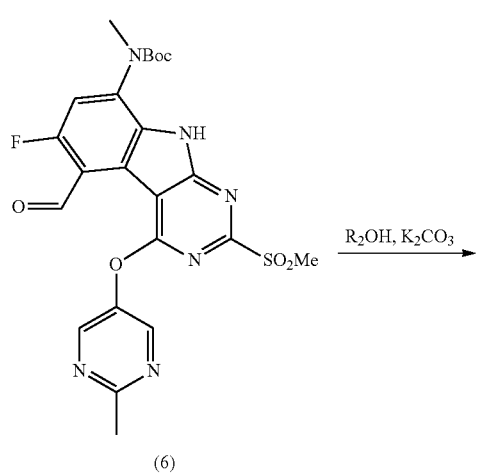

(6)

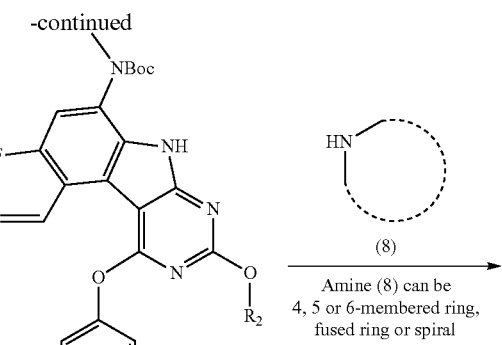

(7)

Amine (8) can be 4, 5 or 6-membered ring, fused ring or spiral

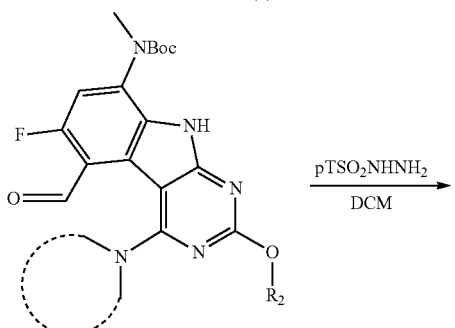

(9)

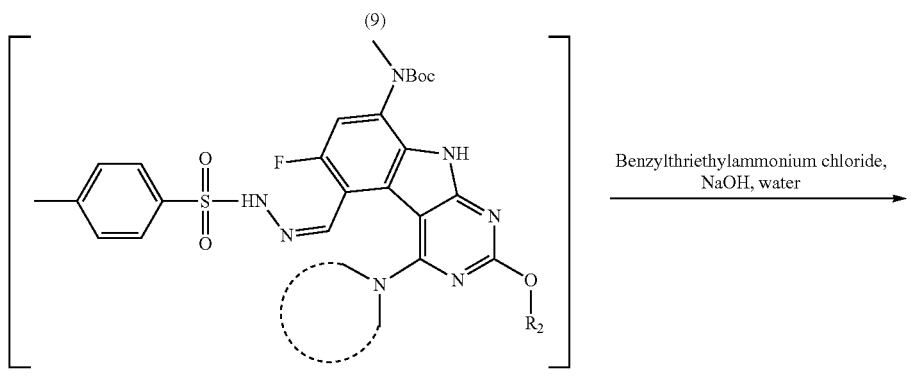

(10)

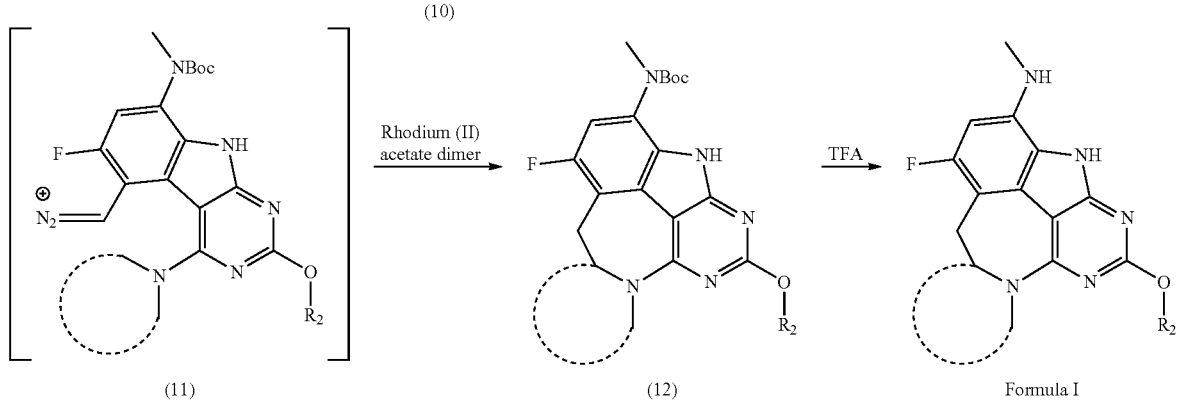

(11) (12) Formula I

Intermediate bis-methylsulfonyl 1 was used as starting material to prepare Formula I compounds. The $R_4$ methylsulfonyl of 1 was selectively replaced by 2-methylpyrimidin-5-ol in the presence of potassium carbonate at room temperature to afford product 3. Regioselective bromination of 3 by NBS was then carried out at 40° C. in DMF giving rise compound 4, which was then converted to the vinyl compound 5 by Stille coupling. Dihydroxylation in situ followed by oxidative cleavage of 5 directly provided aldehyde 6. Different R₂ fragments can be then installed at this stage of the synthesis. Typically, an OR₂ can replace the R₂ methylsulfonyl of compound 6 by heating the reaction at 90° C. in the presence of base. When R₂ was different from R₄ 2-methylpyrimidin-5-ol, more than 3 equivalences of R₂OH were used to minmize the bis-methylpyrimidine product. The product 7 of the substitution was then treated with amine 8 to convert into 9. Temperature of the reaction varied from room temperature to 80° C. depended on the reactivity of amine 8. Cyclic compound 12 was prepared from 9 via C—H carbene insertion through in situ three-step sequence of imination of 9, formation of diazonium 11, and the insertion of 11 to form 12. The Boc protecting group of compound 12 was then removed by TFA at room temperature to afford Formula I compound.

Example 4a

Synthesis of

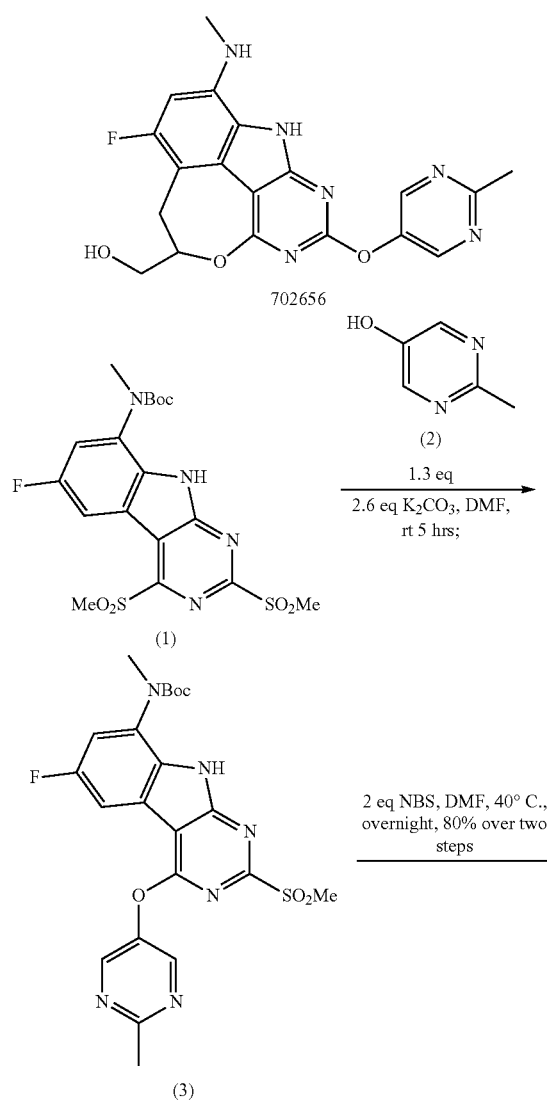

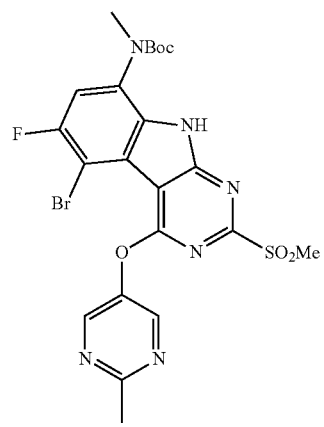

Compound 3. To the mixture of compound 1 (14.18 g, 30 mmol) and 2-methylpyrimidin-5-ol (4.29 g, 39 mmol) in anhydrous DMF (30 ml) was added K₂CO₃ (10.8 g, 78 mmol). The resulting was stirred at rt for 7 hours. It was then diluted with EtOAc (100 ml) and water (100 ml). The aqueous layer was extracted and back-extracted with EtOAc (100 ml×2). The combined organic layers were dried over Na₂SO₄ and concentrated by rotary evaporation at 40° C. Possibly trace amount of EtOAc was further dried off through co-evaporation with dichloromethane in vacuo. The crude sticky product (17.2 g) was carried to the next step without further purification. LC-MS: M+1: 503.5

Compound 4. To the solution of crude compound 3 in anhydrous DMF (30 ml) at 40° C. was added NBS (5.34 g, 30 mmol). The mixture was heated at 40° C. for 2 hours, and an additional amount of NBS (5.34 g, 30 mmol) was added. The reaction was continued at 40° C. overnight. It was then purified through silica gel column chromatography (40-60% EtOAc in hexane). About half of the total volume of the combined fractions were removed by rotory evaporation. The remaining solution was then washed with water (3×100 ml), dried over Na₂SO₄, and concentrated by rotory evaporation at 45° C. to afford the title compound as yellow solid (13.95 g, 80%). LC-MS: M+1: 582.3

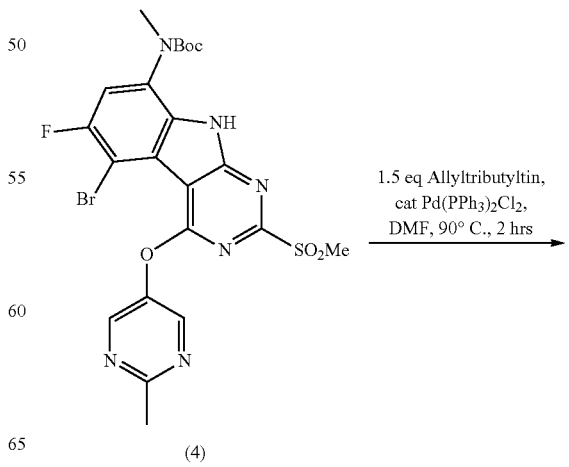

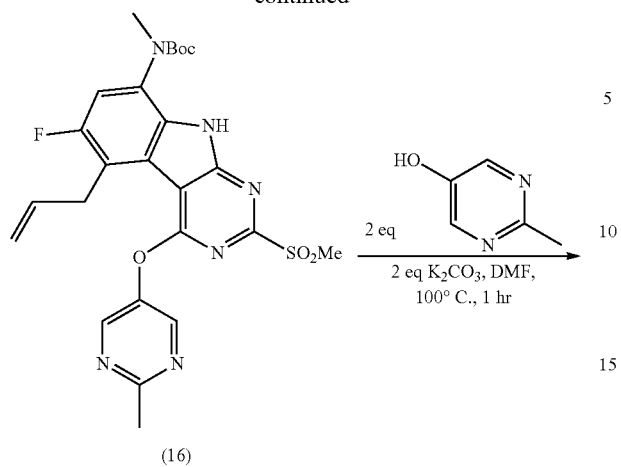

(16)

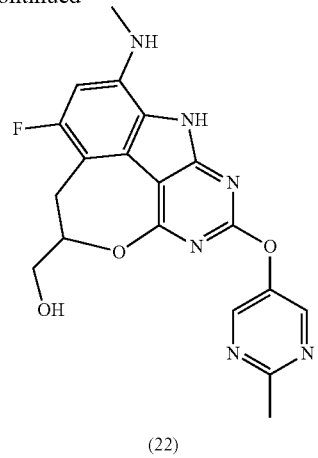

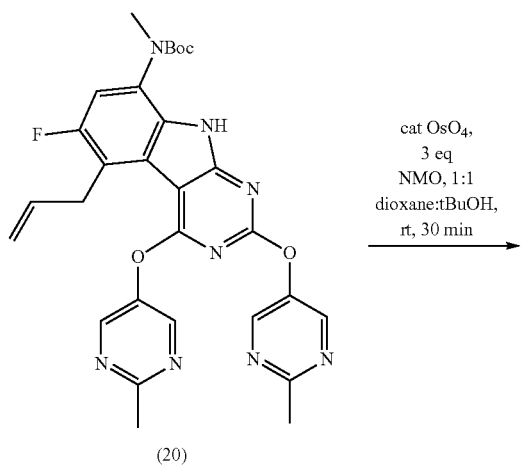

(20)

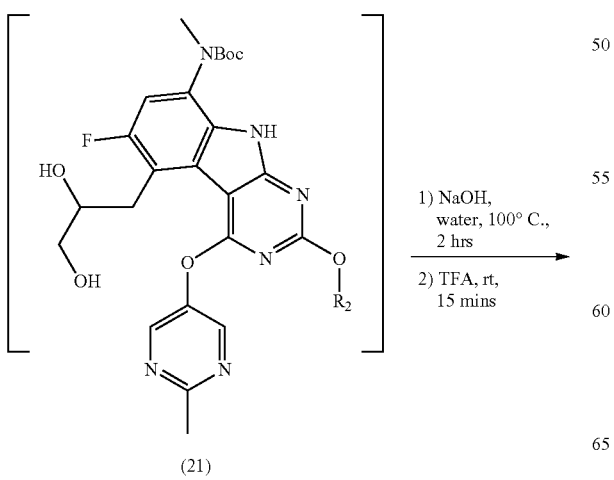

(21)

-continued

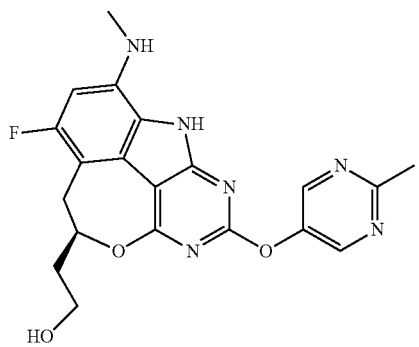

(22)

Compound 16: Compound 4 (1.16 g, 2 mmol) in anhydrous DMF (6 ml) was heated at 90° C. and the atmosphere was replaced with nitrogen. Allyltributylstannane (993 mg, 3 mmol) was added followed by the addition of catalytic amount of $Pd(PPh_3)_2Cl_2$ (140 mg, 0.2 mmol). The resulting mixture was heated under nitrogen for 2 hours. It was cooled down and purified through silica gel column chromatography (60-80% EtOAc in hexane). About half of volume of the combined fractions of the product were partially concentrated by rotory evaporation. It was then washed with water (3×70 ml), dried over $Na_2SO_4$, and concentrated by rotory evaporation at 45° C. to afford the title compound as yellow solid (998.4 mg, 92%). LC-MS: M+1: 543.6.

Compound 20: Mixture of compound 16 (813.9 mg, 1.5 mmol), 2-methylpyrimidin-5-ol (330.3 mg, 3 mmol) and $K_2CO_3$ (967.4 mg, 7 mmol) in anhydrous DMF (2 ml) was heated at 100° C. for 1 hour. The reaction mixture was cooled to rt and purified by C18 column chromatography to afford the title product as yellow solid (773 mg, 90%). LC-MS: M+1: 573.6.

Compound 22: Mixture of compound 20 (57 mg, 0.1 mmol) and N-methylmorpholine-N-oxide (35 mg, 0.3 mmol) was dissolved in 1:1 mixture of dioxane:tBuOH (1 ml). Catalytic amount of 4% aqueous solution of $OsO_4$ (2 drops) was then added, and the resulting mixture was stirred at rt for 30 minutes. After water (~0.5 ml) and sodium sulfite (50 mg) were added and stirred at rt to quench the excess oxidizing reagents, the reaction mixture was refluxed at 100° C. for 2 hours in the presence of 10% NaOH solution (1 ml). The product was purified through HPLC and treated with TFA (~0.3 ml) to afford the title compound as pink solid (15.8 mg, 40%). LC-MS: M+1: 397.1.

Example 4b

Synthesis of

53
-continued
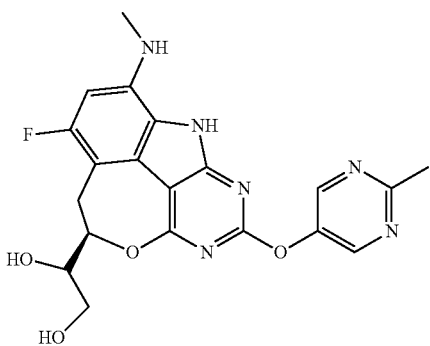
and analogs with other R².
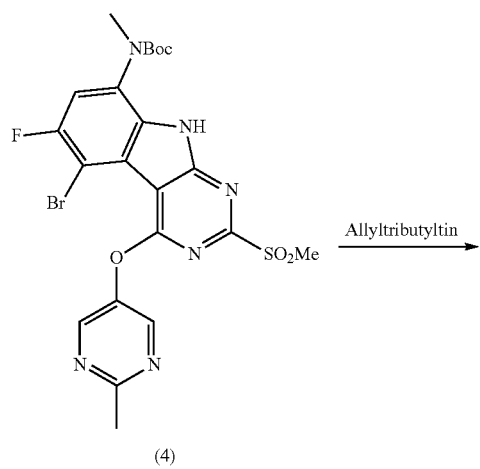
(4)
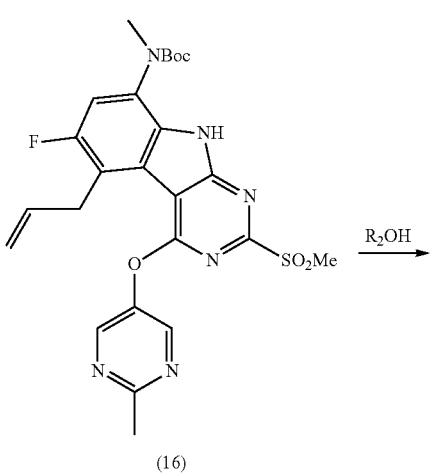
(16)
54
-continued
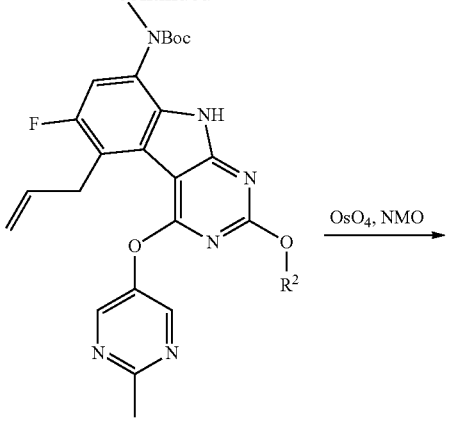
(17)
Intermediate 4 was used to prepare Example 4b compounds. The compound was first converted into the corresponding allyl 16 by Stille coupling. The R² methylsulfonyl of 16 was then substituted by an OR² in the presence of potassium carbonate at 100° C. to afford product 17.
Example 4c
Synthesis of
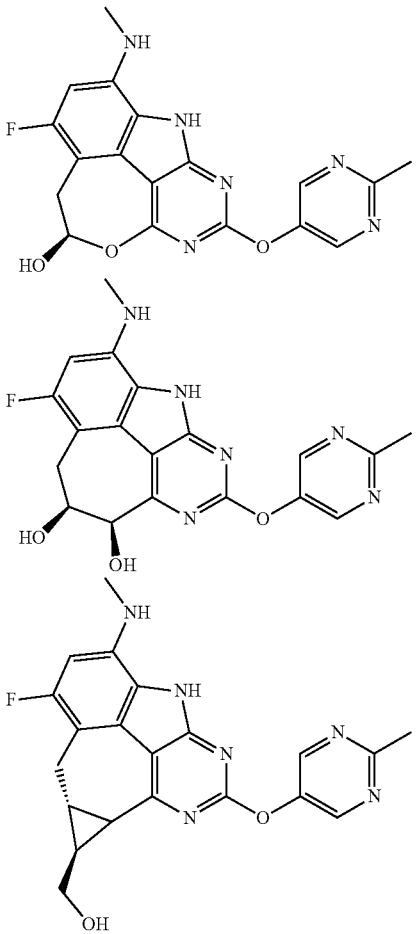

55
-continued
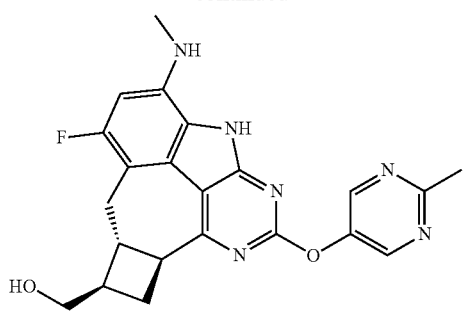
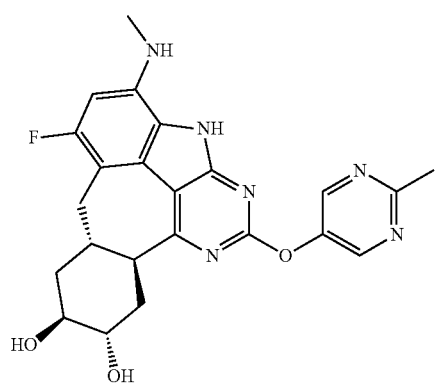
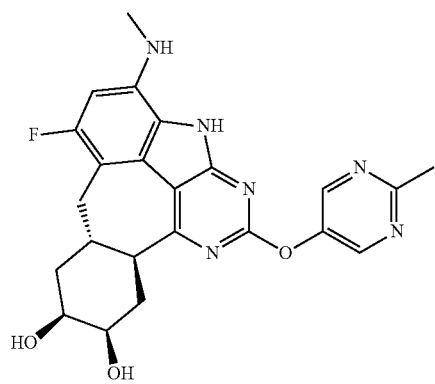
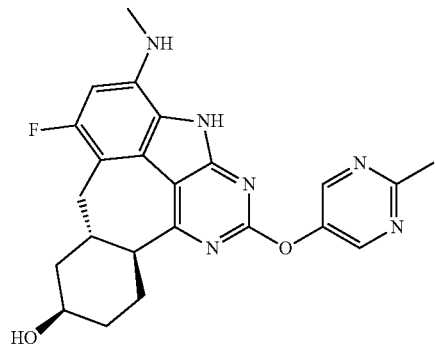
56
-continued
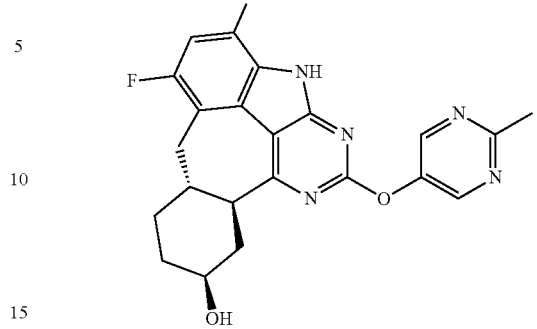
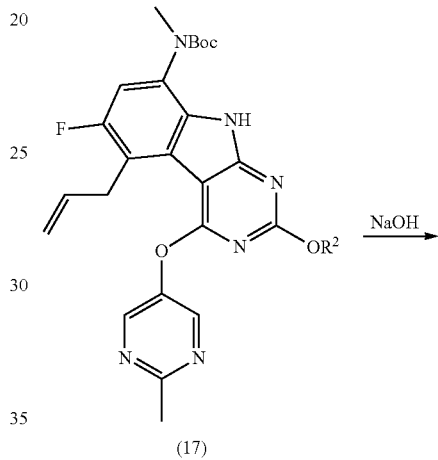
(17)
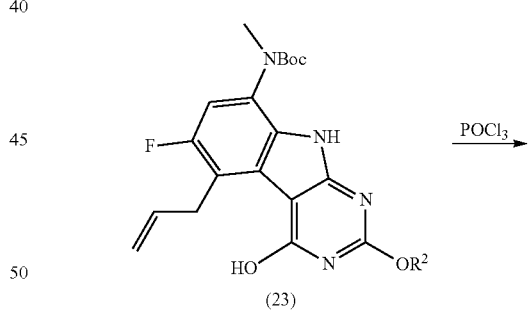
(23)
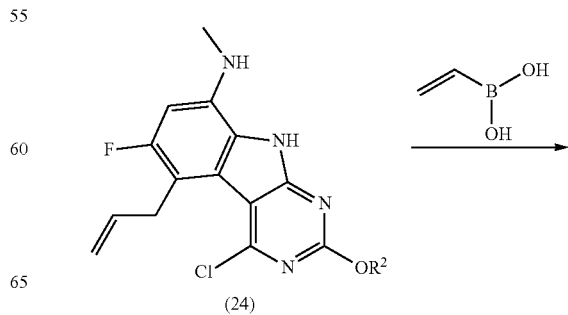
(24)

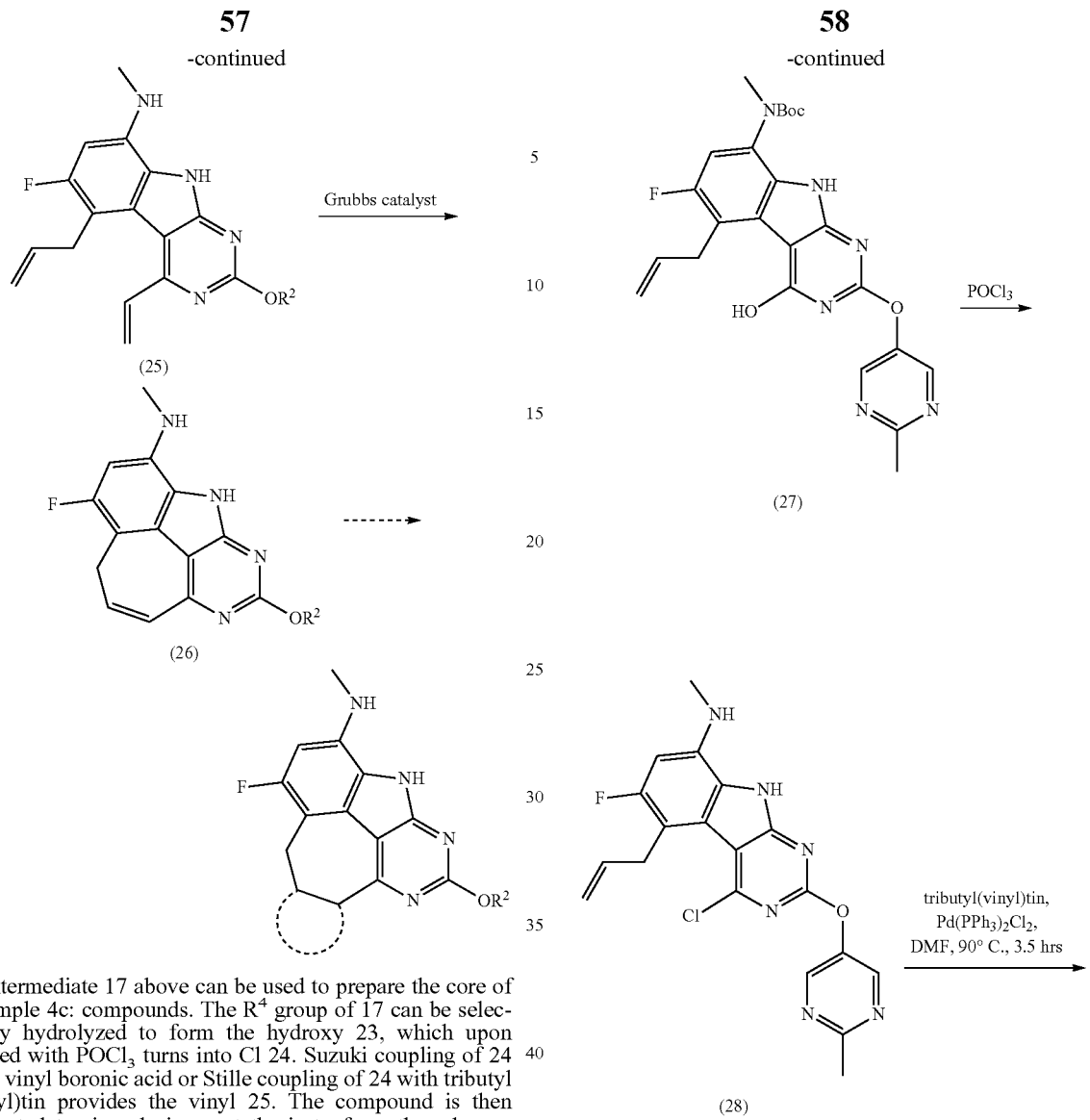

Intermediate 17 above can be used to prepare the core of Example 4c: compounds. The R⁴ group of 17 can be selectively hydrolyzed to form the hydroxy 23, which upon treated with POCl₃ turns into Cl 24. Suzuki coupling of 24 with vinyl boronic acid or Stille coupling of 24 with tributyl (vinyl)tin provides the vinyl 25. The compound is then subjected to ring-closing metathesis to form the advance intermediate 26. Compounds having an OH-containing substituent in the D Ring can arise from 26 via variety of reaction of alkene such as dihydroxylation, Diels-Alder reaction, cyclopropanation, etc.

Example 4d

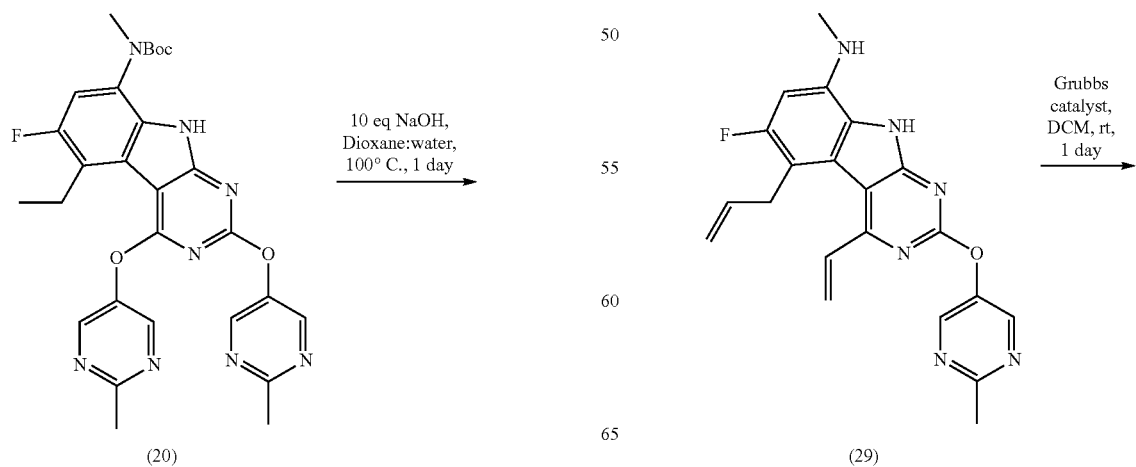

-continued

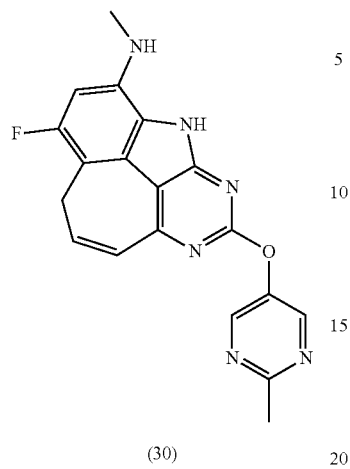

(30)

Compound 27: The mixture of compound 20 (1.145 g, 2 mmol) and sodium hydroxide (800 mg, 20 mmol) in dioxane (10 ml) and water (10 ml) were refluxed at 100° C. for 1 day. It was then purified through C18 column chromatography. The collected fractions were extracted with DCM (100 ml), and the aqueous layer was back-extracted with DCM (50 ml×2). The combined organic layers were concentrated by rotary evaporation to afford the title compound as yellow solid (800 ing, 83.2%). LC-MS: M+1: 481.6.

Compound 28: To the solution of compound 27 (800 mg, 1.665 mmol) in POCl$_3$ (6 ml) was added diethylisopropylamine (430 mg, 3.33 mmol). The resulting solution was heated at 70° C. for 1 hour then 80° C. for 1 day. After the reaction was cooled to rt, it was poured into a beaker containing about 100 g of ice. The precipitate was dissolved with DCM (80 ml), and the solution was then extracted. The aqueous layer was back-extracted with DCM (50 ml×2). The combined organic layers were concentrated by rotor evaporation and purified through C18 column chromatography. The collected fractions were extracted with DCM and concentrated by rotary evaporation to afford the title product as peach color solid (525 mg, 79%). LC-MS: M+1: 399.1.

Compound 29: To the solution of compound 28 (525 mg, 1.32 mmol) in anhydrous DMF (2 ml) was added tributyl (vinyl)tin (835 mg, 2.63 mmol). After the atmosphere of the mixture solution was purged with nitrogen, Pd(PPh$_3$)$_2$Cl$_2$ (92.1 mmol, 0.132 mmol) was added. The reaction was heated at 90° C. for 2 hours, and then an additional amount of Pd(PPh$_3$)$_2$Cl$_2$ (92.1 mmol, 0.132 mmol) was added. The reaction was continued at 90° C. for 1.5 hours. It was then cooled to rt and purified through C18 column chromatography. The collected fractions were extracted with DCM, and the organic layer was concentrated by rotary evaporation to afford the title product as red brown solid (421.3 mg, 82%). LC-MS: M+1: 391.4.

Compound 30:

To the solution of compound 29 (42.1 mg, 0.11 mmol) in DCM (2 ml) was added with Grubbs catalyst (first generation, 16.5 mg, 0.02 mmol). The mixture was stirred at rt for 1 day. It was then concentrated by rotary evaporation and purified through HPLC to afford the title compound as yellow solid (21.9 mg, 55%).

Example 5

Synthesis of Prodrugs

Example 5a

Synthesis of

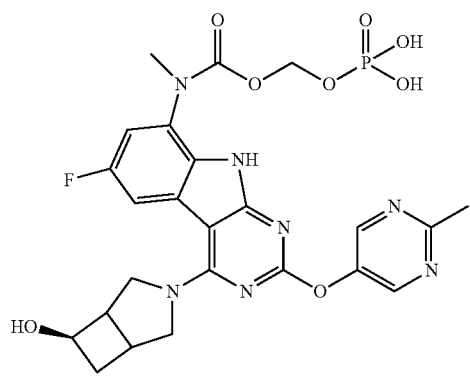 [SMILES: Cc1ncc(Oc2nc(N3CC4C[C@@H](O)C4C3)c3c(n2)[nH]c2c(N(C)C(=O)OCOP(=O)(O)O)cc(F)cc23)cn1]

General Scheme

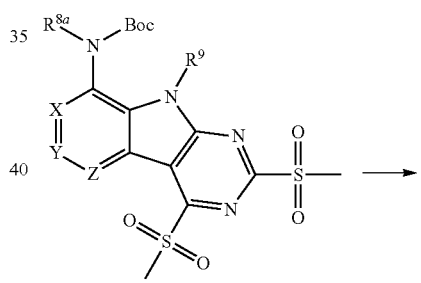

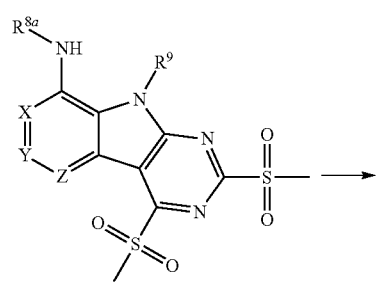

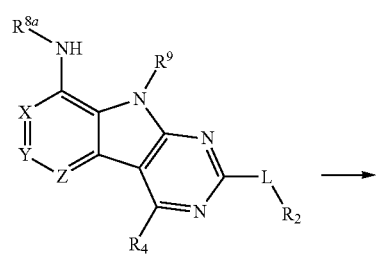

-continued

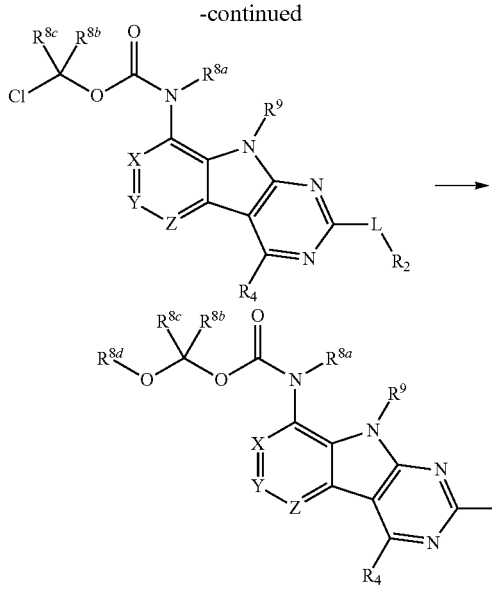

Example 5b

Synthesis of

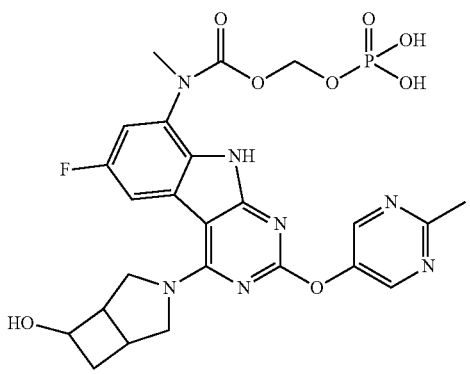 [SMILES: Cc1ncc(Oc2nc(N3CC4CC(O)C4C3)c3c(n2)[nH]c2c(N(C)C(=O)OCOP(=O)(O)O)cc(F)cc23)cn1]

Chloromethyl (6-fluoro-4-(6-hydroxy-3-azabicyclo[3.2.0]heptan-3-yl)-2-((2-methylpyrimidin-5-yl)oxy)-9H-pyrimido[4,5-b]indol-8-yl)(methyl)carbamate (2)

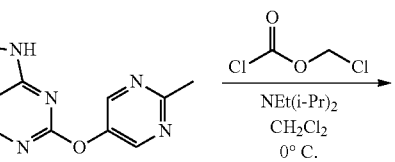

The mixture of 1 (0.180 g, 0.413 mmol) and di-isopropylethylamine (0.267 g, 2.07 mmol) in CH$_2$Cl$_2$ (10 mL) were cooled to 0° C. under nitrogen atmosphere. Chloromethyl chloroformate (0.061 mL, 0.475 mmol) dissolved in CH$_2$Cl$_2$ (0.5 mL) was dropwise added into the reaction mixture via syringe. The resulting yellow solution was stirred for 1 hr and then concentrated under reduced pressure. The crude product was purified by HPLC to provide 2 (0.080 g, 0.152 mmol, 37%) as yellow solid. LC/MS (ESI, M+H$^+$)=528.

((Di-tert-butoxyphosphoryl)oxy)methyl (6-fluoro-4-(6-hydroxy-3-azabicyclo[3.2.0]heptan-3-yl)-2-((2-methylpyrimidin-5-yl)oxy)-9H-pyrimido[4,5-b]indol-8-yl(methyl)carbamate (3)

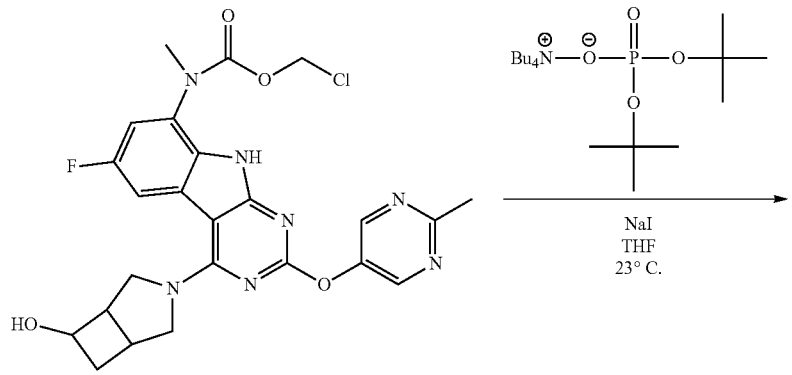

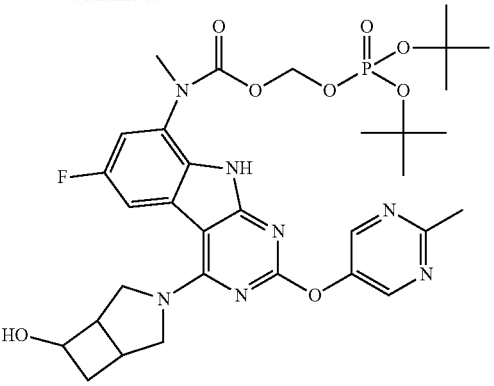

3

The mixture of 2 (0.080 g, 0.152 mmol), sodium iodide (0.037 g, 0.246 mmol) and tetra-n-butylammonium di-tert-butylphosphate (0.222 g, 0.491 mmol) in anhydrous THF (10.0 mL) were stirred for 22 hr at 23° C. After being stirred for 22 hr, the resulting heterogeneous mixture was filtered and purified by HPLC to provide 3 (0.060 g, 0.085 mmol, 56%) as white solid. LC/MS (ESI, M+H$^+$)=702.

(Phosphonooxy)methyl (6-fluoro-4-(6-hydroxy-3-azabicyclo[3.2.0]heptan-3-yl)-2-((2-methylpyrimidin-5-yl)oxy)-9H-pyrimido[4,5-b]indol-8-yl) (methyl) carbamate (4)

The mixture of 3 (0.060 g, 0.085 mmol) in trifluoroacetic acid (3.0 mL) were stirred for 15 min at 23° C. Trifluoroacetic acid was evaporated by reduced pressure and the crude product was purified by HPLC to give 4 (0.043 g, 0.072 mmol, 85%) as white solid. LC/MS (ESI, M+H$^+$)=590.

Example 5c

Synthesis of Prodrugs

General Scheme

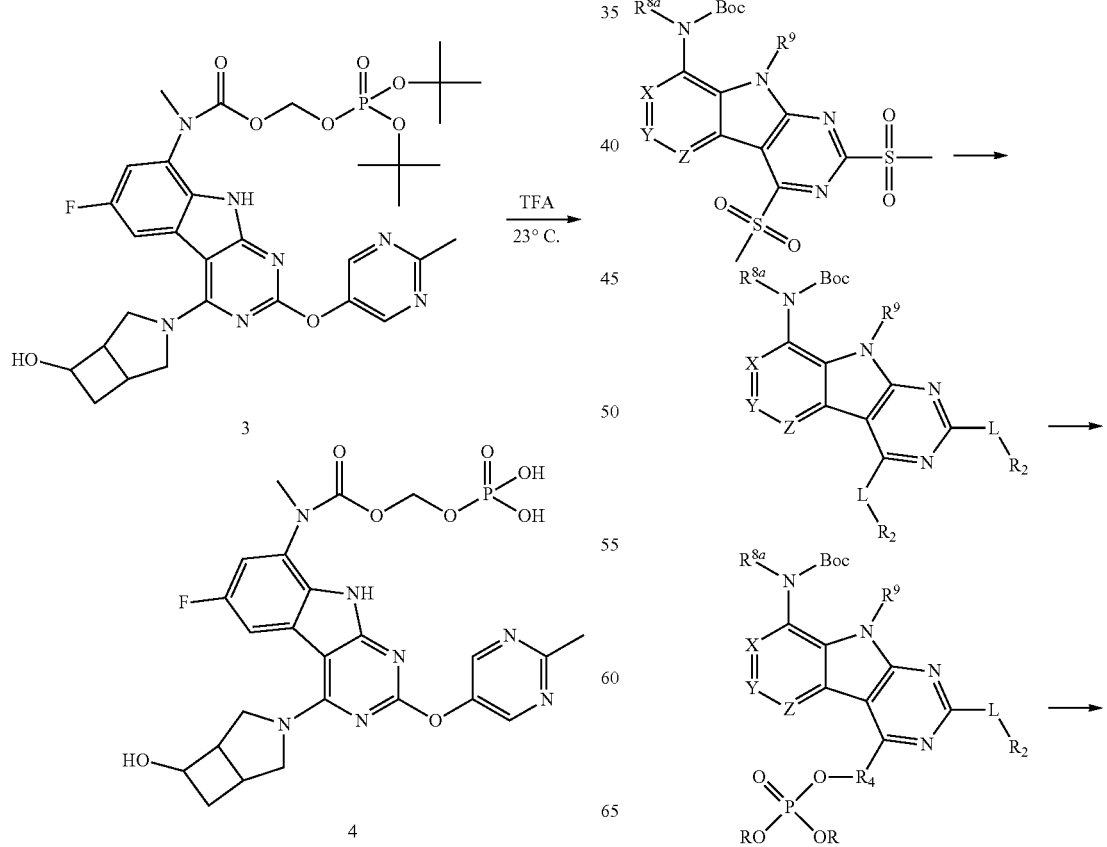

-continued

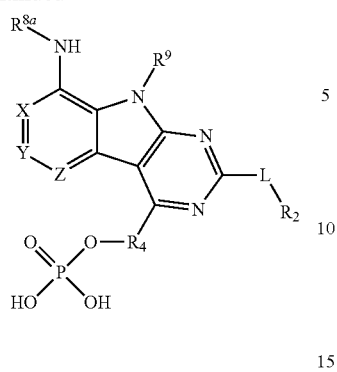

Synthesis of Prodrugs

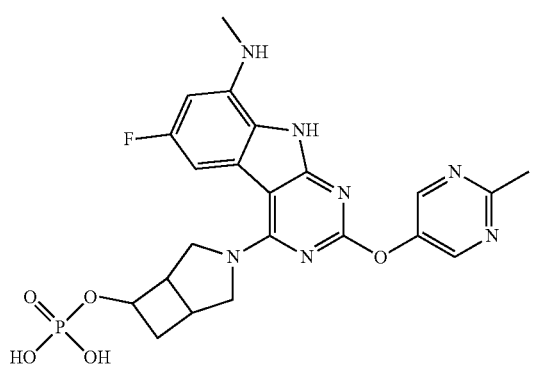

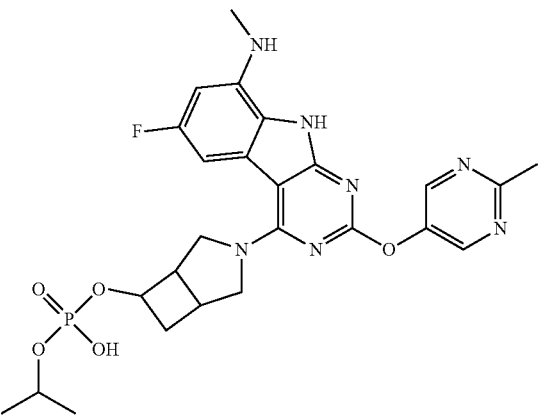

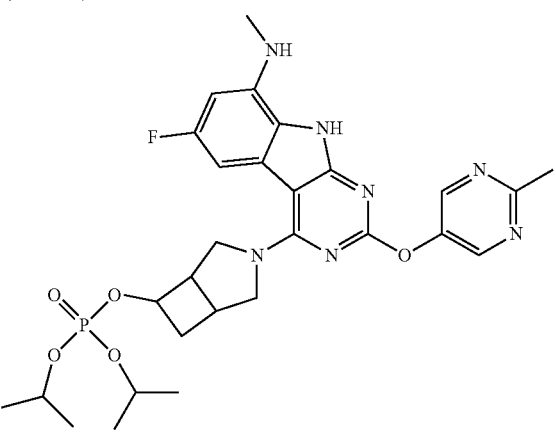

-continued

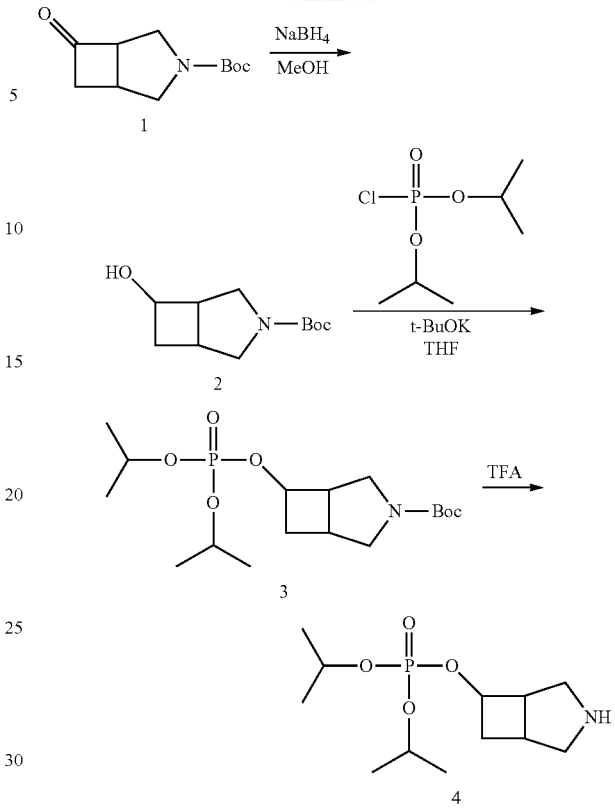

tert-butyl 6-hydroxy-3-azabicyclo[3.2.0]heptane-3-carboxylate (2)

To a solution of 1 (0.525 g, 2.48 mmol) in anhydrous MeOH (5.0 mL) was added NaBH$_4$ (0.093 g, 2.48 mmol) under nitrogen atmosphere at 23° C. The reaction mixture was stirred for 15 min and checked by LC/MS. Upon completion, the mixture was treated with ice water (25 mL) and was extracted with EtOAc (50 mL×3). The combined organic layers were dried over MgSO$_4$, filtered, and concentrated in vacuo. The crude product 2 as light yellow oil was used for next reaction without further purification. LC/MS (ESI, M+H$^+$)=214.

tert-butyl 6-(((diisopropoxyphosphoryl)oxy)-3-azabicyclo[3.2.0]heptane-3-carboxylate (3)

To a solution of 2 (0.525 g, 2.46 mmol) in anhydrous THF (5.0 mL) was added t-BuOK (4.96 mL, 4.96 mmol, 1.0 M solution in THF) under nitrogen atmosphere at 23° C. The resulting mixture was stirred for 15 min and then diisopropyl phosphorochloridate (1.00 g, 4.96 mmol) dissolved in THF (0.5 mL) was dropwise added by syringe. After being stirred for 2 hr, the mixture was treated with ice water (50 mL) and was extracted with EtOAc (100 mL×3). The combined organic layers were dried over MgSO$_4$, filtered, and concentrated in vacuo. The crude product 3 was used for next reaction without further purification. LC/MS (ESI, M+H$^+$)=378.

3-azabicyclo[3.2.0]heptan-6-yl diisopropyl phosphate (4)

The mixture of 3 in trifluoroacetic acid (1.5 mL) was stirred for 15 min at 23° C. Trifluoroacetic acid was evaporated by reduced pressure and the crude product 4 as orange oil was used for next reaction without further purification. LC/MS (ESI, M+H$^+$)=278.

tert-butyl (4-(6-(((diisopropoxyphosphoryl)oxy)-3-azabicyclo[3.2.0]heptan-3-yl)-6-fluoro-2-((2-methylpyrimidin-5-yl)oxy)-9H-pyrimido[4,5-b]indol-8-yl (methyl)carbamate (6)

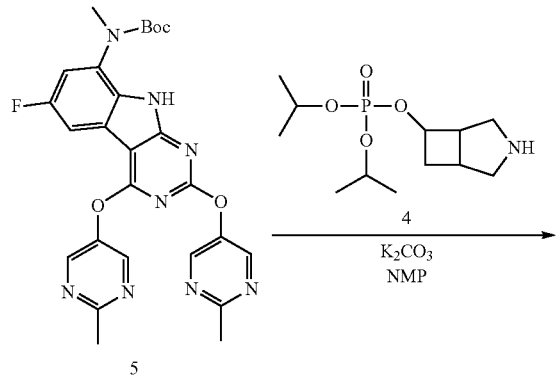

The mixture of 5 (0.426 g, 0.800 mmol), 3-azabicyclo[3.2.0]heptan-6-yl diisopropyl phosphate 4 (0.670 g, 2.40 mmol) and K$_2$CO$_3$ (0.553 g, 4.00 mmol) in NMP (3.5 mL) were stirred for 2 hr at 100° C. After being stirred for 2 hr, the reaction was checked by LC/MS. The resulting heterogeneous mixture was cooled to 23° C. and purified by HPLC to provide 6 (0.265 g, 0.379 mmol, 47%) as white solid. LC/MS (ESI, M+H$^+$)=700.

3-(6-fluoro-8-(methylamino)-2-((2-methylpyrimidin-5-yl)oxy)-9H-pyrimido[4,5-b]indol-4-yl)-3-azabicyclo[3.2.0]heptan-6-yl dihydrogen phosphate (7)

3-(6-fluoro-8-(methylamino)-2-((2-methylpyrimidin-5-yl)oxy)-9H-pyrimido[4,5-b]indol-4-yl)-3-azabicyclo[3.2.0]heptan-6-yl isopropyl hydrogen phosphate (8), and

3-(6-fluoro-8-(methylamino)-2-((2-methylpyrimidin-5-yl)oxy)-9H-pyrimido[4,5-b]indol-4-yl)-3-azabicyclo[3.2.0]heptan-6-yl diisopropyl phosphate (9)

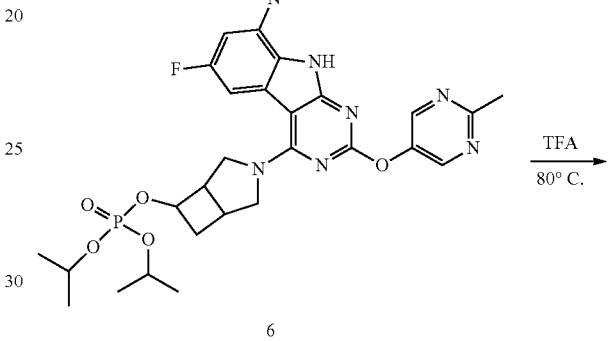

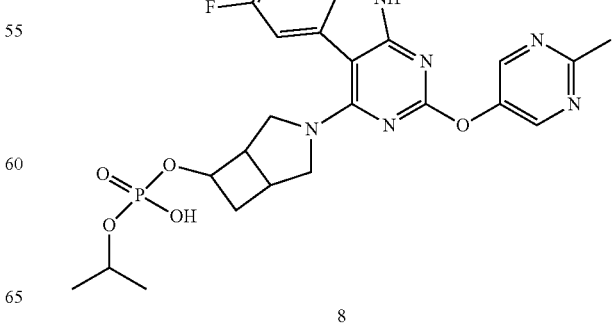

-continued

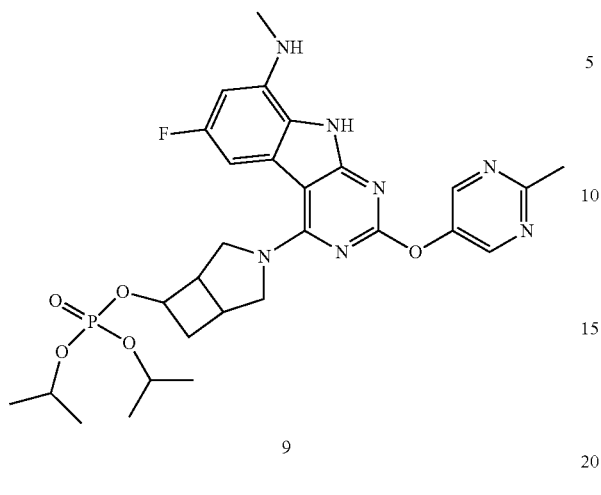

9

The mixture of 6 (0.265 g, 0.379 mmol) in trifluoroacetic acid (3.5 mL) were stirred for 24 hr at 80° C. under nitrogen atmosphere. Trifluoroacetic acid was evaporated by reduced pressure and the crude product was purified by HPLC to give 3-(6-fluoro-8-(methylamino)-2-((2-methylpyrimidin-5-yl)oxy)-9H-pyrimido[4,5-b]indol-4-yl)-3-azabicyclo[3.2.0]heptan-6-yl dihydrogen phosphate 7 (0.055 g, 0.107 mmol, 28%) as yellow solid (LC/MS (ESI, M+H⁺)=516), 3-(6-fluoro-8-(methylamino)-2-((2-methylpyrimidin-5-yl)oxy)-9H-pyrimido[4,5-b]indol-4-yl)-3-azabicyclo[3.2.0]heptan-6-yl isopropyl hydrogen phosphate 8 (0.055 g, 0.099 mmol, 26%) as light yellow solid (LC/MS (ESI, M+H⁺)=558) and 3-(6-fluoro-8-(methylamino)-2-((2-methylpyrimidin-5-yl)oxy)-9H-pyrimido[4,5-b]indol-4-yl)-3-azabicyclo[3.2.0]heptan-6-yl diisopropyl phosphate 9 (0.040 g, 0.067 mmol, 18%) as white solid (LC/MS (ESI, M+H⁺=600).

Example 5d

Synthesis of

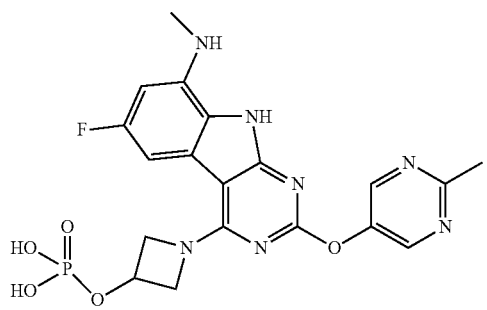 [SMILES: CNc1cc(F)cc2c1[nH]c1nc(Oc3cnc(C)nc3)nc(N3CC(OP(=O)(O)O)C3)c12]

The prodrug above (LC/MS (ESI, M+H⁺)=476) was prepared using procedures similar to that described in Example 5c above.

Example 5e

Synthesis of

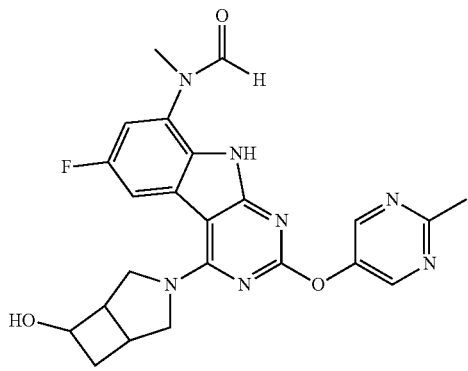 [SMILES: Cc1ncc(Oc2nc(N3CC4CC(O)C4C3)c3c(n2)[nH]c2c(N(C)C=O)cc(F)cc23)cn1]

General Scheme

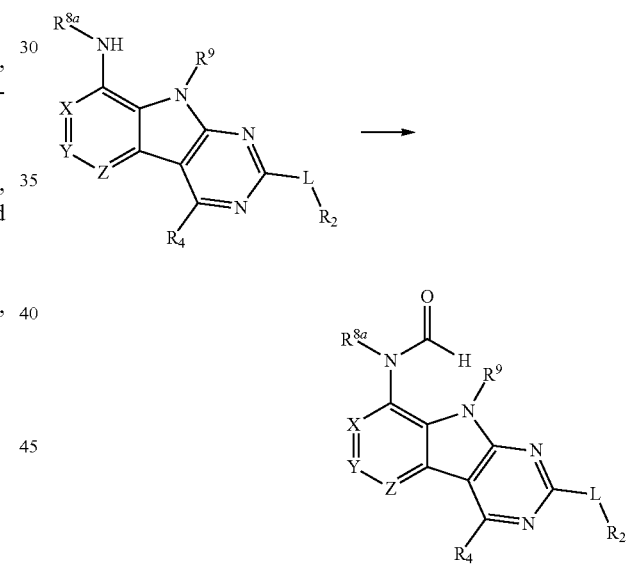

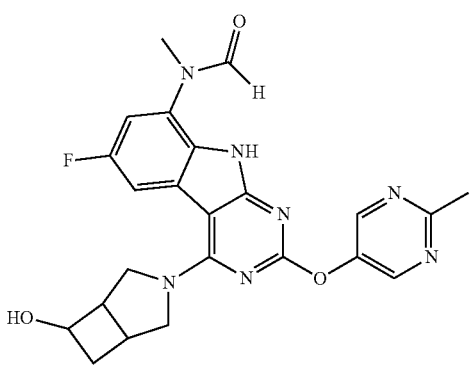

N-(6-fluoro-4-(6-hydroxy-3-azabicyclo[3.2.0]heptan-3-yl)-2-((2-methylpyrimidin-5-yl)oxy)-9H-pyrimido[4,5-b]indol-8-yl)-N-methylformamide (2)

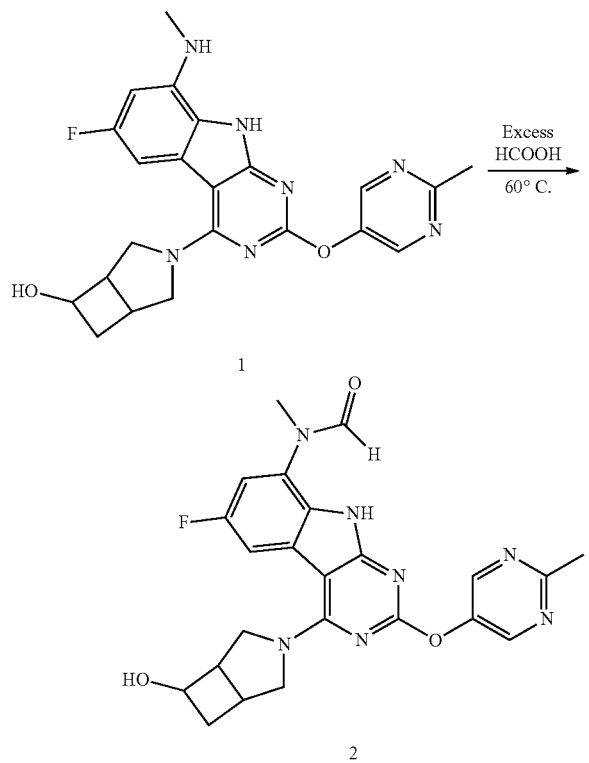

The mixture of 1 (0.170 g, 0.390 mmol) in formic acid (1.5 mL) was stirred for 45 min at 60° C. under nitrogen atmosphere. Excess formic acid was evaporated by reduced pressure and the crude product was purified by HPLC to give a di-formyl adduct. This di-formyl adduct was slowly hydrolyzed to provide mono-formyl product in MeCN and $H_2O$ with 5% TFA. The solvent was removed under reduced pressure and the crude product was purified by HPLC to give N-(6-fluoro-4-(6-hydroxy-3-azabicyclo[3.2.0]heptan-3-yl)-2-((2-methylpyrimidin-5-yl)oxy)-9H-pyrimido[4,5-b]indol-8-yl)-N-methylformamide 2 (0.075 g, 0.162 mmol, 42%) as white solid (LC/MS (ESI, M+H$^+$)=464).

Example 6

Determination of Anti-bacterial Efficacy

Colonies of *H. influenzae*, *E. coli*, *S. aureus*, *A. baumannii*, *S. pneumoniae*, *P. aeruginosa*, and *B. thailandensis* were picked from overnight plates and resuspended in 3 mL DPBS solution. Absorbance was read at 600 nM and suspensions were diluted to an OD of 0.1.

Inocula were added to appropriate growth medium, and 98 µL of the mixture were plated into columns 1-11 of a 96 well flat-bottomed cell-culture plate. Column 12 was plated with medium only.

TABLE 1

| | | Resuspended Cells | Medium | Incubation |
|---|---|---|---|---|
| *S. aureus* | ATCC 13709 | 50 uL | 20 mL Mueller Hinton cationic adjusted | Ambient 18 h |
| SA + serum | ATCC 13709 | 50 uL | 16 mL MHCA + 4 mL mouse serum | Ambient 18 h |
| *S. pneumoniae* | ATCC 51916 | 100 uL | 20 mL MHCA + 3% Laked Horse Blood | 5% $CO_2$ 18 h |
| *E. coli* | ATCC 25922 | 100 uL | 20 mL MHCA | Ambient 18 h |
| EC + serum | ATCC 25922 | 100 uL | 16 mL MHCA + 4 mL mouse serum | Ambient 18 h |
| *E. coli* | MX1313 | 100 uL | 20 mL MHCA | Ambient 18 h |
| *E. coli* imp | Benson BAS849 | 100 uL | 20 mL MHCA | Ambient 18 h |
| *E. coli* Δtolc | BW25113 Δtolc | 100 uL | 20 mL MHCA | Ambient 18 h |
| *P. aeruginosa* | ATCC 15692 | 100 uL | 20 mL MHCA | Ambient 18 h |
| *A. baumannii* | ATCC 19606 | 100 uL | 20 mL MHCA | Ambient 18 h |
| *A. baumannii* | MX2585 | 100 uL | 20 mL MHCA | Ambient 18 h |
| *K. pneumoniae* | ATCC 700603 | 100 uL | 20 mL MHCA | Ambient 18 h |
| *S. enteritidis* | ATCC 53000 | 100 uL | 20 mL MHCA | Ambient 18 h |
| *S. typhi* | ATCC 33459 | 100 uL | 20 mL MHCA | Ambient 18 h |
| *S. typhimurium* | ATCC 14028 | 100 uL | 20 mL MHCA | Ambient 18 h |
| *S. dysenteriae* | ATCC 13313 | 100 uL | 20 mL MHCA | Ambient 18 h |
| *Y. pestis* | CO92 pgm- | 100 uL | 20 mL MHCA | Ambient 42 h |
| *B. thailandensis* | ATCC E264 | 100 uL | 20 mL MHCA | Ambient 18 h |
| *C. jejuni* | ATCC 33560 | 100 uL | 20 mL MHCA | GasPak EZ Campy Container System 42 h |
| *F. tularensis* | holarctica LVS | 100 uL | 20 mL MHCA with Isovitalex | Ambient 42 h |
| *F. tularensis* | novicida Utah 112 | 100 uL | 20 mL MHCA with Isovitalex | Ambient 42 h |

2 μL of compound dilution series in 100% DMSO were added to columns 1-10. Plates were agitated in a plate-shaker for 1 min.

Mixtures of cells and media were diluted 1000× in DPBS and 100 μL were plated onto appropriate media and incubated overnight in order to count CFUs.

Plates were incubated overnight at 35° C. *H. influenzae* and *S. pneumoniae* plates were incubated with 5% $CO_2$.

10 μL of Alamar Blue (Invitrogen) were added to plates, and plates were agitated for 1 min in a plate-shaker. Plates were incubated at 35° C. for 1 h. Plates were read visually, with any change in color from blue read as alive.

Example 7

Determination of hERG Inhibition

A Cerep automated patch-clamp assay using Chinese Hamster Ovary K1 cells was used to measure hERG IC50 values. The degree of inhibition (%) was obtained by measuring the tail current amplitude, which is induced by a one second test pulse to −40 mV after a two second pulse to +20 mV, before and after drug incubation (the difference in current was normalized to control and multiplied by 100 to obtain the percent inhibition).

Concentration (log) response curves were fitted to a logistic equation (three parameters assuming complete block of the current at very high test compound concentrations) to generate estimates of the 50% inhibitory convcentration (IC50). The concentration-response relationship of each compound was constructed from the percentage reductions of current amplitude by sequential concentrations. The MIC and hERG IC50 values are provided in Table 2 below for the compounds tested.

The comparison shows the better hERG values for the —OH containing analogs while retaining Gram-negative activity, e.g. in *E. coli*.

TABLE 2

| R4 | R2 | Y, Z | MIC μg/mL | | | | | hREG $IC_{50}$ |
| --- | --- | --- | --- | --- | --- | --- | --- | --- |
| | | | Sa | Ec | Kpn | Ab | Pa | |
| $H_2N$-spiro[3.3]heptane | pyrimidine | C—F, C—H | ≤0.016 | 0.25 | 2 | 0.5 | 1 | 16 |
| HO-spiro[3.3]heptane | | | ≤0.016 | 1 | 4 | 4 | >16 | 100 |
| $H_2N$-bicyclo[2.2.1]heptane | pyrimidine | C—F, C—H | ≤0.016 | 0.13 | 2 | 0.5 | 1 | 4 |
| HO-bicyclo[2.2.1]heptane | | | ≤0.016 | 1 | 8 | 4 | >16 | 71 |
| $H_2N$-bicyclo[3.2.0]heptane | pyrimidine | C—F, C—H | ≤0.016 | 0.25 | 2 | 0.25 | 1 | 1 |
| HO-bicyclo[3.2.0]heptane | | | ≤0.016 | 0.13 | 1 | 0.5 | 16 | 20 |
| $H_2N$-bicyclo[3.1.0]hexane | pyrimidine | C—F, C—H | ≤0.016 | 0.13 | 2 | 0.25 | 4 | 9.5 |
| HO-bicyclo[3.1.0]hexane | | | ≤0.016 | 0.25 | 1 | 0.5 | >16 | 41 |

Example 8

Caco-2 Cell Monolayer Permeability

Caco-2 human colon carcinoma cell line (Caco-2) was used as a model system for intestinal epithelial permeability. There is similarity in uptake and barrier properties between this cell system and the small intestinal epithelial layer. See., Hidalgo I J, et al., Gastroenterology. 1989 March; 96(3): 736-49. *Characterization of the human colon carcinoma cell line (Caco-2) as a model system for intestinal epithelial permeability*. The profile of potential oral/IV candidates are shown in Table 3.

Example 9

In Vivo Mouse PK

Parallel Sampling

Typical protocol is a single dose intravenous and oral (gavage) administration with blood collection from each animal by cardiac puncture at selected (6 to 8) time points (n=3 mice per time point) into a tube containing an appropriate anticoagulant. The blood is centrifuged and the resulting plasma removed for subsequent analysis. After proper sample preparation, the plasma concentrations of a test compound are determined by LC-MS/MS and the pharmacokinetics (namely, area-under-curve or AUC) of the concentration-time profile from oral administration is compared with the corresponding pharmacokinetics from intravenous administration. The ratio of the AUC from oral administration to the AUC from intravenous administration gives the oral bioavailability (% F), as shown for select compounds below in Table 3. In addition, Caco values are shown.

The first two amine containing analogs in Table 3, were reported as two amine containing compounds having unexpectedly favorable hERG values, in the PCT application that claims priority to U.S. Prov. Pat. Appl. 61/700,159, but the oral bioavailability values are significantly less in comparison to the —OH containing compounds.

TABLE 3

| cmpd # | Caco ($10^{-8}$ cm/s) | Mouse % F | Dog % F | MIC μg/mL Sa | Ec | Kpn | Ab | Pa |
|---|---|---|---|---|---|---|---|---|
| 1.1 | <0.1 | <2% |  | ≤0.016 | 0.25 | 1 | 4 | 2 |
| 1.2 | 0.5, 1.7 | <2% |  | ≤0.016 | 0.13 | 1 | 2 | 1 |
| 1.3 | 5.5, 6.3 | 25% | 50% | ≤0.016 | 0.13 | 0.5 | 1 | 16 |
| 1.4 | 7.5 | 15% |  | ≤0.016 | 0.5 | 1 | 2 | >16 |

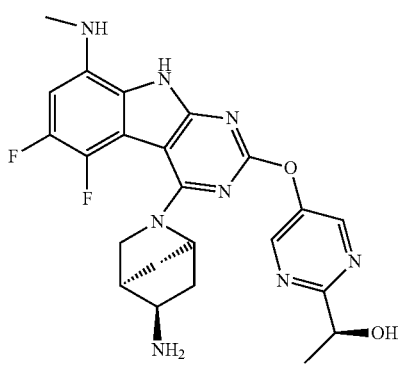

1.1

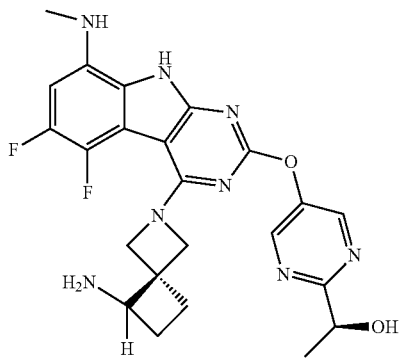

1.2

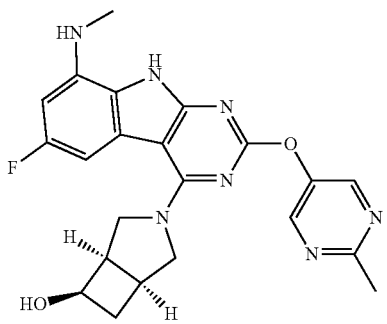

1.3

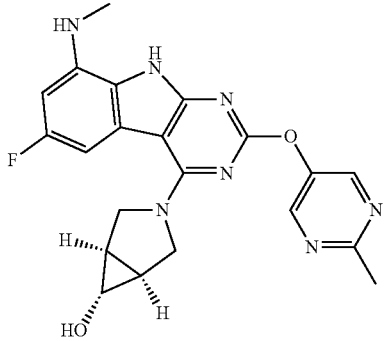

1.4

What is claimed is:
1. A compound having the structure of Formula I

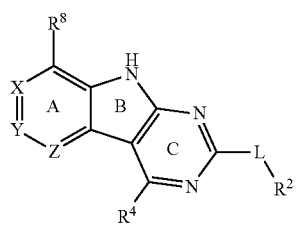

Formula I or pharmaceutically suitable salts, esters, and prodrugs thereof,
wherein
L is O, S, NH or $CH_2$,
$R^8$ is:
a) $NHCH_3$;
b) a prodrug-containing substituent, wherein the compound has the structure of Formula II:

Formula II

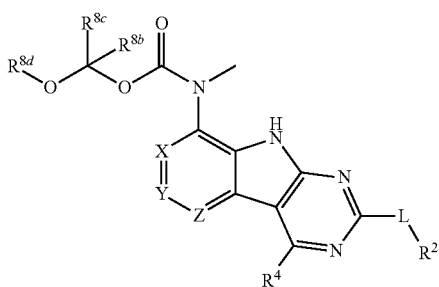

wherein R$^{8b}$ and R$^{8c}$ are independently H or C1-C6 alkyl;

wherein R$^{8d}$ is

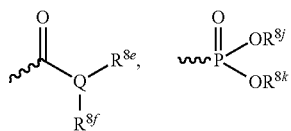

or a pharmaceutically acceptable salt thereof;

wherein Q is CH or N;

wherein R$^{8e}$ is (CR$^{8g}_2$)$_n$-basic amine, wherein each R$^{8g}$ may be independently be H or C1-C3 alkyl;

wherein n is 0-2;

wherein R$^{8f}$ is hydrogen or an optionally substituted C1-C6 alkyl with OH or NH$_2$;

wherein R$^{8e}$ and R$^{8f}$ may join to form a ring;

wherein R$^{8j}$ and R$^{8k}$ are independently H or C1-C8 hydrocarbyl residue; or c) a prodrug-containing substituent, wherein the compound has the structure of Formula II':

Formula II'

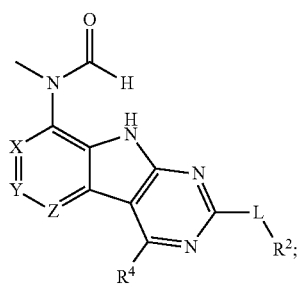

R$^2$ is:

a) phenyl, thiadiazolyl, pyridinyl or pyrimidinyl optionally substituted with a noninterfering substituent; or b) a prodrug-containing substituent, wherein the compound has the structure of Formula IV:

Formula IV

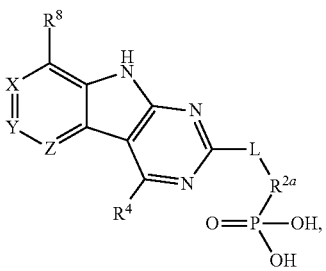

or a pharmaceutically acceptable salt thereof;

wherein R$^{2a}$ contains an oxygen residue derived from an R$^2$ as in a) wherein R$^2$ has an OH group, wherein the R$^2$ OH is replaced with an oxygen residue in R$^{2a}$, and wherein the oxygen residue is linked to P;

R$^4$ is:

a) a C3-C20 aliphatic hydrocarbyl residue containing 1-6 heteroatoms selected from O, S, and N wherein one heteroatoms of the 1-6 heteroatoms is an N in the backbone of the hydrocarbyl residue and wherein the N is attached to the C Ring, wherein the C3-C20 aliphatic hydrocarbyl residue is substituted with at least one hydroxyl substituent and 0-3 noninterfering substituents;

wherein the R$^4$ substituent does not project greater than about 3 Å below the plane of the A, B and C Rings toward the GyrB/ParE binding pocket floor in the bound conformation; and wherein R$^4$ does not sterically interfere with R$^2$ or Z when the compound is in the bound conformation, and wherein R$^4$ contains a single N; or b) a prodrug-containing substituent, wherein the compound has the structure of Formula V:

Formula V

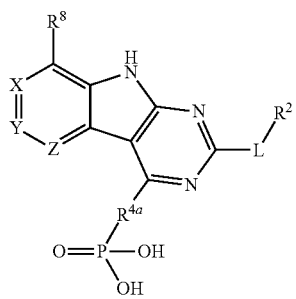

or a pharmaceutically acceptable salt thereof;

wherein R$^{4a}$ contains an oxygen residue derived from an R$^4$ as in a), wherein hydroxyl substituent of R$^4$ is replaced with an oxygen residue in R$^{4a}$, and wherein the oxygen residue is linked to P;

X is CH;

each of Y and Z may be independently CR$^Y$ or CR$^Z$ respectively, or N, wherein each of R$^y$ and R$^z$ is independently H, F, Cl, Br, CH$_3$, CF$_3$, CHF$_2$, CH$_2$F, or CN.

2. The compound of claim 1 wherein each of Y or Z are independently CH or CF.

3. The compound of claim 2 wherein at least one of Y and Z is CF.

4. The compound of claim 1 wherein R$^2$ is 1,3,4-thiadiazolyl.

5. The compound of claim 1 wherein $R^4$ is selected from the group consisting of
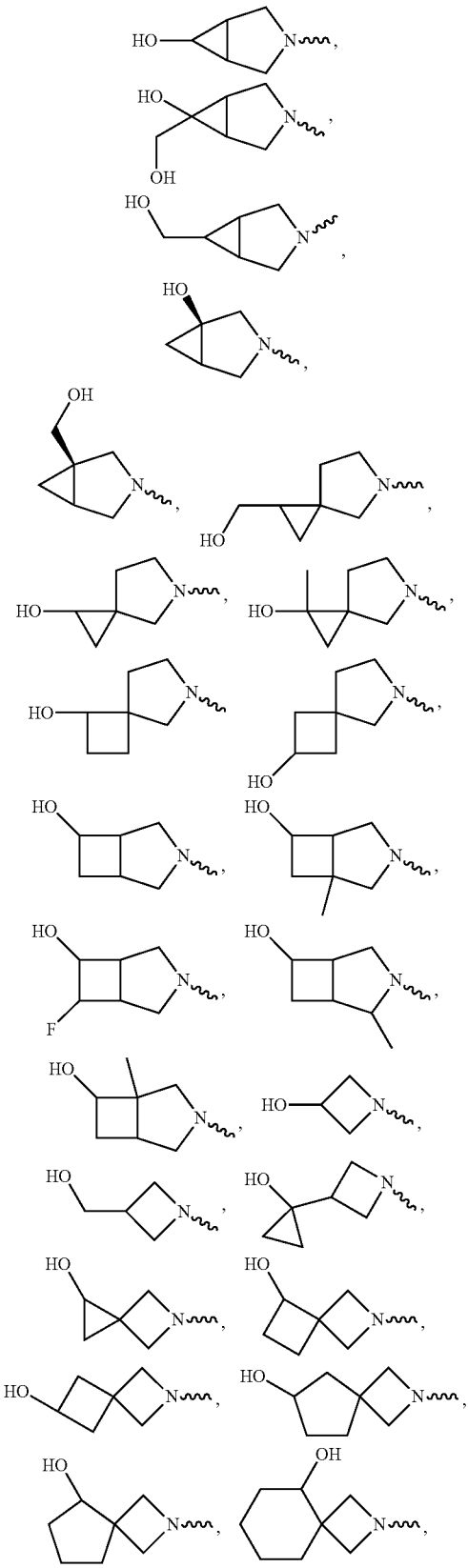
-continued
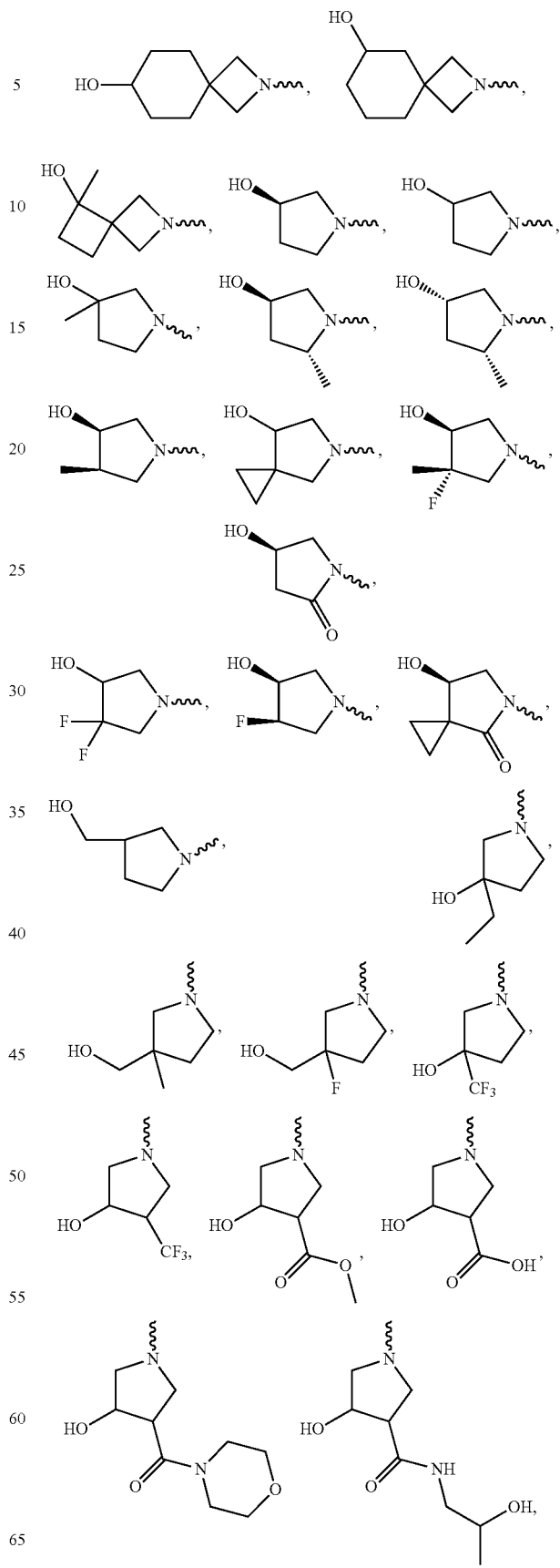

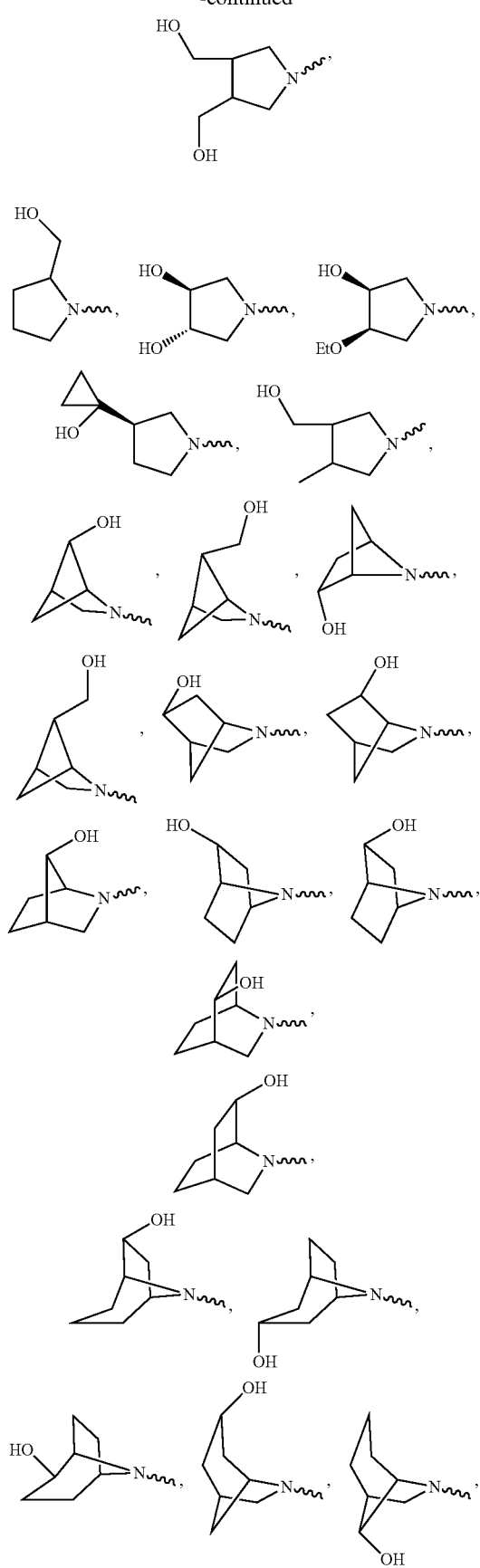
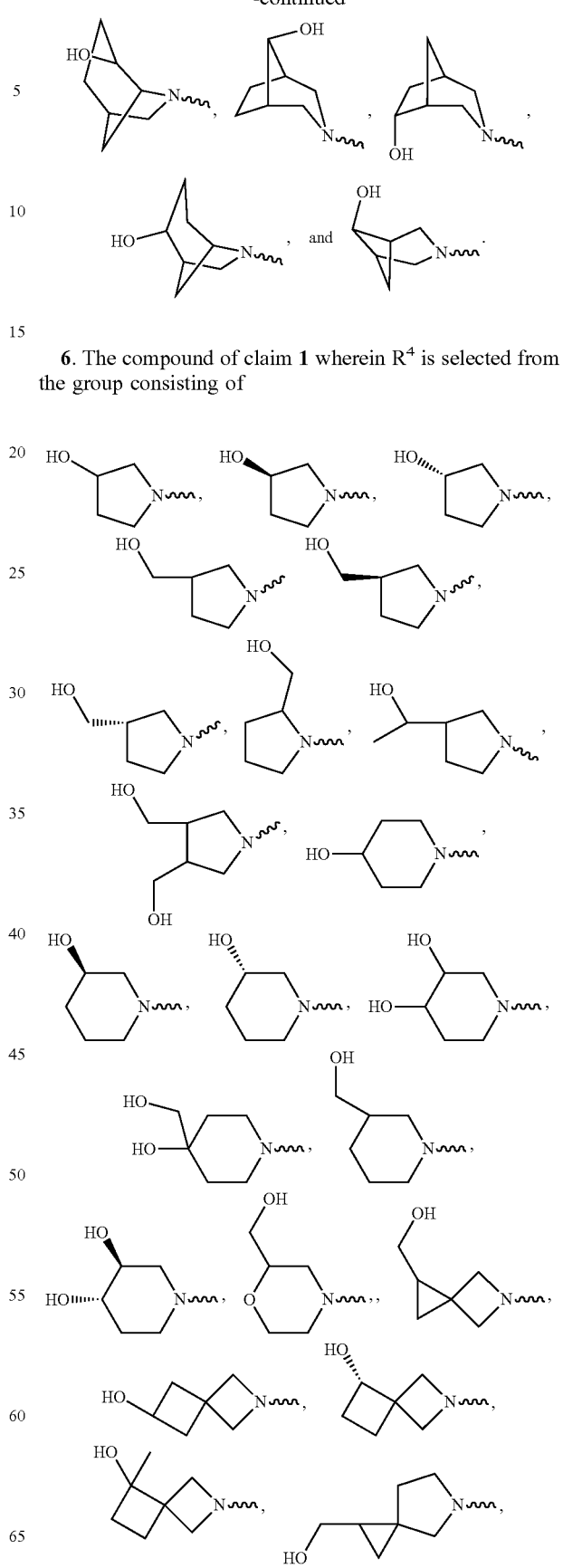
6. The compound of claim 1 wherein $R^4$ is selected from the group consisting of

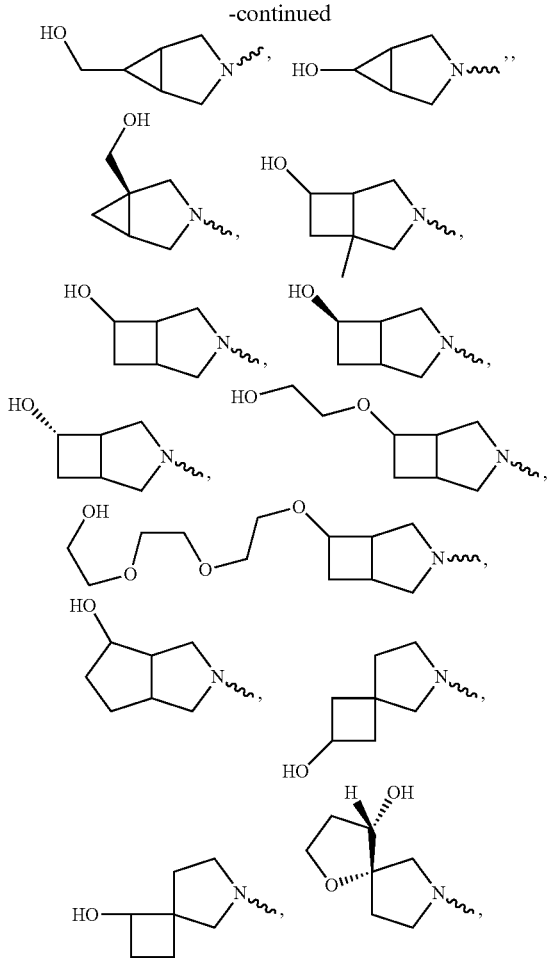
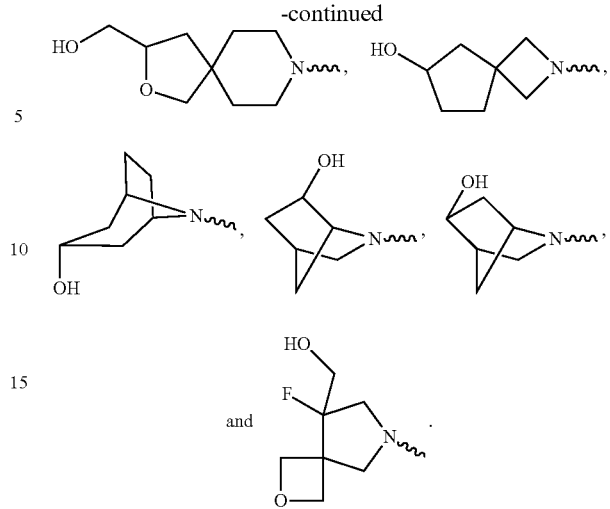
7. The compound of claim 1 wherein the compound is selected from the group consisting of
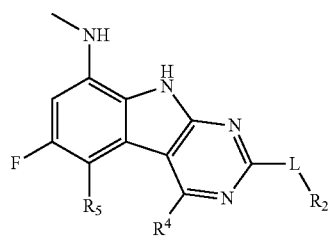
| R4 | L | R2 | R5 |
|---|---|---|---|
| ![pyrrolidine-OH] | O | ![pyrimidine-Me] | H |
| ![azetidine-OH] | O | ![pyrimidine-Me] | H |
| ![azetidine-OH] | O | ![pyrimidine-NH2] | H |
| ![azetidine-OH] | O | ![pyrimidine-CH2NH2] | H |
| ![bicyclic-OH] | O | ![pyrimidine-Me] | H |

-continued
| R4 | L | R2 | R5 |
|---|---|---|---|
| 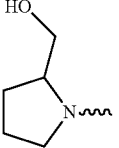 | O | 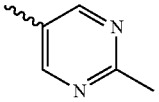 | H |
| 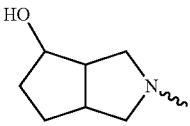 | O | 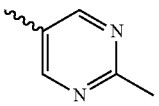 | H |
| 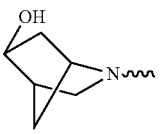 | O | 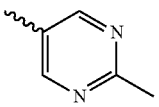 | H |
| 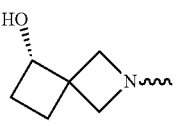 | O | 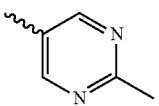 | H |
| 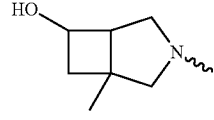 | O | 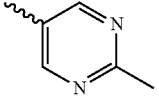 | H |
| 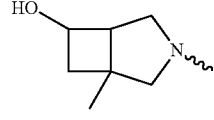 | O | 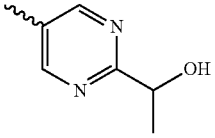 | H |
| 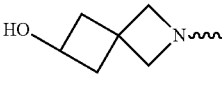 | O | 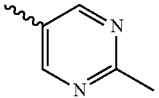 | H |
| 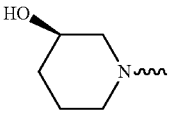 | O | 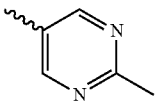 | H |
| 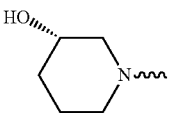 | O | 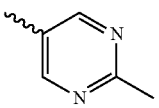 | H |
| 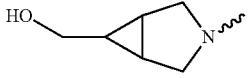 | O | 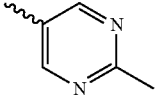 | H |
| 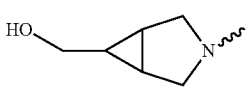 | O | 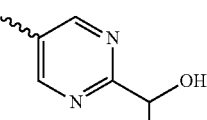 | H |

| R4 | L | R2 | R5 |
|---|---|---|---|
| (hydroxy-3-azabicyclo[3.1.0]hexane) | O | (2-methylpyrimidin-5-yl) | H |
| (4-hydroxypiperidine) | O | (2-methylpyrimidin-5-yl) | H |
| (1-(hydroxymethyl)-3-azabicyclo[3.1.0]hexane) | O | (2-methylpyrimidin-5-yl) | H |
| (hydroxy-3-azabicyclo[3.2.0]heptane) | O | (2-methylpyrimidin-5-yl) | F |
| (hydroxy-3-azabicyclo[3.2.0]heptane) | O | (2-methylpyrimidin-5-yl) | F |
| (6-(hydroxymethyl)-3-azabicyclo[3.1.0]hexane) | O | (2-(oxetan-3-ylamino)pyrimidin-5-yl) | H |
| (hydroxy-3-azabicyclo[3.2.0]heptane) | O | (2-(1-hydroxyethyl)pyrimidin-5-yl) | F |
| (4-hydroxy-4-(hydroxymethyl)piperidine) | O | (2-methylpyrimidin-5-yl) | H |
| (hydroxy-azabicyclic) | O | (2-methylpyrimidin-5-yl) | H |
| (hydroxy-3-azabicyclo[3.1.0]hexane) | O | (2-cyclobutoxypyrimidin-5-yl) | H |
| (hydroxy-3-azabicyclo[3.2.0]heptane) | O | (2-cyclobutoxypyrimidin-5-yl) | H |
| (hydroxy-oxa-azaspiro) | O | (2-methylpyrimidin-5-yl) | H |

| R4 | L | R2 | R5 |
|---|---|---|---|
| HO-[bicyclic N with CH2OH] | O | [pyridine-carboxylic acid] | H |
| HO-[bicyclic N with CH2OH] | O | [pyridine-C(O)-N-bicyclic-NH2] | H |
| HO-[bicyclic N with CH2OH] | O | [pyridine-C(O)NH-O-CH2CH2-N(CH3)2] | H |
| HO-[bicyclo[3.2.0] N] | O | [pyrimidine-CH(OH)CH3] | H |
| HO-[bicyclic N with CH2OH] | O | [pyrimidine-NHCH3] | H |
| HO-[bicyclo[3.2.0] N] | O | [pyrimidine-NHCH3] | H |
| HO-[bicyclic N] | O | [pyrimidine-NHCH3] | H |
| HO-[3-hydroxypiperidine] | O | [pyrimidine-NHCH3] | H |
| HO-[bicyclic N with CH2OH] | O | [pyridine-C(O)NH-OCH3] | H |
| HO-[(S)-3-hydroxypyrrolidine] | O | [pyrimidine-CH3] | H |
| HO-[(R)-3-hydroxypyrrolidine] | O | [pyrimidine-CH3] | H |

-continued
| R4 | L | R2 | R5 |
|---|---|---|---|
| 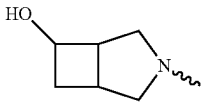 | O | 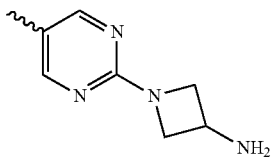 | H |
| 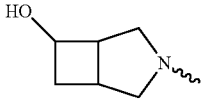 | O | 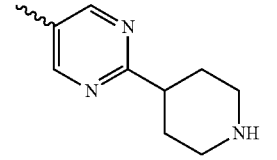 | H |
| 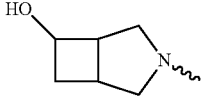 | O | 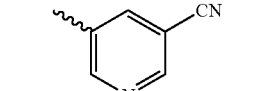 | H |
| 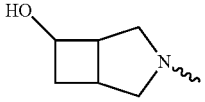 | O | 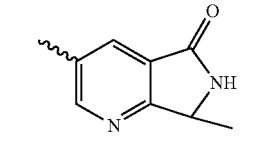 | H |
|  | O | 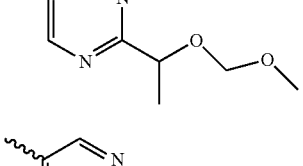 | H |
| 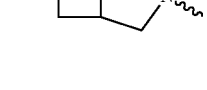 | O | 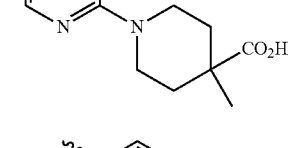 | H |
|  | O | 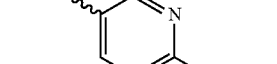 | H |
|  | O | 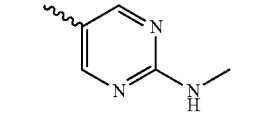 | H |
| 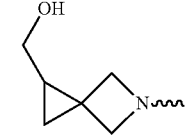 | O | 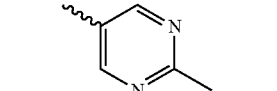 | H |
| 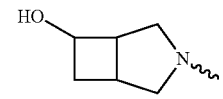 | O | 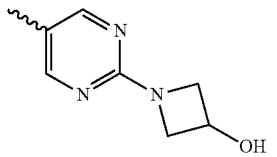 | H |

| R4 | L | R2 | R5 |
|---|---|---|---|
| 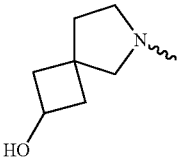 | O | 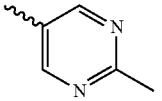 | H |
| 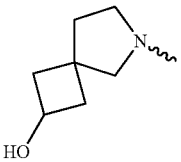 | O | 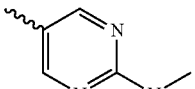 | H |
|  | O | 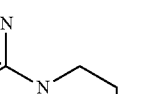 | H |
|  | O | 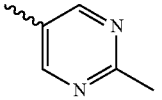 | H |
|  | O | 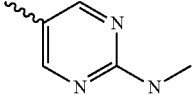 | H |
| 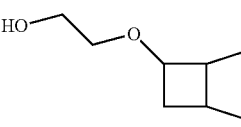 | O | 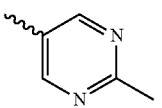 | H |
| 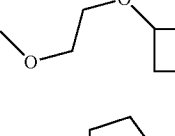 | O | 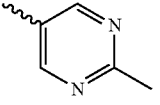 | H |
|  | O | 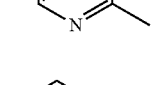 | H |
| 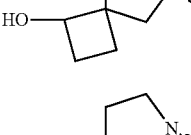 | O | 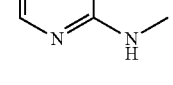 | H |
| 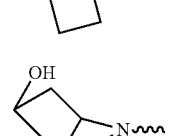 | O | 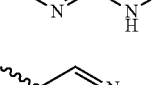 | H |
|  | O | 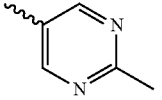 | H |

-continued
| R4 | L | R2 | R5 |
|---|---|---|---|
| 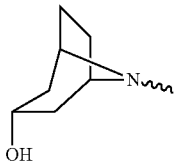 | O | 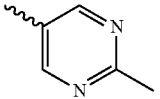 | H |
| 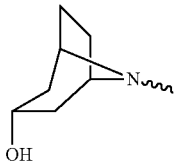 | O | 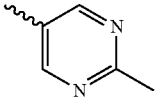 | H |
| 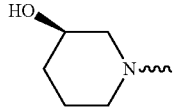 | O | 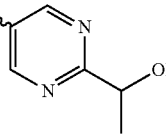 | H |
| 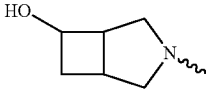 | O | 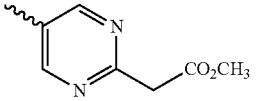 | H |
| 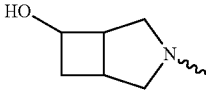 | O | 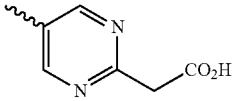 | H |
| 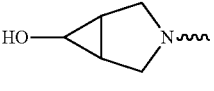 | O | 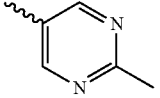 | F |
| 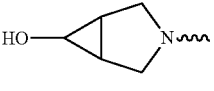 | O | 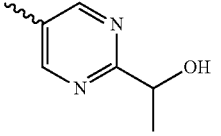 | F |
| 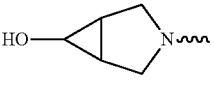 | O | 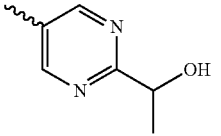 | F |
|  | O | 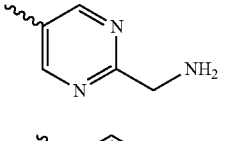 | H |
| 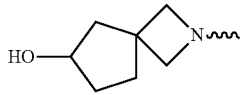 | O | 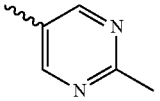 | H |
| 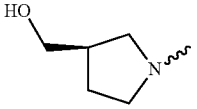 | O | 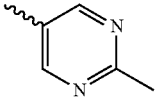 | H |

| R4 | L | R2 | R5 |
|---|---|---|---|
| (3-hydroxymethyl pyrrolidinyl) | O | 2-methylpyrimidin-5-yl | H |
| (3-hydroxymethyl pyrrolidinyl) | O | 2-methylpyrimidin-5-yl | F |
| (3-hydroxymethyl pyrrolidinyl) | O | 2-methylpyrimidin-5-yl | F |
| (3-hydroxymethyl pyrrolidinyl) | O | 2-(1-hydroxyethyl)pyrimidin-5-yl | F |
| (6-hydroxy-3-azabicyclo[3.2.0]heptyl) | O | 2-(hydroxymethyl)pyrimidin-5-yl | H |
| (hydroxy-azabicyclic) | O | 2-methylpyrimidin-5-yl | H |
| (3-hydroxymethyl piperidinyl) | O | 2-methylpyrimidin-5-yl | H |
| (6-hydroxy-3-azabicyclo[3.2.0]heptyl) | O | 2-methylpyrimidin-5-yl | H |
| (6-hydroxy-3-azabicyclo[3.2.0]heptyl) | O | 2-methylpyrimidin-5-yl | H |
| (3,4-dihydroxypiperidinyl) | O | 2-methylpyrimidin-5-yl | H |
| (hydroxy-cyanomethyl-azabicyclic) | O | 2-methylpyrimidin-5-yl | H |

| R4 | L | R2 | R5 |
|---|---|---|---|
| (3,4-dihydroxypiperidinyl) | O | (2-methylpyrimidin-5-yl) | H |
| (3,4-bis(hydroxymethyl)pyrrolidinyl) | O | (2-methylpyrimidin-5-yl) | H |
| (6-hydroxy-2-azabicyclo[3.2.0]heptyl) | S | (5-methyl-1,3,4-thiadiazol-2-yl) | H |
| (6-hydroxy-2-azabicyclo[3.2.0]heptyl) | S | (5-methyl-1,3,4-thiadiazol-2-yl) | H |
| (6-hydroxy-2-azabicyclo[3.2.0]heptyl) | S | (1,3,4-thiadiazol-2-yl) | H |
| (6-hydroxy-2-azabicyclo[3.2.0]heptyl) | O | (2-(3-hydroxycyclobutoxy)pyrimidin-5-yl) | H |
| (fluoro-hydroxymethyl-oxa-azaspiro) | O | (2-methylpyrimidin-5-yl) | H |
| (fluoro-hydroxymethyl-oxa-azaspiro) | O | (2-methylpyrimidin-5-yl) | H |
| (3-(hydroxymethyl)pyrrolidinyl) | O | (2-methylpyrimidin-5-yl) | F |
| (3-(1-hydroxyethyl)pyrrolidinyl) | O | (2-methylpyrimidin-5-yl) | H |

-continued

| R4 | L | R2 | R5 |
|---|---|---|---|
| HO-[bicyclic N] | NH | pyrimidine | H |
| HO-[bicyclic N] | O | pyrimidine-CH(OCH3) | H |
| HO-[bicyclic N, cyclopropane-fused] | O | pyrimidine-CH(OCH3) | H |
| HO-CH2-[morpholine] | O | pyrimidine-CH3 | H |
| HO-CH2-[oxaspiro piperidine] | O | pyrimidine-CH3 | H. |

8. The compound of claim 1 wherein the compound has the structure of Formula IV

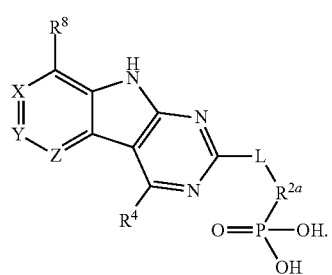

Formula IV

9. The compound of claim 1 wherein an optional noninterfering substituent on $R^2$ is a C1-C10 hydrocarbyl residue containing 0-5 O, S or N atoms in the backbone thereof optionally substituted with one or more of OH, =O, or $NH_2$.

10. The compound of claim 1 wherein an optional noninterfering substituent on $R^2$ is COOH, $NH_2$, OH, $CH_3$, $CH_2CH_3$, $NH_2$, $CH_2NH_2$, $NHCH_3$, $CH_2CH_2NH_2$, $CH_2CH_2OH$, $CH(CH_3)OH$, $CH(CH_3)OCH_3$, COOH, $CONHOCH_2CH_2N(CH_3)$, $CONHOCH_3$, $CH(CH_3)OCH_2OCH_3$, $CH_2COOH$, $CH_2COOCH_3$,

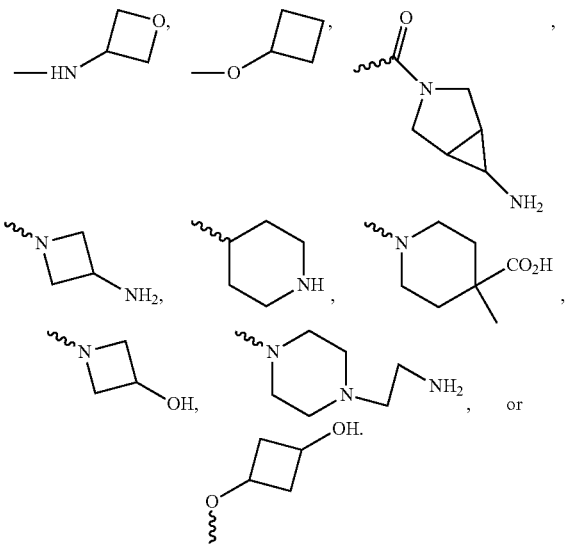

11. The compound of claim 1 wherein $R^4$ is not

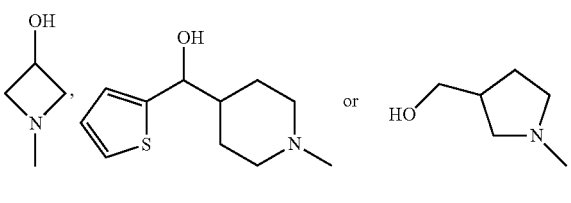

12. The compound of claim 1, wherein $R^8$ is $NHCH_3$;

$R^2$ is phenyl, thiadiazolyl, pyridinyl or pyrimidinyl optionally substituted with the noninterfering substituent;

$R^4$ is a C3-C20 aliphatic hydrocarbyl residue containing 1-6 heteroatoms selected from O, S, and N wherein one heteroatoms of the 1-6 heteroatoms is an N in the backbone of the hydrocarbyl residue and wherein the N is attached to the C Ring, wherein the C3-C20 aliphatic hydrocarbyl residue is substituted with at least one hydroxyl substituent and 0-3 noninterfering substituents;

wherein the $R^4$ substituent does not project greater than about 3 Å below the plane of the A, B and C Rings toward the GyrB/ParE binding pocket floor in the bound conformation; and wherein $R^4$ does not sterically interfere with $R^2$ or Z when the compound is in the bound conformation;

X is CH;

each of Y and Z may be independently $CR^Y$ or $CR^Z$ respectively, or N, wherein each of $R^Y$ and $R^Z$ is independently H, F, Cl, Br, $CH_3$, $CF_3$, $CHF_2$, $CH_2F$, or CN.

13. The compound of claim 12, wherein the noninterfering substituent on $R^2$ is selected from the group consisting of COOH, $NH_2$, OH, $CH_3$, $CH_2CH_3$, $NH_2$, $CH_2NH_2$, $NHCH_3$, $CH_2CH_2NH_2$, $CH_2CH_2OH$, $CH(CH_3)OH$, $CH(CH_3)OCH_3$, COOH, $CONHOCH_2CH_2N(CH_3)$, $CONHOCH_3$, $CH(CH_3)OCH_2OCH_3$, $CH_2COOH$, $CH_2COOCH_3$,

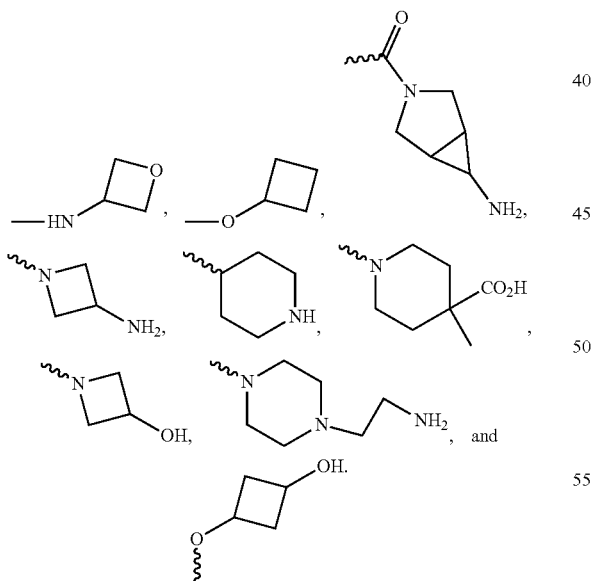

14. A composition comprising an effective amount of compound of claim 1 and a pharmaceutically acceptable carrier.

15. A method of treating a bacterial infection comprising administering to a patient in need thereof an effective amount of compound of claim 1.

16. A compound having the structure of Formula I

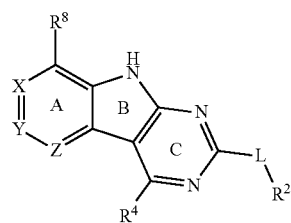

Formula I or pharmaceutically suitable salts, esters, and prodrugs thereof, wherein L is O, S, NH or $CH_2$;

$R^8$ is:

a) $NHCH_3$;

b) a prodrug-containing substituent, wherein the compound has the structure of Formula II:

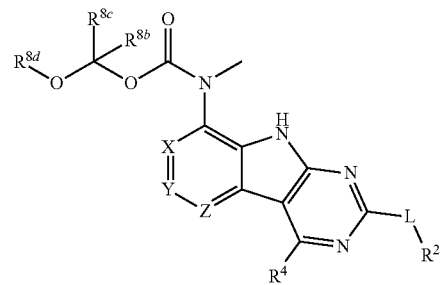

Formula II wherein $R^{8b}$ and $R^{8c}$ are independently H or C1-C6 alkyl;

wherein $R^{8d}$ is

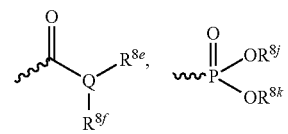

or a pharmaceutically acceptable salt thereof;

wherein Q is CH or N;

wherein $R^{8e}$ is $(CR^{8g}_2)_n$-basic amine, wherein each $R^{8g}$ may be independently be H or C1-C3 alkyl;

wherein n is 0-2;

wherein $R^{8f}$ is hydrogen or an optionally substituted C1-C6 alkyl with OH or $NH_2$;

wherein $R^{8a}$ and $R^{8f}$ may join to form a ring;

wherein $R^{8j}$ and $R^{8k}$ are independently H or C1-C8 hydrocarbyl residue; or c) a prodrug containing substituent, wherein the compound has the structure of Formula II':

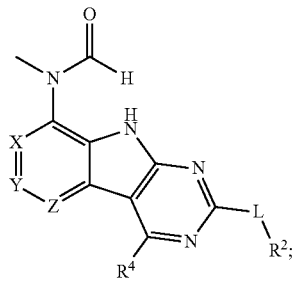

Formula II'

$R^2$ is:

a) phenyl, thiadiazolyl, pyridinyl or pyrimidinyl optionally substituted with a noninterfering substituent; or b) a prodrug-containing substituent, wherein the compound has the structure of Formula IV;

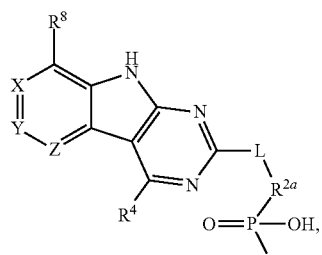

Formula IV or a pharmaceutically acceptable salt thereof;
wherein $R^{2a}$ contains an oxygen residue derived from an $R^2$ as in a) wherein $R^2$ has an OH group, wherein the $R^2$ OH is replaced with an oxygen residue in $R^{2a}$, and wherein the oxygen residue is linked to P;

$R^4$ is:

a) a C3-C20 aliphatic hydrocarbyl residue containing 1-6 heteroatoms selected from O, S, and N wherein one heteroatoms of the 1-6 heteroatoms is an N in the backbone of the hydrocarbyl residue and wherein the N is attached to the C Ring, wherein the C3-C20 aliphatic hydrocarbyl residue is substituted with at least one hydroxyl substituent and 0-3 noninterfering substituents;

wherein the $R^4$ substituent does not project greater than about 3 Å below the plane of the A, B and C Rings toward the GyrB/ParE binding pocket floor in the bound conformation; and wherein $R^4$ does not sterically interfere with $R^2$ or Z when the compound is in the bound conformation;

b) a prodrug-containing substituent, wherein the compound has the structure of Formula V:

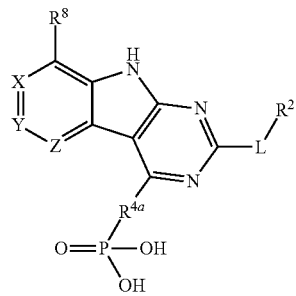

Formula V or a pharmaceutically acceptable salt thereof;
wherein $R^{4a}$ contains an oxygen residue derived from an $R^4$ as in a), wherein hydroxyl substituent of $R^4$ is replaced with an oxygen residue in $R^{4a}$, and wherein the oxygen residue is linked to P;

X is CH;

each of Y and Z may be independently $CR^Y$ or $CR^Z$ respectively, or N, wherein each of $R^Y$ and $R^Z$ is independently H, F, Cl, Br, $CH_3$, $CF_3$, $CHF_2$, $CH_2F$, or CN;

provided that the compound is not any of the following:

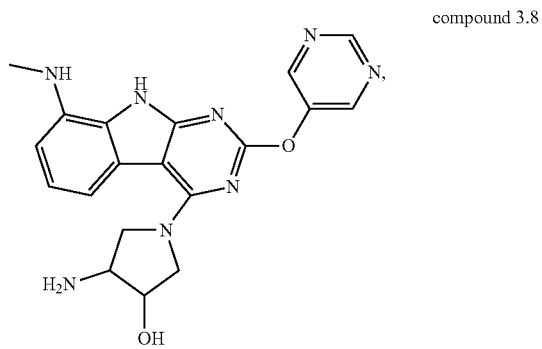

compound 3.8

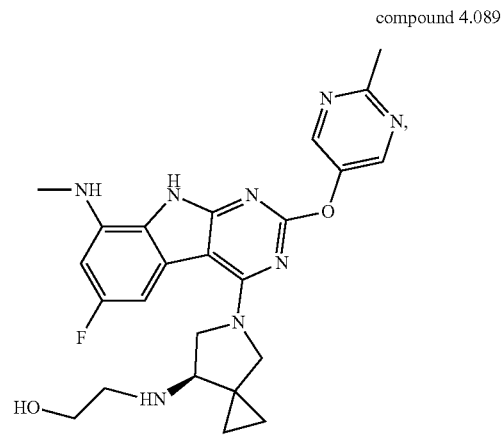

compound 4.089 compound 4.124
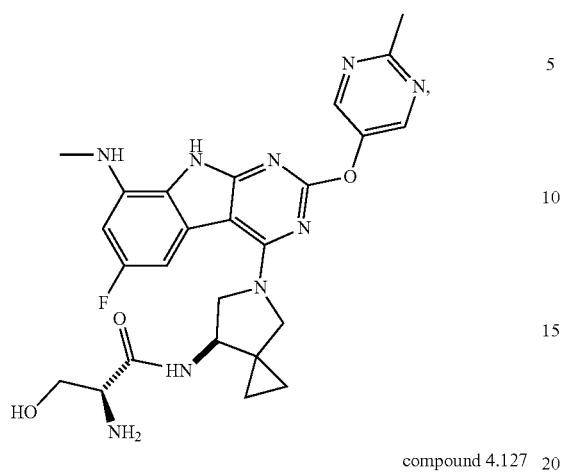
compound 4.136
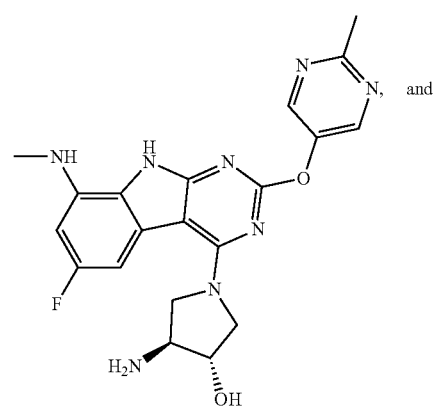
and
compound 4.127
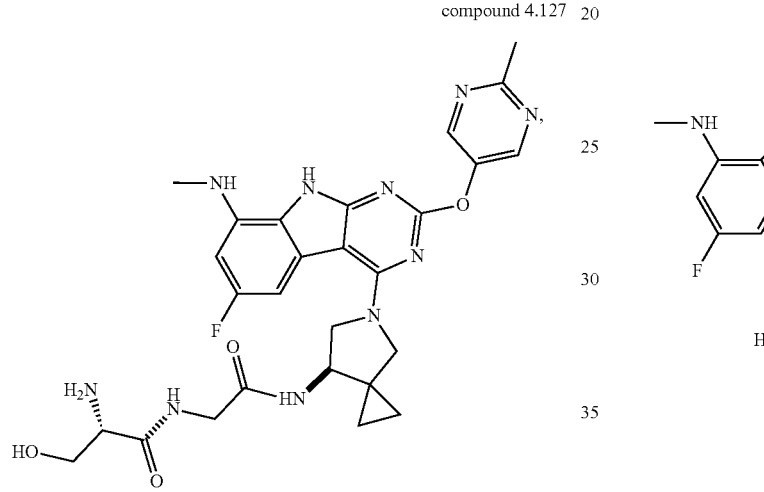
compound 4.439
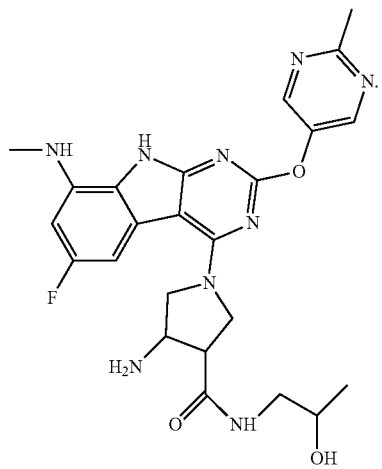
* * * * *